(12) United States Patent
Shemesh et al.

(10) Patent No.: US 8,987,191 B2
(45) Date of Patent: Mar. 24, 2015

(54) BIOACTIVE PEPTIDES AND METHODS OF USING SAME

(71) Applicant: Compugen Ltd., Tel Aviv (IL)

(72) Inventors: Ronen Shemesh, Modiin (IL); Zurit Levine, Herzlia (IL); Amir Toporik, Holon (IL); Chen Hermesh, Pardes Hana (IL); Yossef Kliger, Rishon Le Zion (IL); Eyal Gofer, Tel Aviv-Jaffa (IL); Assaf Wool, Kiriyat Ono (IL); Dvir Dahary, Tel Aviv (IL); Yossi Cohen, Woking (GB)

(73) Assignee: Compugen Ltd., Tel Aviv (IL)

( * ) Notice: Subject to any disclaimer, the term of this patent is extended or adjusted under 35 U.S.C. 154(b) by 0 days.

(21) Appl. No.: 13/923,690

(22) Filed: Jun. 21, 2013

(65) Prior Publication Data

US 2014/0005097 A1    Jan. 2, 2014

Related U.S. Application Data

(62) Division of application No. 12/668,712, filed as application No. PCT/IB2008/002447 on Jul. 11, 2008, now Pat. No. 8,492,329.

(60) Provisional application No. 60/959,370, filed on Jul. 12, 2007.

(51) Int. Cl.
| | |
|---|---|
| *A61K 38/00* | (2006.01) |
| *A61P 11/06* | (2006.01) |
| *C07K 14/47* | (2006.01) |
| *A61K 38/16* | (2006.01) |
| *A61K 38/10* | (2006.01) |
| *A61K 38/08* | (2006.01) |
| *C07K 14/78* | (2006.01) |
| *C07K 7/06* | (2006.01) |

(52) U.S. Cl.
CPC .................. *C07K 14/78* (2013.01); *C07K 14/47* (2013.01); *C07K 7/06* (2013.01); *A61K 38/00* (2013.01)
USPC ........... 514/1.7; 514/1.8; 514/21.3; 514/21.4; 514/21.7

(58) Field of Classification Search
CPC ........ A61K 38/00; C07K 14/78; C07K 14/47; C07K 7/06
See application file for complete search history.

(56) References Cited

U.S. PATENT DOCUMENTS

| | | | | |
|---|---|---|---|---|
| 6,331,298 | B1 * | 12/2001 | Ferguson et al. | ............ 424/85.1 |
| 2005/0042719 | A1 | 2/2005 | Piddington et al. | |

FOREIGN PATENT DOCUMENTS

WO            00/46373            8/2000

OTHER PUBLICATIONS

Halls et al., "Multiple Binding Sites Revealed by Interaction of Relaxin Family Peptides with Native and Chimeric Relaxin Family Peptide Receptors 1 and 2 (LGR7 and LGR8)," Journal of Pharmacology and Experimental Therapeutics, 313:677-687 (2005).
Halls et al., "Relaxin Family Peptide Receptors RXFP1 and RXFP2 Modulate cAMP Signaling by Distance Mechanisms," Molecular Pharmacology, 70(1):214-226 (2006).
La Rosa et al., "Enhanced Immune Activity of Cytotoxic T-Lymphocyte Epitope Analogs Derived from Positional Scanning Synthetic Combinatorial Libraries," Blood, Mar. 15, 2001, 97(6):1776-1786.
Muren et al., "Seven Tachykinin-Related Peptides Isolated from the Brain of the Madeira Cockroach: Evidence for Tissue-Specific Expression of Isoforms," Peptides, vol. 18, No. 1 (1997) 7-15(9).
Shemesh et al., "Discovery and Validation of Novel Peptide Agonists for G-Protein-Coupled Receptors," Journal of Biological Chemistry, 283(50): 34643-34649 (2008).

* cited by examiner

*Primary Examiner* — Marcela M Cordero Garcia
*Assistant Examiner* — Sergio Coffa
(74) *Attorney, Agent, or Firm* — Occhiuti & Rohlicek LLP

(57) ABSTRACT

Disclosed are peptide ligands for G-protein coupled receptors that are useful for treating disorders associated with G-protein coupled receptor activation.

24 Claims, 27 Drawing Sheets

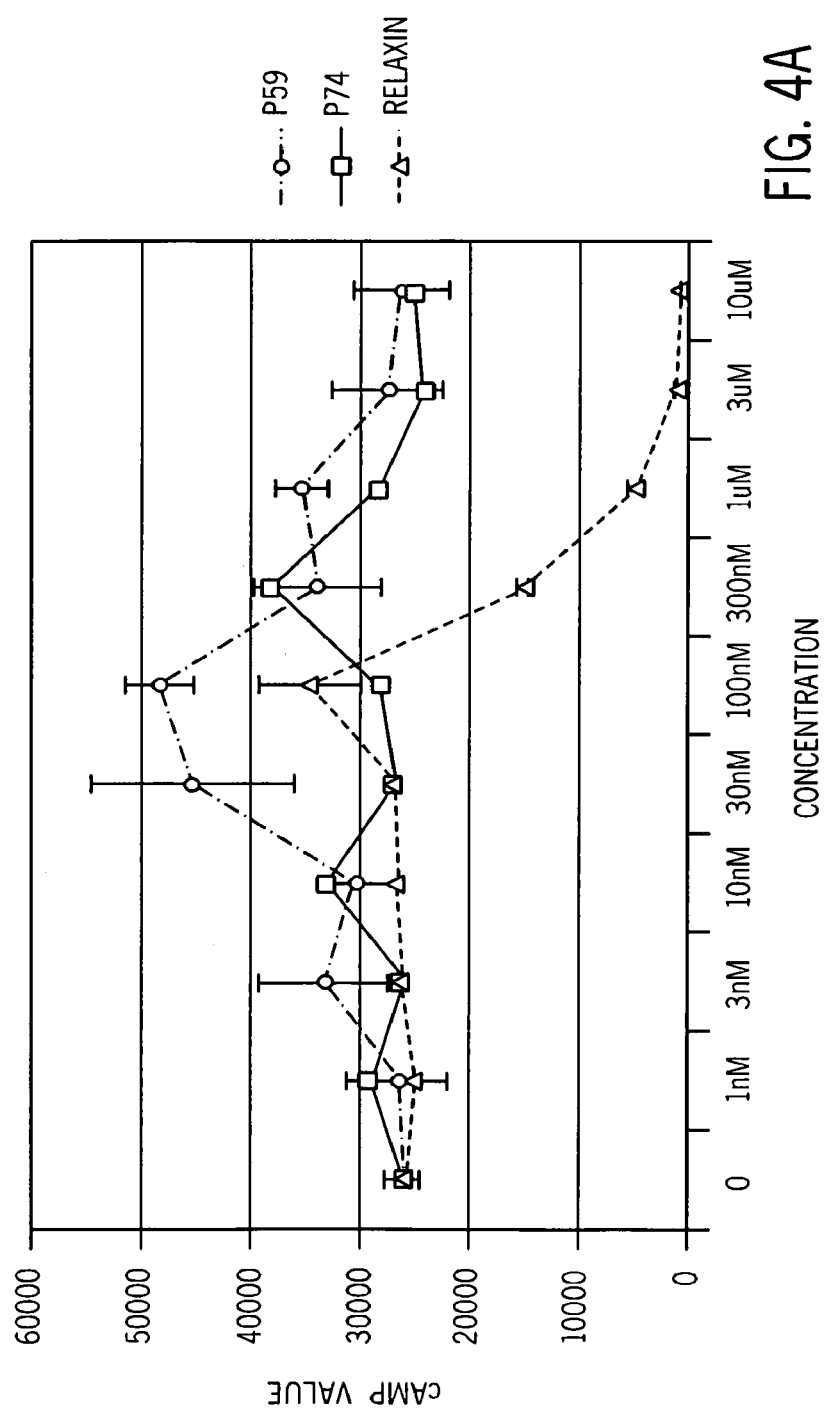

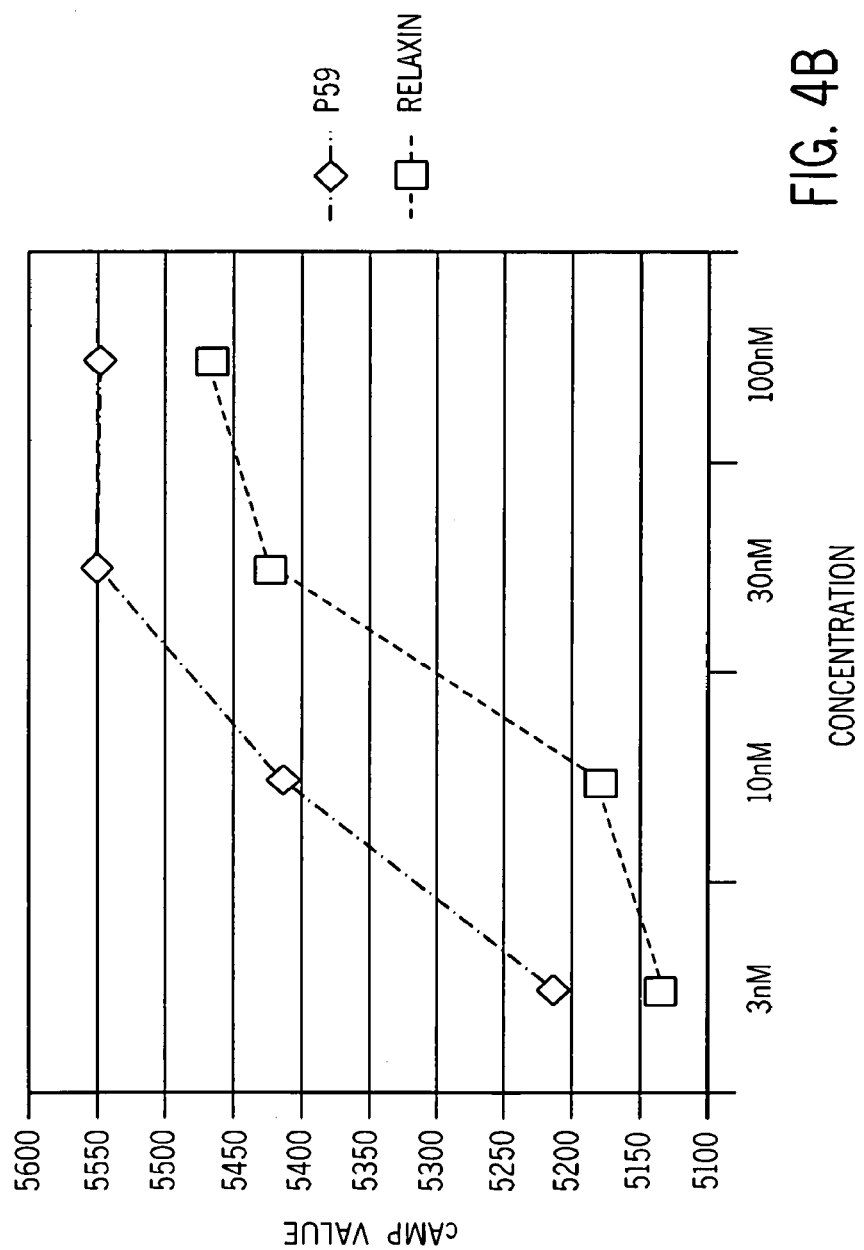

Figure 20

```
                  1         10        20    27
                  |---------+---------+------|
       Human    RRGQKGQVGPPGAACRRAYAAFSVGRR    (SEQ ID NO: 27)
       Chimp    RKGQKGQVGPPGAACQRAYAAFSVGRR    (SEQ ID NO: 28)
    Oranutan    RKGQKGQVGPPGAPCQRAYAAFSVGRR    (SEQ ID NO: 29)
      Rhesus    RKGQKGQVGPPGAPCQRAYAAFSVGRR    (SEQ ID NO: 30)
         Cow    RKGQKGQAGLPGAQCPRAYAAFSVGRR    (SEQ ID NO: 31)
     Chicken    RKGQKGQPGPQGHSCKQLYAAFSVGRR    (SEQ ID NO: 32)
       Q1TNF1   PKGQKGSMGAPGERCKSHYAAFSVGRK    (SEQ ID NO: 33)
         RAT    PKGQKGSMGAPGDHCKSQYAAFSVGRR    (SEQ ID NO: 34)
   Consensus    rkGQKGq.GppG..Ck..YAAFSVGRr    (SEQ ID NO: 35)
```

BIOACTIVE PEPTIDES AND METHODS OF USING SAME

CROSS REFERENCE TO RELATED APPLICATIONS

This application is a divisional of U.S. application Ser. No. 12/668,712 filed on Jun. 7, 2010 which is a National Stage of International Application No. PCT/IB2008/002447 filed on Jul. 11, 2008, which in turn claims priority to U.S. Provisional Application No. 60/959,370, filed Jul. 12, 2007. The contents of these applications are hereby incorporated by reference in their entireties.

FIELD OF THE INVENTION

The invention relates to bioactive peptides.

BACKGROUND OF THE INVENTION

Known and uncharacterized GPCRs currently constitute major targets for drug action and development. There are ongoing efforts to identify new G protein coupled receptors and to deorphanize known GPCRs, which can be used to screen for new agonists and antagonists having potential prophylactic and therapeutical properties.

SUMMARY OF THE INVENTION

The invention is based in part on the identification of novel peptides, variants, homologs, orthologs or derivatives thereof:

```
Peptide P59-S-Amide (Amide):
                                                (SEQ ID NO: 1)
AYAAFSV-Amide;

Peptide P59-SG (free acid Gly)
                                                (SEQ ID NO: 2)
AYAAFSV;

Peptide P59-Amide (amide)
                                                (SEQ ID NO: 3)
GQKGQVGPPGAACRRAYAAFSV-Amide;

Peptide P59 (free acid)
                                                (SEQ ID NO: 4)
GQKGQVGPPGAACRRAYAAFSV;

Peptide P59C13V-Amide (amide)
                                                (SEQ ID NO: 5)
GQKGQVGPPGAAVRRAYAAFSV-Amide Peptide P59C13V (free acid)
                                                (SEQ ID NO: 6)
GQKGQVGPPGAAVRRAYAAFSV;

Peptide P74-Amide (Amide):
                                                (SEQ ID NO: 7)
GQKGQVGPPGAACRRAYAAFSVGRRAYAAFSV-Amide Peptide P74 (free acid)
                                                (SEQ ID NO: 8)
GQKGQVGPPGAACRRAYAAFSVGRRAYAAFSV Peptide P74C13V (amide)
                                                (SEQ ID NO: 9)
GQKGQVGPPGAAVRRAYAAFSVGRRAYAAFSV-Amide Peptide P74C13V (free acid)
                                                (SEQ ID NO: 10)
GQKGQVGPPGAAVRRAYAAFSVGRRAYAAFSV Peptide P59SG (free acid Gly)
                                                (SEQ ID NO: 11)
AYAAFSVG;

Peptide P59-G (free acid Gly)
                                                (SEQ ID NO: 12)
GQKGQVGPPGAACRRAYAAFSVG;

Peptide P59C13V-G (free acid Gly)
                                                (SEQ ID NO: 13)
GQKGQVGPPGAAVRRAYAAFSVG;

Peptide P74-G (free acid Gly)
                                                (SEQ ID NO: 14)
GQKGQVGPPGAACRRAYAAFSVGRRAYAAFSVG Peptide P74C13V-G (free acid Gly)
                                                (SEQ ID NO: 15)
GQKGQVGPPGAAVRRAYAAFSVGRRAYAAFSVG Peptide P59-Chimpanzee
                                                (SEQ ID NO: 20)
GQKGQVGPPGAACQRAYAAFSVG;

Peptide P59-Orangutan
                                                (SEQ ID NO: 21)
GQKGQVGPPGAPCQRAYAAFSVG;

Peptide P59-Rhesus
                                                (SEQ ID NO: 22)
GQKGQVGPPGAPCQRAYAAFSVG;

Peptide P59-Cow
                                                (SEQ ID NO: 23)
GQKGQAGLPGAQCPRAYAAFSVG;

Peptide P59-Chicken
                                                (SEQ ID NO: 24)
GQKGQPGPQGHSCKQLYAAFSVG;

Peptide P59-C1QTNF1 (Human)
                                                (SEQ ID NO: 25)
GQKGSMGAPGERCKSHYAAFSVG;

Peptide P59-Rat
                                                (SEQ ID NO: 26)
GQKGSMGAPGDHCKSQYAAFSVG;
``` that are ligands for the relaxin-related GPCRs, selected from the group consisting of RXFP1 (LGR7), RXFP2 (LGR8), RXFP3 and RXFP4; and/or of the LGR family GPCRs, selected from a group consisting of but not limited to LRR (A10) containing GPCRs: FSHR (LGR1), LHCGR (LGR2), TSHR (LGR3), LGR4, LGR5, LGR6, LGR7 (RXFP1) and LGR8 (RXFP2).

In one aspect, the invention features peptides less than 100 amino acids in length, wherein the peptide comprises the amino acid sequence of Formula I:

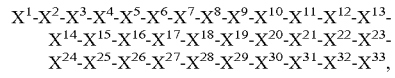

Wherein $X^1$ is absent or G or a small naturally or non-naturally occurring amino acid;

$X^2$ is absent or Q or a polar naturally or non-naturally occurring amino acid;

$X^3$ is absent or K or a basic naturally or non-naturally occurring amino acid;

$X^4$ is absent or G or a small naturally or non-naturally occurring amino acid;

$X^5$ is absent or Q or S a polar naturally or non-naturally occurring amino acid;

$X^6$ is absent or V or A or P or M or a hydrophobic naturally or non-naturally occurring amino acid;

$X^7$ is absent or G or a small naturally or non-naturally occurring amino acid;

$X^8$ is absent or P or L or A naturally or non-naturally occurring amino acid;

$X^9$ is absent or P or Q naturally or non-naturally occurring amino acid;

$X^{10}$ is absent or G or a small naturally or non-naturally occurring amino acid;

$X^{11}$ is absent or A or H or E or D or a hydrophobic or a small or an acidic naturally or non-naturally occurring amino acid;

$X^{12}$ is absent or A or P or Q or S or R or H or a hydrophobic or a small naturally or non-naturally occurring amino acid;

$X^{13}$ is absent or C or V or or a hydrophobic naturally or non-naturally occurring amino acid;

$X^{14}$ is absent or R or K or Q or P or a basic or a polar naturally or non-naturally occurring amino acid;

$X^{15}$ is absent or R or Q or S or a basic or a polar naturally or non-naturally occurring amino acid;

$X^{16}$ is absent or A or L or H or Q or a hydrophobic or a small naturally or non-naturally occurring amino acid;

$X^{17}$ is absent or Y or a hydrophobic or an aromatic naturally or non-naturally occurring amino acid;

$X^{18}$ is absent or A or a hydrophobic or small naturally or non-naturally occurring amino acid;

$X^{19}$ is absent or A or a hydrophobic small naturally or non-naturally occurring amino acid;

$X^{20}$ is absent or F or a hydrophobic or an aromatic naturally or non-naturally occurring amino acid;

$X^{21}$ is absent or S or T or a polar naturally or non-naturally occurring amino acid;

$X^{22}$ is absent or V or a hydrophobic naturally or non-naturally occurring amino acid;

$X^{23}$ is absent or G or hydrophobic or small non-naturally occurring amino acid or replaced by an Amide;

$X^{24}$ is absent or R or a basic naturally or non-naturally occurring amino acid;

$X^{25}$ is absent or R or a basic naturally or non-naturally occurring amino acid;

$X^{26}$ is A or a hydrophobic or small naturally or non-naturally occurring amino acid;

$X^{27}$ is Y or a hydrophobic or an aromatic naturally or non-naturally occurring amino acid;

$X^{28}$ is A or a hydrophobic or small naturally or non-naturally occurring amino acid;

$X^{29}$ is A or a hydrophobic or small naturally or non-naturally occurring amino acid;

$X^{30}$ is F or a hydrophobic naturally or non-naturally occurring amino acid;

$X^{31}$ is S or T or a polar naturally or non-naturally occurring amino acid;

$X^{32}$ is V or a hydrophobic naturally or non-naturally occurring amino acid;

$X^{33}$ is absent or G or hydrophobic or small naturally or non-naturally occurring amino acid or replaced by an Amide; or a pharmaceutically acceptable salt thereof.

In some embodiments, the amino acid sequence of said peptides differs by at least one, or at least two, or at least three amino acids as compared to the naturally occurring amino acid sequence set forth in SEQ ID NOs:1-15, 20-26.

In some embodiments, the peptide of this invention has at least one-forth, e.g., one third, one half, or the same activity, as the activity of a peptide of substantially identical length with a naturally occurring amino acid sequence. By "substantially identical length" is meant the same length or a difference in length of no more than ten percent.

In some embodiments, the peptide binds to a G-protein coupled receptor (GPCR) protein.

In some embodiments, the GPCR protein belongs to a relaxin-related family of GPCR proteins selected from the group consisting of relaxin-related GPCRs, including RXFP1 (LGR7), RXFP2 (LGR8), RXFP3 and RXFP4; and/or of the LGR family of GPCRs, selected from a group consisting of but not limited to LRR (A10) containing GPCRs: FSHR (LGR1), LHCGR (LGR2), TSHR (LGR3), LGR4, LGR5, LGR6, LGR7 and LGR8.

In some embodiments, the peptide inhibits forskolin-mediated increases in cAMP levels in an LG7R7 and/or LGR8 expressing CHO-K1 cell.

In some embodiments, the peptide is a degradation product of a naturally occurring protein isolated from a cell. In other embodiments, the peptide is isolated from a protein recombinantly produced in a cell. The cell can be, e.g., a prokaryotic or eukaryotic cell.

In some embodiments, the peptide is chemically synthesized in vitro.

If desired, the he peptide can be provided coupled to a biotin moiety.

In some embodiments, the peptide includes a disulfide bond.

The peptide can be provided as a linear or cyclic peptide. In some embodiments, the peptide is a cyclic lactam. In some embodiments, the peptide is a branched peptide.

In some embodiments, the peptide is phosphorylated, e.g., at a serine, theronine, or tyrosine residue.

In some embodiments, a cysteine residue in a Peptide P59 or Peptide P73 sequence is replaced with a second amino acid, e.g., one that prevents dimerization. Examples of suitable amino acids include leucine, isoleucine, alanine, and valine.

In some embodiments, the peptide is modified at its amino terminus. Example of amino terminal modifications include an N-glycated, N-alkylated, N-acetylated or N-acylated amino acid.

In some embodiments, the peptide is pegylated.

In some embodiments, the peptide includes a C-terminal amidated amino acid. In other embodiments, the peptide does not include an amidated amino acid at its carboxy terminus.

In some embodiments, the non-naturally occurring amino acid is an omega-amino acid, e.g. beta-alanine (beta-Ala), or 3 aminopropionic (3-aP).

In some embodiment, the peptide includes a small non-naturally occurring amino acid, e.g., sarcosine (Sar), β-alanine (β-Ala), 2,3 diaminopropionic (2,3-diaP) or alpha-aminisobutyric acid (Aib); omega-acid beta-alanine (beta-Ala), or 3 aminopropionic (3-aP) acid In some embodiments, the peptide includes a hydrophobic non-naturally occurring amino acid, e.g., t butylalanine (t BuA), t butylglycine (t BuG), N methylisoleucine (N MeIle), norleucine (Nle), methylvaline (Mvl), cyclohexylalanine (Cha), phenylglycine (Phg), NaI, β2-thienylalanine (Thi), 2 naphthylalanine (2 NaI), or 1,2,3,4-tetrahydroisoquinoline-3 carboxylic acid (Tic).

In some embodiments, the peptide includes a basic non-naturally occurring amino acid, e.g., ornithine (Orn) or homoarginine (Har).

In some embodiments, the peptide includes a neutral and polar non-naturally occurring amino acid, e.g., citrulline (Cit), Acetyl Lys, or methionine sulfoxide (MSO).

In some embodiments, the peptide is less than 225, 200, 175, 150, 125, 100, 75, 50, 30, 25, 20, 15, 10, 9, 8, 7, 6, or 5 amino acids.

Peptides can be modified to include one or more modifications. Thus, in some embodiments, the carboxy terminus is amidated and an internal cysteine is replaced with a valine at position 13 (C13V) in Formula I, above. In other embodiments, both modifications are present:

```
Peptide P-59S (amide)
                                            (SEQ ID NO: 1)
AYAAFSV-Amide;

Peptide P-59S (free acid)
                                            (SEQ ID NO: 2)
AYAAFSV;

Peptide P59-Amide (amide)
                                            (SEQ ID NO: 3)
GQKGQVGPPGAACRRAYAAFSV-Amide;

Peptide P59 (free acid)
                                            (SEQ ID NO: 4)
GQKGQVGPPGAACRRAYAAFSV;

Peptide P59C13V-Amide (amide)
                                            (SEQ ID NO: 5)
GQKGQVGPPGAAVRRAYAAFSV-Amide Peptide P59C13V (free acid)
                                            (SEQ ID NO: 6)
GQKGQVGPPGAAVRRAYAAFSV;

Peptide P74-Amide (amide)
                                            (SEQ ID NO: 7)
GQKGQVGPPGAACRRAYAAFSVGRRAYAAFSV Amide Peptide P74 (free acid)
                                            (SEQ ID NO: 8)
GQKGQVGPPGAACRRAYAAFSVGRRAYAAFSV Peptide P74C13V-Amide (amide)
                                            (SEQ ID NO: 9)
GQKGQVGPPGAAVRRAYAAFSVGRRAYAAFSV Amide Peptide P74C13V (free acid)
                                            (SEQ ID NO: 10)
GQKGQVGPPGAAVRRAYAAFSVGRRAYAAFSV.

Peptide P59SG (free acid Gly)
                                            (SEQ ID NO: 11)
AYAAFSVG;

Peptide P59-G (free acid Gly)
                                            (SEQ ID NO: 12)
GQKGQVGPPGAACRRAYAAFSVG;

Peptide P59C13V-G (free acid Gly)
                                            (SEQ ID NO: 13)
GQKGQVGPPGAAVRRAYAAFSVG;

Peptide P74-G (free acid Gly)
                                            (SEQ ID NO: 14)
GQKGQVGPPGAACRRAYAAFSVGRRAYAAFSVG Peptide P74C13V-G (free acid Gly)
                                            (SEQ ID NO: 15)
GQKGQVGPPGAAVRRAYAAFSVGRRAYAAFSVG Peptide P59-Chimpanzee
                                            (SEQ ID NO: 20)
GQKGQVGPPGAACQRAYAAFSVG;

Peptide P59-Orangutan
                                            (SEQ ID NO: 21)
GQKGQVGPPGAPCQRAYAAFSVG;

Peptide P59-Rhesus
                                            (SEQ ID NO: 22)
GQKGQVGPPGAPCQRAYAAFSVG;

Peptide P59-Cow
                                            (SEQ ID NO: 23)
GQKGQAGLPGAQCPRAYAAFSVG;

Peptide P59-Chicken
                                            (SEQ ID NO: 24)
GQKGQPGPQGHSCKQLYAAFSVG;

Peptide P59-C1QTNF1 (Human)
                                            (SEQ ID NO: 25)
GQKGSMGAPGERCKSHYAAFSVG;

Peptide P59-Rat
                                            (SEQ ID NO: 26)
GQKGSMGAPGDHCKSQYAAFSVG.
```

The invention in another embodiment includes any one of the foregoing peptides, wherein said peptide is conjugated or fused to a second peptide or polypeptide, optionally wherein said second peptide or polypeptide are multiple antigenic peptides (MAP), or wherein said second peptide or polypeptide comprises a portion of an immunoglobulin, or wherein said second peptide or polypeptide comprises albumin or a portion of albumin.

The invention in another embodiment includes any one of the foregoing peptides, wherein said second peptide or polypeptide includes a signal sequence.

The invention in another embodiment includes any one of the foregoing peptides, wherein signal sequence comprises: MAAPALLLLALLLPVGA (SEQ ID NO:11), MAAPALLLLALLLPVGAWP (SEQ ID NO:12), MAAPALLLLALLLPVGAWPGLP (SEQ ID NO:13).

The invention in another embodiment includes a pharmaceutical composition comprising any one of the foregoing peptides and a pharmaceutically acceptable carrier.

The invention in another embodiment includes a peptide comprising a fragment of any one of the foregoing peptides, wherein said peptide fragment binds or activates a G-protein coupled receptor (GPCR) protein, optionally wherein said GPCR protein belongs to the family of proteins, selected from the group consisting of relaxin-related GPCRs, including RXFP1 (LGR7), RXFP2 (LGR8), RXFP3 and RXFP4; and/or of the LGR family of GPCRs, selected from a group consisting of but not limited to LRR (A10) containing GPCRs: FSHR (LGR1), LHCGR (LGR2), TSHR (LGR3), LGR4, LGR5, LGR6, LGR7 and LGR8.

The invention in another embodiment includes a purified nucleic acid sequence encoding any one of the foregoing peptides, variants, homoplogus, ortholoqus or derivatives thereof.

The invention in another embodiment includes a method of treating a disorder where modulation or activation of a relaxin-related GPCR and/or LGR family of GPCR receptor or receptors is efficacious and/or of therapeutic value, the method comprising administering to the subject a therapeutically effective amount of a peptide of Formula I. The disorder is selected from but not limited to hyperplastic disorders, neoplastic disorders, cancer; fibrotic conditions, disorders of collagen deposition, fibrotic breakdown, connective tissue remodeling, uncontrolled or abnormal collagen or fibronectin formation or breakdown; skin injuries including wound healing and scarring, scleroderma; urogenital disorders including female reproductive disorders, male and female infertility, cryptorchidism, disregulation of spermatogenesis and reproductive development including descent of the gonads; conditions associated with pregnancy such as preeclampsia or complication of labor; angiogenesis related disorders; cardiovascular disorders, vasodilatation, vasoconstriction or hypertension, endothelial disfunction and vascular disease, congestive heart failure, coronary artery disease, ischemia and ischemia-reperfusion, peripheral vascular disease; kidney disease, renal disease associated with arteriosclerosis or other narrowing of kidney capillaries; capillaries narrowing in the body, such as in the eyes or in the peripheral digits, the mesocaecum, lung and peripheral vasculature; CNS related disorders, neurological disorders, cognition and memory related indications, depression, neurological modification; inflammatory disorders, such as gastritis, gout, gouty arthritis, arthritis, rheumatoid arthritis, inflammatory bowel disease, Crohn's disease, ulcerative colitis, ulcers; autoimmune disorders; inflammatory conditions associated with viral infection and infection related diseases including fibrosis and cirrhosis; Raynaud's disease, Raynaud's phenomenon; bone related conditions including osteoporosis; metabolic disorders including food and water intake, diabetes, obesity; respiratory or a pulmonary disorder, including asthma, COPD, bronchial disease, lung diseases, cystic fibrosis, ARDS, SARS.

The invention in another embodiment includes a method of treating a hypertension and its complications, said method comprising administering to a subject in need thereof a therapeutically effective amount of any one of the foregoing peptides, wherein said peptide is Formula I.

The invention in another embodiment includes the foregoing method, wherein said hypertension associated disorder is selected from the group consisting of hypertension and its complications including but not limited to hypertensive heart disease; antihypertension (blood pressure reduction); systemic and pulmonary high blood pressure; cerebrovascular disease and stroke; heart failure and stroke; left ventricular hypertrophy (LVH); congestive heart failure (CHF); hypertension, high blood pressure; vasodilation; renal hypertension; diuresis; nephritis; natriuresis; scleroderma renal crisis; angina pectoris (stable and unstable); myocardial infarction; heart attack; coronary artery disease; coronary heart disease; cardiac arrhythmias; atrial fibrillation; portal hypertension; raised intraocular pressure; vascular restenosis; chronic hypertension; valvular disease; myocardial ischemia; acute pulmonary edema; acute coronary syndrome; hypertensive retinopathy; hypertensive pregnancy sickness; preeclampsia; Raynaud's phenomenon; erectile dysfunction, glaucoma. These peptides are also used as a vasodilator and in antithrombotic therapy The invention in another embodiment includes a method of treating a cardiovascular diseases and their-complications, said method comprising administering to a subject in need thereof a therapeutically effective amount of any one of the foregoing peptides, wherein said peptide is Formula I.

The invention in another embodiment includes the foregoing method, wherein said cardiovascular disorder is selected from a group consisting of peripheral vascular diseases and coronary artery diseases, including but not limited to myocardial infarction; congestive heart failure (CHF); myocardial failure; myocardial hypertrophy; ischemic cardiomyopathy; systolic heart failure; diastolic heart failure; stroke; thrombotic stroke; concentric LV hypertrophy, myocarditis; cardiomyopathy; hypertrophic cardiomyopathy; myocarditis; decompensated heart failure; ischemic myocardial disease; congenital heart disease; angina pectoris; prevention of heart remodeling or ventricular remodeling after myocardial infarction; ischemia-reperfusion injury in ischemic and post-ischemic events (e.g. myocardial infarct); cerebrovascular accident; mitral valve regurgitation; hypertension; hypotension; restenosis; fibrosis; thrombosis; or platelet aggregation.

The invention in another embodiment includes a method of treating a fibrotic condition in a subject, involving tissue remodeling following inflammation or ischemia-reperfusion injury, said method comprising administering to a subject in need thereof a therapeutically effective amount of anyone of the foregoing peptides, wherein said peptide is Formula I.

The invention in another embodiment includes the foregoing method, wherein said fibrotic conditions is selected from a group consisting of fibrotic conditions involving tissue remodeling following inflammation or ischemia-reperfusion injury, including but not limited to endomyocardial and cardiac fibrosis fibrosis; mediastinal fibrosis; idiopathy pulmonary fibrosis; pulmonary fibrosis; retroperitoneal fibrosis; fibrosis of the spleen; fibrosis of the pancreas; hepatic fibrosis (cirrhosis) alcohol and non-alcohol related (including viral infection such as HAV, HBV and HCV); fibromatosis; granulomatous lung disease; glomerulonephritis myocardial scarring following infarction; endometrial fibrosis and endometriosis; wound healing whether by injury or surgical procedures, diabetes related wound fibrosis.

The invention in another embodiment includes a method of treating a endothelial dysfunction disease in a subject, said method comprising administering to a subject in need thereof a therapeutically effective amount of anyone of the foregoing peptides, wherein said peptide is Formula I.

The invention in another embodiment includes the foregoing method, wherein said endothelial dysfunction disease is selected from a group consisting of cardiovascular diseases, high blood pressure, atherosclerosis, thrombosis, myocardial infarct, heart failure, renal diseases, plurimetabolic syndrome, erectile dysfunction; vasculitis; and diseases of the central nervous system (CNS).

The invention in another embodiment includes a method of treating a respiratory disease in a subject, said method comprising administering to a subject in need thereof a therapeutically effective amount of anyone of the foregoing peptides, wherein said peptide is Formula I.

The invention in another embodiment includes the foregoing method, wherein said respiratory disease is selected from a group consisting of including but not limited to asthma, bronchial disease, lung diseases, chronic obstructive pulmonary disease (COPD), Acute Respiratory Distress Syndrome (ARDS), severe acute respiratory syndrome (SARS), Fibrosis related Asthma, cystic fibrosis.

The invention in another embodiment includes a method of preventing or treating a skin injury or tissue repair, said method comprising administering to a subject in need thereof a therapeutically effective amount of anyone of the foregoing peptides, wherein said peptide is Formula I.

The invention in another embodiment includes the foregoing method, wherein said skin injury is selected from a group including but not limited to dermal repair, wound healing; burns, erythemas, lesions, wound healing following surgical procedures; skin or tissue lesions including lesions induced by conditions including, but not limited to Psoriasis, Lupus and Kaposhi Sarcoma; Scleroderma and collagenous diseases of the skin and skin tumors.

The invention in another embodiment includes a method of treating a urogenital disorder or a genitor-urological disorder in a subject, said method comprising administering to a subject in need thereof a therapeutically effective amount of anyone of the foregoing peptides, wherein said peptide is Formula I.

The invention in another embodiment includes the foregoing method, wherein said urogenital disorder or genitor-urological disorders is selected from group consisting of urogenital disorder or a genitor-urological disorders including but not limited to renal disease; a bladder disorder; disorders of the reproductive system; gynecologic disorders; urinary tract disorder; incontinence; disorders of the male (spermatogenesis, spermatic motility), and female reproductive system;

sexual dysfunction; erectile dysfunction; embryogenesis; and conditions associated with pregnancy. These are also used in pregnancy monitoring. As used herein, the term "conditions associated with pregnancy" includes, but is not limited to, conditions of fertilisation, pregnancy, parturition and lactation. The invention in another embodiment includes using the peptides of the invention falling within Formulas I, such as for example, peptides as depicted in SEQ ID NOs:6-7, 9-16, 18-25, 27-31, wherein said pregnancy related disorders are selected from a group consisting of Abnormal endometrial angiogenesis; Placental development defects; Cervical ripening (softening); Abnormal implantation; Nipple development and disfunction; Pregnancy related remodeling of the Uterine tissue; Endometriosis; Preeclampsia; Lactation disorders; Estrogenic and non-estrogenic related hormonal disorders; Pre-term labor; post term labor; and Labor complications.

The invention in another embodiment includes a method of treating a cancer or inflammation associated with cancer in a patient, said method comprising administering to a subject in need thereof a therapeutically effective amount of anyone of the foregoing peptides, wherein said peptide is Formula I.

The invention in another embodiment includes the foregoing method, wherein said cancer is selected from a group consisting of solid cancer, including but not limited to colon cancer, lung cancer, breast cancer, prostate cancer, brain cancer, pancreatic cancer, ovarian cancer, kidney cancer, testicular cancer, bone cancer, osteosarcoma, or liver cancer (HBV/HCV related or non-related). The cancer can alternatively be a melanoma, glioma, a sarcoma, a leukemia, or lymphoma. These peptides are also useful in the prevention or treatment of invasive and metastatic cancer.

The invention in another embodiment includes a method of treating a bone and bone related disorders in a patient, said method comprising administering to a subject in need thereof a therapeutically effective amount of anyone of the foregoing peptides, wherein said peptide is Formula I.

The invention in another embodiment includes the foregoing method, wherein said bone disease is selected from a group including but not limited to Osteoporosis; Osteoarthritis; Osteopetrosis; Bone inconsistency; Osteosarcoma; and Cancer matastesis to the bone.

The invention in another embodiment includes a method of treating a metabolic and metabolic related disorders in a patient, said method comprising administering to a subject in need thereof a therapeutically effective amount of anyone of the foregoing peptides, wherein said peptide is Formula I.

The invention in another embodiment includes the foregoing method, wherein said metabolic disorder is selected from a group including but not limited to diabetes, diabetes mellitus, lipodystrophy, hyperthyroidism, glaucoma, hyperlipidaemia, non-insulin dependent diabetes, Food intake; Water intake; Feeding and drinking behaviors, Anorexia, Cachexia (cancer and non cancer related); Fat and lipid metabolism; and Energy control, appetite control and obesity.

The invention in another embodiment includes a method of treating a CNS and cognition disorders in a patient, said method comprising administering to a subject in need thereof a therapeutically effective amount of anyone of the foregoing peptides, wherein said peptide is Formula I.

The invention in another embodiment includes the foregoing method, wherein said CNS and cognition disorders are selected from a group including but not limited to central and peripheral degenerative neuropathies; neuroprotection; impaired cognition; anxiety disorders, pain control, food intake, a behavioral disorder, a learning disorder, a sleep disorder, a memory disorder, a pathologic response to anesthesia, addiction, depression, migraine, a menstruation disorder, muscle spasm, opiate dependence, dementia, Alzheimer's disease, Parkinson's disease, cortical function, locomotor activity, Alcohol and Drug addiction and abuse; Impaired memory; Feeding and drinking related behaviours; Stress control, Bipolar disorder; Schizophrenia; Schizoaffective; Multiple Sclerosis (MS); Stroke and stroke damage repair (Ischemia protection); Vasculature and re-vasculature in the brain; and Brain tissue regeneration and a peripheral nervous system disorder.

The invention in another embodiment includes a method of treating ischemia-reperfusion injury associated with ischemic and post-ischemic events in organs and tissues in a patient, said method comprising administering to a subject in need thereof a therapeutically effective amount of anyone of the foregoing peptides, wherein said peptide is Formula I.

The invention in another embodiment includes the foregoing method, wherein said ischemia-reperfusion injury associated with ischemic and post-ischemic events in organs and tissues disorders are selected from a group including but not limited to thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure; restenosis; atherosclerosis; thrombosis; platelet aggregation.

The invention in another embodiment includes a method of treating ischemia-reperfusion injury following conditions including but not limited to procedures such as cardiac surgery; organ surgery; organ transplantation; angiography; cardiopulmonary and cerebral resuscitation in a patient, said method comprising administering to a subject in need thereof a therapeutically effective amount of anyone of the foregoing peptides, wherein said peptide is Formula I.

The invention in another embodiment includes a method of inflammatory conditions associated with an infection, e.g., a bacterial infection or a viral infection in a patient, said method comprising administering to a subject in need thereof a therapeutically effective amount of anyone of the foregoing peptides, wherein said peptide is Formula I.

The invention in another embodiment includes the foregoing method, wherein said inflammatory conditions associated with an infection, are selected from but not limited to including but not limited to a viral infection caused by human immunodeficiency virus I (HIV-1) or HIV-2, acquired immune deficiency (AIDS), West Nile encephalitis virus, coronavirus, rhinovirus, influenza virus, dengue virus, HCV, HBV, HAV, hemorrhagic fever; an otological infection; severe acute respiratory syndrome (SARS), sepsis and sinusitis.

The invention in another embodiment includes a method of kidney diseases in a patient, said method comprising administering to a subject in need thereof a therapeutically effective amount of anyone of the foregoing peptides, wherein said peptide is Formula I.

The invention in another embodiment includes the foregoing method, wherein said kidney diseases are selected from but not limited to diabetic nephropathy; glomerulosclerosis; nephropathies; renal impairment; scleroderma renal crisis and chronic renal failure.

The invention in another embodiment includes a method of angiogenesis related conditions in a patient, said method comprising administering to a subject in need thereof a therapeutically effective amount of anyone of the foregoing peptides, wherein said peptide is Formula I.

The invention in another embodiment includes the foregoing method, wherein said angiogenesis related conditions are selected from but not limited to retinal angiogenesis in a number of human ocular diseases such as diabetes mellitus, retinopathy of prematury, and age-related macular degeneration, or cancer associated angiogenesis in primary or metastatic cancer, including but not limited to cancer of the prostate, brain, breast, colorectal, lung, ovarian, pancreatic, renal, cervical, melanoma, soft tissue sarcomas, lymphomas, head-and-neck, and glioblastomas.

The invention in another embodiment includes a method of inflammatory disorder in a patient, said method comprising administering to a subject in need thereof a therapeutically effective amount of anyone of the foregoing peptides, wherein said peptide is Formula I.

The invention in another embodiment includes the foregoing method, wherein said inflammatory disorder are selected from but not limited to gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyper-responsiveness, vasculitis, septic shock and inflammatory skin disorders, including but not limited to psoriasis, atopic dermatitis, eczema.

The invention in another embodiment includes a method of autoimmune disorder in a patient, said method comprising administering to a subject in need thereof a therapeutically effective amount of anyone of the foregoing peptides, wherein said peptide is Formula I. The invention in another embodiment includes the foregoing method, wherein said autoimmune disorder are selected from but not limited to multiple sclerosis, psoriasis, rheumatoid arthritis, systemic lupus erythematosus, ulcerative colitis, Crohn's disease, transplant rejection, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

The invention in another embodiment includes the cDNA that encodes the peptide sequences of the invention, which can be used in gene therapy.

If desired, gene therapy can be used to deliver to a subject a peptide according to the invention. A nucleic acid encoding the peptide can be inserted into vectors, which are then used as gene therapy vectors. Gene therapy vectors can be delivered to a subject by, for example, intravenous injection, local administration or by stereotactic injection. The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The invention in another embodiment includes combination therapy using one or more peptides of the present invention provided in combination with another therapeutic agent or agents. As used herein, the term "combination therapy" refers to treatment of a single condition or disease involving the concomitant use of more than one therapeutic agent.

The invention in another embodiment includes an antibody that selectively binds to an epitope in anyone of the foregoing peptides.

In a still further aspect, the invention provides an antibody that selectively binds to an epitope in the peptide of Formula I.

In some embodiments, the antibody binds selectively and/or is raised to the following sequences:

```
Peptide P-59S-Amide (amide)
                                            (SEQ ID NO: 1)
AYAAFSV-Amide;

Peptide P-59S (free acid)
                                            (SEQ ID NO: 2)
AYAAFSV;

Peptide P59-Amide (amide)
                                            (SEQ ID NO: 3)
GQKGQVGPPGAACRRAYAAFSV-Amide;

Peptide P59 (free acid)
                                            (SEQ ID NO: 4)
GQKGQVGPPGAACRRAYAAFSV;

Peptide P59C13V-Amide (amide)
                                            (SEQ ID NO: 5)
GQKGQVGPPGAAVRRAYAAFSV-Amide Peptide P59C13V (free acid)
                                            (SEQ ID NO: 6)
GQKGQVGPPGAAVRRAYAAFSV;

Peptide P74-Amide (amide)
                                            (SEQ ID NO: 7)
GQKGQVGPPGAACRRAYAAFSVGRRAYAAFSV Amide Peptide P74 (free acid)
                                            (SEQ ID NO: 8)
GQKGQVGPPGAACRRAYAAFSVGRRAYAAFSV Peptide P74C13V-Amide (amide)
                                            (SEQ ID NO: 9)
GQKGQVGPPGAAVRRAYAAFSVGRRAYAAFSV Amide Peptide P74C13V (free acid)
                                            (SEQ ID NO: 10)
GQKGQVGPPGAAVRRAYAAFSVGRRAYAAFSV.

Peptide P59SG (free acid Gly)
                                            (SEQ ID NO: 11)
AYAAFSVG;

Peptide P59-G (free acid Gly)
                                            (SEQ ID NO: 12)
GQKGQVGPPGAACRRAYAAFSVG;

Peptide P59C13V-G (free acid Gly)
                                            (SEQ ID NO: 13)
GQKGQVGPPGAAVRRAYAAFSVG;

Peptide P74-G (free acid Gly)
                                            (SEQ ID NO: 14)
GQKGQVGPPGAACRRAYAAFSVGRRAYAAFSVG Peptide P74C13V-G (free acid Gly)
                                            (SEQ ID NO: 15)
GQKGQVGPPGAAVRRAYAAFSVGRRAYAAFSVG
```

```
Peptide P59-Chimpanzee
                                            (SEQ ID NO: 20)
GQKGQVGPPGAACQRAYAAFSVG;

Peptide P59-Orangutan
                                            (SEQ ID NO: 21)
GQKGQVGPPGAPCQRAYAAFSVG;

Peptide P59-Rhesus
                                            (SEQ ID NO: 22)
GQKGQVGPPGAPCQRAYAAFSVG;

Peptide P59-Cow
                                            (SEQ ID NO: 23)
GQKGQAGLPGAQCPRAYAAFSVG;

Peptide P59-Chicken
                                            (SEQ ID NO: 24)
GQKGQPGPQGHSCKQLYAAFSVG;

Peptide P59-C1QTNF1 (Human)
                                            (SEQ ID NO: 25)
GQKGSMGAPGERCKSHYAAFSVG;

Peptide P59-Rat
                                            (SEQ ID NO: 26)
GQKGSMGAPGDHCKSQYAAFSVG.
```

The invention in another embodiment includes anyone of the foregoing antibodies, wherein the antibody is a monoclonal antibody.

The invention in another embodiment includes anyone of the foregoing antibodies, wherein the antibody is conjugated or coupled to a detectable label, a radioactive label, an enzyme, a fluorescent label, a luminescent label, a bioluminescent label, or a therapeutic agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 4A is a graph showing cAMP dose response activation following treatment pre-treated with 20 uM of Forskolin and treatment with increasing doses (1 nM-10 uM) of P59C13V (P59), P74C13V (P74) or relaxin, on CHO-K1 cells transiently transfected with LGR7.

FIG. 4B is a graph showing Gs (cAMP increase) dose response activation following treatment with low concentrations (1-100 nM) of P59C13V (P59) or relaxin on CHO-K1 cells transiently transfected with LGR7.

FIG. 16A: The X axis represents time of experiment (challenge time is indicated by a vertical line), and the Y axis represents the cell index (a measurement of the change in Cell impedance) normalized to the peptide challenge time (indicated by the left vertical line). Each line represents a different concentration (according to legend). FIG. 16B: a dose response curve as calculated by the ACEA RT-CES system according to the results in FIG. 16A. The X axis represents the peptide's concentration in log of M. The Y axis represents the normalized cell index at the end point of the experiment (indicated by the right vertical line in FIG. 16A). The code for FIG. 16A is as follows: 0.16 nM; 0.8 nM; 4 nM; 20 nM; 100 nM; and 500 nM are represented by black circles; triangles; squares; diamond-shapes; white circles; and horizontal lines, respectively.

FIG. 17A: The X axis represents time of experiment (challenge time is indicated by a vertical line), and the Y axis represents the cell index (a measurement of the change in Cell impedance) normalized to the peptide challenge time (indicated by the left vertical line). Each line represents a different concentration (according to legend). FIG. 17B: a dose response curve as calculated by the ACEA RT-CES system according to the results in FIG. 17A. The X axis represents the peptide's concentration in log of M. The Y axis represents the normalized cell index at the end point of the experiment (indicated by the right vertical line in FIG. 17A). The code for FIG. 17A is as follows: 41 nM; 123 nM; 370 nM; 1.1 uM; 3.3 uM; and 10 uM are represented by black circles; triangles; squares; diamond-shapes; white circles; and horizontal lines, respectively.

FIG. 18A: The X axis represents time of experiment (challenge time is indicated by a vertical line), and the Y axis represents the cell index (a measurement of the change in Cell impedance) normalized to the peptide challenge time (indicated by the left vertical line). Each line represents a different concentration (according to legend). FIG. 18B: a dose response curve as calculated by the ACEA RT-CES system according to the results in FIG. 18A. The X axis represents the peptide's concentration in log of M. The Y axis represents the normalized cell index at the end point of the experiment (indicated by the right vertical line in FIG. 18A). The code for FIG. 18A is as follows: 41 nM; 123 nM; 370 nM; 1.1 uM; 3.3 uM; and 10 uM are represented by black circles; triangles; squares; diamond-shapes; white circles; and horizontal lines, respectively.

FIG. 18A: The X axis represents time of experiment (challenge time is indicated by a vertical line), and the Y axis represents the cell index (a measurement of the change in Cell impedance) normalized to the peptide challenge time (indicated by the left vertical line). Each line represents a different concentration (according to legend). FIG. 19B: a dose response curve as calculated by the ACEA RT-CES system according to the results in FIG. 19A. The X axis represents the peptide's concentration in log of M. The Y axis represents the normalized cell index at the end point of the experiment (indicated by the right vertical line in FIG. 19A). The code for FIG. 19A is as follows: 41 nM; 123 nM; 370 nM; 1.1 uM; 3.3 uM; and 10 uM are represented by black circles; triangles; squares; diamond-shapes; white circles; and horizontal lines, respectively.

FIG. 20: This figure shows a multiple alignment of the sequence of P59-G (SEQ ID No. 12) as a part of the native precursor (C1QTNF8-SEQ. ID. No. 19), including the flanking dibasic (K or R) cleavage sites, with homologous sequences derived from different organisms, including Chimpanzee (SEQ ID No. 20), Orangutan (SEQ ID No. 21), Rhesus (SEQ ID No. 22), Cow (SEQ ID No. 23), Chicken (SEQ ID No. 24) and Rat (SEQ ID No. 26), and the corresponding peptide sequence from the human paralogue C1QTNF1 (SEQ ID No. 25) (all sequences include the flanking dibasic cleavage sites). As can be seen both the N-terminal end (4 Amino acids) and C-terminal end (7 Amino acids) are identical to all species. The cleavage sites at both ends are also highly conserved (with occasional replacement of K for an R). The middle Cysteine residue (C13) that was replaced with Valine for dimerization purposes also is highly conserved.

DETAILED DESCRIPTION OF THE INVENTION

Figure 1:
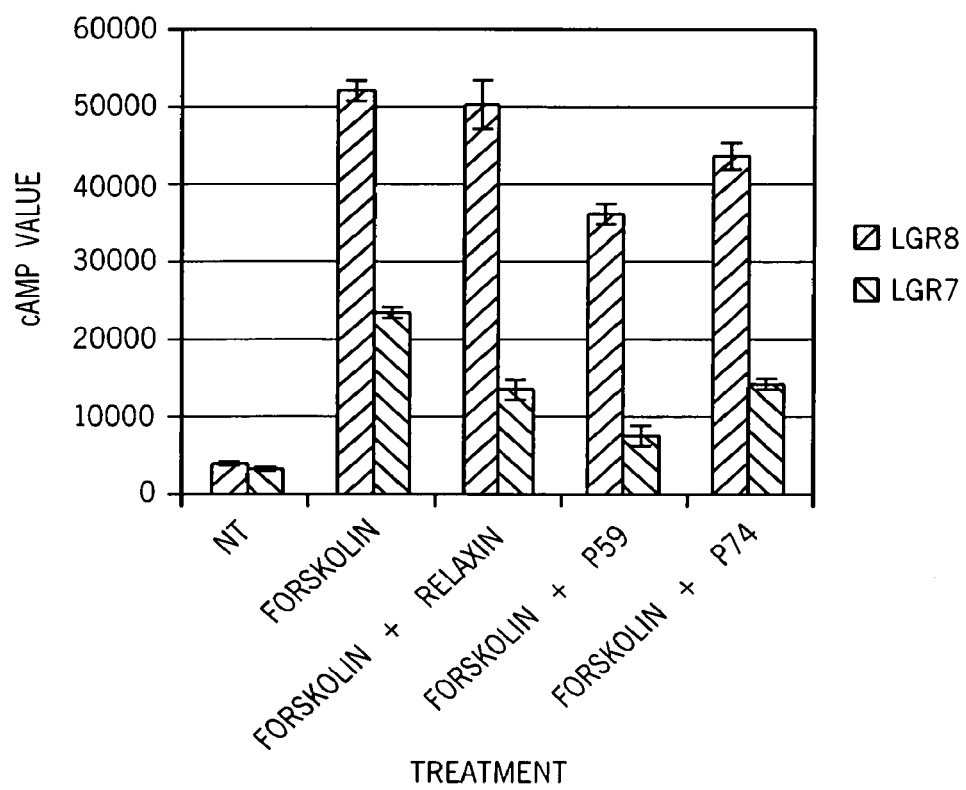
FIG. 1 is a graph showing the Gi (cAMP inhibition) effect of P59C13V (P59) and P74C13V (P74) on forskolin-treated LGR7 and LGR8 transiently transfected CHO-K1 cells.

The invention provides bioactive peptides. These peptides are useful, inter alia, for treating a variety of indications and disorders, which are discussed in detail below. In some embodiments, the peptides are ligands for GPCR receptors. The peptides disclosed herein are related to GPCR ligand of the LGR and Relaxin family:

1. The LGR family: consists of all LRR containing GPCRs including LGR1 (FSHR), LGR2 (LHCGR), LGR3 (TSHR), KGR4, LGR5, LGR6, LGR7 (RXFP1) and LGR8 (RXFP2).
2. The Relaxin related family: consists of all Relaxin activated receptors including
RXFP1 (LGR7), RXFP2 (LGR8), RXFP3 (GPCR135) and RXFP4 (GPCR142).

LGR8 (RXFP2) (SwissProt accession number: RXFP2 HUMAN) is a lower affinity receptor for relaxin (H2 and H1). The activity of this receptor is mostly but not exclusively mediated by G proteins leading to stimulation of adenylate cyclase and an increase of cAMP. Binding of the ligand activates a TRK pathway. LGR8 is also a high affinity receptor for the Leydig insulin-like 3 peptide (INSL3). LGR8 belongs to the G-protein coupled receptor 1 family. It contains 1 LDL-receptor class A domain and 10 LRR (leucine-rich) repeats. LGR8 is expressed in the brain, kidney, muscle, thyroid, testis, placenta, uterus, ovary, adrenal, prostate, skin, peripheral blood cells, bone marrow, osteoblasts and heart. Defects in LGR8 are a cause of cryptorchidism, also known as impaired testicular descent, one of the most frequent congenital abnormalities in humans, involving 2-5% of male births. Cryptorchidism is associated with increased risk of infertility and testicular cancer. LGR8 is involved in CNS related diseases like Alzheimer (Shen P J., et al., Ann N Y Acad Sci. 2005; 1041:510-5). Stimulation with relaxin increases cell proliferation, invasiveness, and adhesion in vitro. The suppression of relaxin decreased cell invasiveness by 90% and growth by 25% and increased cell apoptosis up by 2.2 times (Feng S, et al. Clin. Cancer Res. (2007). LGR8 is also involved in Osteoporosis, Female infertility and non cryptorchidism related male infertility.

LGR7 (RXFP1) (SwissProt Accession Number: RXFP1_HUMAN) is a receptor for relaxin. LGR7 binds all human relaxin peptides with high affinity, but has very low affinity for INSL3. The activity of this receptor is mediated by G proteins leading both to stimulation of adenylate cyclase and an increase of cAMP, and inhibition of adenylate cyclase and a decrease of cAMP depending on the tissue and cell type. Binding of the ligand activates a TRK pathway that inhibits the activity of a phosphodiesterase that degrades cAMP. LGR7 belongs to the G-protein coupled receptor 1 family. It contains 1 LDL-receptor class A domain and 10 LRR (leucine-rich) repeats. LGR7 is expressed in the brain, liver, kidney, testis, breast placenta, uterus, uterus endometrium, cervix, vagina, ovary, adrenal, prostate, skin, osteoclasts and heart. The LGR7 receptor is regulated by Estrogen and the activity of Estrogen receptors. LGR7 is involved in many processes including Collagen deposition and scaring, Pregnancy and labor processes including implantation and cervical ripening, Vasodilatation, Tumor progression and invasiveness, food intake and Osteoporosis.

LGR4 (SwissProt Accession Number: LGR4_HUMAN; G-protein coupled receptor 48 (GPR48)) is an orphan seven trans-membrane receptor that belongs to the G-protein coupled receptor 1 family. It contains 15 LRR (leucine-rich) repeats. LGR4 is expressed in multiple steroidogenic tissues: placenta, ovary, testis and adrenal. It is also expressed in spinal cord, thyroid, stomach, trachea, heart, pancreas, kidney, prostate and spleen.

LGR5 (SwissProt Accession Number: LGR5_HUMAN; G-protein coupled receptor 49; G-protein coupled receptor 67 (GPR49, GPR67)) is an orphan seven trans-membrane receptor that belongs to the G-protein coupled receptor 1 family. It contains 17 LRR (leucine-rich) repeats. LGR5 is predioceted to be an important receptor for signals controlling growth and differentiation of specific embryonic tissues [Morita H, et al. Mol Cell Biol. 2004 November; 24(22):9736-43].

LGR6 (SwissProt Accession Number: LGR6_HUMAN) is an orphan seven trans-membrane receptor that belongs to the G-protein coupled receptor 1 family. It contains 16 LRR (leucine-rich) repeats. LGR6 is expressed in multiple steroidogenic tissues: placenta, ovary, testis, and adrenal. It is also expressed in spinal cord, thyroid, stomach trachea, heart, pancreas, kidney, prostate and spleen.

GPCR135 (RXFP3) (SwissProt Accession Number: RL3R1_HUMAN; Relaxin-3 receptor 1, RLN3 receptor 1, Relaxin family peptide receptor 3, Somatostatin- and angiotensin-like peptide receptor, G protein-coupled receptor SALPR, GPCR135), is the receptor for relaxin-3 (H3 Relaxin). The RXFP3 receptor also has a lower affinity for Relaxin 2 (H2 Relaxin). Binding of the ligand inhibits cAMP accumulation by coupling with Gi proteins. This receptor is Expressed predominantly in brain regions. Highest expression in substantia nigra and pituitary, followed by hippocampus, spinal cord, amygdala, caudate nucleus and corpus callosum, quite low level in cerebellum. In peripheral tissues, relatively high levels in adrenal glands, low levels in pancreas, salivary gland, placenta, mammary gland and testis. Defects in this receptor's activity, as well as reduction in its primary ligand Relaxin 3 cause a decrease in body weight and feeding behaviour in mice.

GPCR142 (RXFP4) (SwissProt Accession Number: RL3R2_HUMAN; Relaxin-3 receptor 2, Relaxin family peptide receptor 4, G-protein coupled receptor 100, GPCR142), is the receptor for INSL5. This receptor is also activated by Relaxin 3, Relaxin 2 as well as bradykinin and kallidin. Binding of the ligand inhibits cAMP accumulation by coupling with Gi proteins. This receptor is expressed in a broader range of tissues including brain, kidney, testis, thymus, placenta, prostate, salivary gland, thyroid and colon.

The relaxin ligands superfamily currently comprises 10 members with a relatively high degree of sequence homology. These family members include insulin, insulin-like grown factors I and II, relaxin 1, 2 and 3, and the insulin-like hormones INSL3, 4, 5 and 6. The relaxin superfamily members have a wide range of biological activities which are well described in the art.

The actions of relaxin (mostly 1 and 2) include an ability to inhibit myometrial contractions, stimulation of remodelling of connective tissue and induction of softening of the tissues of the cervix and birth canal. Additionally, relaxin (1, 2) increases growth and differentiation of the mammary gland and nipple and induces the breakdown of collagen (mostly by induction of MMP proteins that breakdown ECM components such as collagen as well as inhibition of TIMP proteins which induce ECM, such as collagen, synthesis), one of the main components of connective tissue as well as fibrotic tissues. Relaxin decreases collagen synthesis and increases the release of collagenases. Female mice lacking a functionally active relaxin gene failed to relax and elongate the interpubic ligament of the pubic symphysis and could not suckle their pups, which in turn, died within 24 hours unless crossfostered to relaxin wild type or relaxin heterozygous foster mothers.

Relaxin (1 and 2) has additionally been reported to cause a widening of blood vessels (vasodilatation) in the kidney, mesocaecum, lung and peripheral vasculature, which leads to increased blood flow or perfusion rates in these tissues. It also stimulates an increase in heart rate and coronary blood flow, and increases both glomerular filtration rate and renal plasma flow. Relaxin (1,2) has also been found to inhibit histamine release and the accumulation of calcium, as well as promote nitric oxide synthesis, during cardiac anaphylaxis.

The brain is another target tissue for relaxin where the peptides have been shown to bind to receptors in the circumventricular organs to affect blood pressure, food intake and drinking Relaxin (1 and 2) has also been implicated in depression of platelet aggregation and their release by megakaryocytes, and may thus be associated with clotting disorders.

The INSL peptides, such as INSL3, has been shown to be involved in maturation and descent of the testes, as well as the survival of sperm cells, development of ovarian follicles and maturation of the oocyte. Therefore, potential clinical applications of INSL3 agonists and antagonists include the treatment of fertility disorders, or the control of fertility levels.

INSL3 has been implicated in regulation of relaxin activity in the heart. Thus, INL3 agonists of the invention can are useful for treating heart disease. Furthermore, INSL3 polymorphisms have been hyperplastic and neoplastic disorders of the thyroid gland, suggesting a role for this relaxin superfamily member in the etiology of these pathologies.

Provided by the invention are bioactive peptides falling within Formula I.

Formula I includes compounds falling within the following formula:

Wherein $X^1$ is absent or G or a small naturally or non-naturally occurring amino acid;

$X^2$ is absent or Q or a polar naturally or non-naturally occurring amino acid;

$X^3$ is absent or K or a basic naturally or non-naturally occurring amino acid;

$X^4$ is absent or G or a small naturally or non-naturally occurring amino acid;

$X^5$ is absent or Q or S a polar naturally or non-naturally occurring amino acid;

$X^6$ is absent or V or A or P or M or a hydrophobic naturally or non-naturally occurring amino acid;

$X^7$ is absent or G or a small naturally or non-naturally occurring amino acid;

$X^8$ is absent or P or L or A naturally or non-naturally occurring amino acid;

$X^9$ is absent or P or Q naturally or non-naturally occurring amino acid;

$X^{10}$ is absent or G or a small naturally or non-naturally occurring amino acid;

$X^{11}$ is absent or A or H or E or D or a hydrophobic or a small or an acidic naturally or non-naturally occurring amino acid;

$X^{12}$ is absent or A or P or Q or S or R or H or a hydrophobic or a small naturally or non-naturally occurring amino acid;

$X^{13}$ is absent or C or V or a hydrophobic naturally or non-naturally occurring amino acid;

$X^{14}$ is absent or R or K or Q or P or a basic or a polar naturally or non-naturally occurring amino acid;

$X^{15}$ is absent or R or Q or S or a basic or a polar naturally or non-naturally occurring amino acid;

$X^{16}$ is absent or A or L or H or Q or a hydrophobic or a small naturally or non-naturally occurring amino acid;

$X^{17}$ is absent or Y or a hydrophobic or an aromatic naturally or non-naturally occurring amino acid;

$X^{18}$ is absent or A or a hydrophobic or small naturally or non-naturally occurring amino acid;

$X^{19}$ is absent or A or a hydrophobic small naturally or non-naturally occurring amino acid;

$X^{20}$ is absent or F or a hydrophobic or an aromatic naturally or non-naturally occurring amino acid;

$X^{21}$ is absent or S or T or a polar naturally or non-naturally occurring amino acid;

$X^{22}$ is absent or V or a hydrophobic naturally or non-naturally occurring amino acid;

$X^{23}$ is absent or G or hydrophobic or small naturally or non-naturally occurring amino acid or replaced by an Amide;

$X^{24}$ is absent or R or a basic naturally or non-naturally occurring amino acid;

$X^{25}$ is absent or R or a basic naturally or non-naturally occurring amino acid;

$X^{26}$ is A or a hydrophobic or small naturally or non-naturally occurring amino acid;

$X^{27}$ is Y or a hydrophobic or an aromatic naturally or non-naturally occurring amino acid;

$X^{28}$ is A or a hydrophobic or small naturally or non-naturally occurring amino acid;

$X^{29}$ is A or a hydrophobic or small naturally or non-naturally occurring amino acid;

$X^{30}$ is F or a hydrophobic naturally or non-naturally occurring amino acid;

$X^{31}$ is S or T or a polar naturally or non-naturally occurring amino acid;

$X^{32}$ is V or a hydrophobic naturally or non-naturally occurring amino acid;

$X^{33}$ is absent or G or hydrophobic or small naturally or non-naturally occurring amino acid or replaced by an Amide;

or a pharmaceutically acceptable salt thereof.

In some embodiments, a peptide of Formula I includes the amino acid sequence of one of the following:

Peptide P59-S-Amide (Amide):
(SEQ ID NO: 1)
AYAAFSV-Amide;

-continued

Peptide P59-SG (free acid Gly)
(SEQ ID NO: 2)
AYAAFSV;

Peptide P59-Amide (amide)
(SEQ ID NO: 3)
GQKGQVGPPGAACRRAYAAFSV-Amide;

Peptide P59 (free acid)
(SEQ ID NO: 4)
GQKGQVGPPGAACRRAYAAFSV;

Peptide P59C13V-Amide (amide)
(SEQ ID NO: 5)
GQKGQVGPPGAAVRRAYAAFSV-Amide

Peptide P59C13V (free acid)
(SEQ ID NO: 6)
GQKGQVGPPGAAVRRAYAAFSV;

Peptide P74-Amide (Amide):
(SEQ ID NO: 7)
GQKGQVGPPGAACRRAYAAFSVGRRAYAAFSV-Amide Peptide P74 (free acid)
(SEQ ID NO: 8)
GQKGQVGPPGAACRRAYAAFSVGRRAYAAFSV Peptide P74C13V (amide)
(SEQ ID NO: 9)
GQKGQVGPPGAAVRRAYAAFSVGRRAYAAFSV-Amide Peptide P74C13V (free acid)
(SEQ ID NO: 10)
GQKGQVGPPGAAVRRAYAAFSVGRRAYAAFSV Peptide P59SG (free acid Gly)
(SEQ ID NO: 11)
AYAAFSVG;

Peptide P59-G (free acid Gly)
(SEQ ID NO: 12)
GQKGQVGPPGAACRRAYAAFSVG;

Peptide P59C13V-G (free acid Gly)
(SEQ ID NO: 13)
GQKGQVGPPGAAVRRAYAAFSVG;

Peptide P74-G (free acid Gly)
(SEQ ID NO: 14)
GQKGQVGPPGAACRRAYAAFSVGRRAYAAFSVG

Peptide P74C13V-G (free acid Gly)
(SEQ ID NO: 15)
GQKGQVGPPGAAVRRAYAAFSVGRRAYAAFSVG Peptide P59-Chimpanzee
(SEQ ID NO: 20)
GQKGQVGPPGAACQRAYAAFSVG;

Peptide P59-Orangutan
(SEQ ID NO: 21)
GQKGQVGPPGAPCQRAYAAFSVG;

Peptide P59-Rhesus
(SEQ ID NO: 22)
GQKGQVGPPGAPCQRAYAAFSVG;

Peptide P59-Cow
(SEQ ID NO: 23)
GQKGQAGLPGAQCPRAYAAFSVG;

Peptide P59-Chicken
(SEQ ID NO: 24)
GQKGQPGPQGHSCKQLYAAFSVG;

Peptide P59-C1QTNF1 (Human)
(SEQ ID NO: 25)
GQKGSMGAPGERCKSHYAAFSVG;

Peptide P59-Rat
(SEQ ID NO: 26)
GQKGSMGAPGDHCKSQYAAFSVG, that are ligands for the relaxin-related GPCRs selected from the group consisting of RXFP1 (LGR7), RXFP2 (LGR8), RXFP3 (GPCR135) and RXFP4 (GPCR142); and/or of the LGR family of GPCRs, selected from a group consisting of but not limited to LRR containing GPCRs: FSHR (LGR1), LHCGR (LGR2), TSHR (LGR3), LGR4, LGR5, LGR6, LGR7 (RXFP1) and LGR8 (RXFP2).

The present invention also encompasses polypeptides encoded by the polynucleotide sequences of the present invention, as well as polypeptides according to the amino acid sequences described herein.

The present invention also encompasses homologues of these polypeptides, such homologues can be at least 50%, at least 55%, at least 60%, at least 65%, at least 70%, at least 75%, at least 80%, at least 85%, at least 85%, at least 90%, at least 95% or more say 100% homologues to the amino acid sequence set forth below, as can be determined using BlastP software of the National Center of Biotechnology Information (NCBI) using default parameters, optionally and preferably including the following: filtering on (this option filters repetitive or low-complexity sequences from the query using the Seg (protein) program), scoring matrix is BLOSUM62 for proteins, word size is 3, E value is 10, gap costs are 11, 1 (initialization and extension). Optionally and preferably, nucleic acid sequence identity/homology is determined with BlastN software of the National Center of Biotechnology Information (NCBI) using default parameters, which preferably include using the DUST filter program, and also preferably include having an E value of 10, filtering low complexity sequences and a word size of 11. Finally the present invention also encompasses fragments of the above described polypeptides and polypeptides having mutations, such as deletions, insertions or substitutions of one or more amino acids, either naturally occurring or artificially induced, either randomly or in a targeted fashion.

The term "homolog" relating to a peptide of the invention as used herein should be understood to encompass a peptide which has substantially the same amino acid sequence and substantially the same biological activity as peptides depicted in SEQ ID NOs: 1-15, 20-26. Thus, a homolog may differ from the peptides depicted in SEQ ID NOs: 1-15, 20-26 by the addition, deletion or substitution of one or more amino acid residues, provided that the resulting peptide retains the biological activity of peptides depicted in SEQ ID NOs: 1-15, 20-26, respectively. Persons skilled in the art can readily determine which amino acid residues may be added, deleted or substituted (including with which amino acids such substitutions may be made) using established well known procedures. Examples of homologs of peptides depicted in SEQ ID NOs: 1-15, 20-26 are deletion homologs containing less than all the amino acid residues of peptides depicted in SEQ ID NOs: 1-15, 20-26, respectively, substitution homologs wherein one or more amino acid residues specified are replaced by other amino acid residues (eg. amino acid with similar properties or by D-amino acids, or by non-natural amino acids) and addition homologs wherein one or more amino acid residues are added to a terminal or medial portion of peptides depicted in SEQ ID NOs: 1-15, 20-26, respectively.

The term "derivative" relating to a peptide of the invention should be understood to encompass a peptide which has substantially the same amino acid sequence and substantially the same biological activity as peptides depicted in SEQ ID NOs: 1-15, 20-26, respectively. Thus, a derivative may differ from the peptides depicted in SEQ ID NOs: 1-15, 20-26 by a modification, such as but not limited to glycosylation, amidation, acetylation, alkylation, alkenylation, alkynylation, phosphorylation, sulphorization, hydroxylation, hydrogenation and so forth. Thus, a derivative of a peptide of the invention may differ from the peptides depicted in SEQ ID NOs: 1-15, 20-26 by a modification on one or more amino acid residues, provided that the resulting peptide retains the biological activity of peptides depicted in SEQ ID NOs: 1-15, 20-26, respectively. Persons skilled in the art can readily determine which amino acid residues may be modified using established well known procedures. In one embodiment, a peptide of the invention is amidated at its C-terminus and acetylated at its N-terminus.

By "variant" is meant a polypeptide that differs from a reference polypeptide, but retains essential properties. Generally, differences are limited so that the sequences of the reference polypeptide and the variant are closely similar overall and, in many regions, identical. A variant and reference polypeptide may differ in amino acid sequence by one or more substitutions, additions, and/or deletions, in any combination. A substituted or inserted amino acid residue may or may not be one encoded by the genetic code. A variant of a polypeptide may be a naturally occurring such as an allelic variant, or it may be a variant that is not known to occur naturally. Non-naturally occurring variants of polypeptides may be made by mutagenesis techniques or by direct synthesis.

Generally, the variant differs from the reference polypeptide by conservative amino acid substitutions, whereby a residue is substituted by another with like characteristics (e.g. acidic, basic, aromatic, etc.). Typical substitutions are among Ala, Val, Leu and Ile; among Ser and Thr; among the acidic residues Asp and Glu; among Asn and Gln; and among the basic residues Lys and Arg; or aromatic residues Phe and Tyr.

"A peptide with substantially the same biological activity" as used herein should be understood to encompass a peptide which has at least has at least one-forth, e.g., one third, one half, or the same activity, as the activity of a peptide of substantially identical length with a naturally occurring amino acid sequence. By "substantially identical length" is meant the same length or a difference in length of no more than ten percent.

A peptide within Formula I can be provided as part of a longer peptide that includes the specified amino acid sequence. For example, the peptide can be provided on a peptide that is less than 200, 150, 125, 100, 75, 50, 25, 24, 23, 22, 21, 20, 19, 18, 17, 16, 15, 14, 13, 13, 11, 10, 9, 8 or 7 amino acids.

In preferred embodiments, the peptide fragment retains one or more of the activities associated with the full-length peptide, e.g., binding to and/or activation of a GPCR receptor, or activity against a condition described herein. In some embodiments, a peptide within Formula I binds a G-protein coupled receptor (GPCR) protein, which is preferably relaxin-related GPCR or LGR family GPCR. In a further preferred embodiments the relaxin-related GPCR is selected from the group consisting of but not limited to RXFP1, RXFP2, RXFP3 or RXFP4. or from the LGR related family group consisting of but not limited to FSHR (LGR1), LHCGR (LGR2), TSHR (LGR3), LGR4, LGR5, LGR6 LGR7 (RXFP1) and/or LGR8 (RXFP2) proteins.

In some embodiments, a peptide within Formula I activates a GPCR protein. Activation of a GPCR protein can be measured using methods known in the art.

A peptide within Formula I can be provided conjugated to a second peptide or polypeptide. Examples of second peptides or polypeptides are multiple antigenic peptides (MAP) and a signal sequence. Suitable signal sequences include, e.g. MAAPALLLLALLLPVGA (SEQ ID NO:16), MAAPALLLLALLLPVGAWP (SEQ ID NO:17), MAAPALLLLALLLPVGAWPGLP (SEQ ID NO:18).

In some embodiments, the second peptide or polypeptide is an immunoglobulin sequence (e.g., an IgG sequence). Immunoreactive ligands for use as a targeting moiety in the invention include an antigen-recognizing immunoglobulin (also referred to as "antibody"), or antigen-recognizing fragment thereof, e.g., immunoglobulins that can recognize a tumor-associated antigen. As used herein, "immunoglobulin" refers to any recognized class or subclass of immunoglobulins such as IgG, IgA, IgM, IgD, or IgE.

Preferred are those immunoglobulins which fall within the IgG class of immunoglobulins. The immunoglobulin can be derived from any species. Preferably, however, the immunoglobulin is of human, murine, or rabbit origin. In addition, the immunoglobulin may be polyclonal or monoclonal, but is preferably monoclonal.

Conjugates of the invention may include an antigen-recognizing immunoglobulin fragment. Such immunoglobulin fragments may include, for example, the Fab', F (ab')2, Fv or Fab fragments, or other antigen-recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See Parham, *J. Immunology*, 131, 2895, 1983; Lamoyi et al., *J. Immunological Methods*, 56,235, 1983.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. The terms encompass any peptide (including cyclic peptides) or protein comprising two or more amino acids joined to each other by peptide bonds or modified peptide bonds. "Polypeptide" refers to both short chains, commonly referred to as peptides, oligopeptides or oligomers, and to longer chains, generally referred to as proteins.

"Polypeptides" include amino acid sequences modified either by natural processes, or by chemical modification techniques which are well known in the art. Modifications may occur anywhere in a polypeptide, including the peptide backbone, the amino acid side-chains, and the amino or carboxyl termini. Polypeptides can be modified, e.g., by the addition of carbohydrate residues to form glycoproteins. The terms "polypeptide," "peptide" and "protein" include glycoproteins, as well as non-glycoproteins.

Peptides within the invention can be produced using methods known in the art, e.g., by purifying the peptide sequence from a naturally occurring protein or peptide. Purification can be performed along with a cleavage or degradation (either enzymatic or non-enzymatic) to produce the desired peptide using methods known in the art.

Alternatively, products can be biochemically synthesized using, e.g., solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence).

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

Polypeptides or peptides can alternatively be synthesized using recombinant techniques such as those described by Bitter et al., (1987) *Methods in Enzymol.* 153:516-544, Studier et al. (1990) *Methods in Enzymol.* 185:60-89, Brisson et al. (1984) *Nature* 310:511-514, Takamatsu et al. (1987) *EMBO J.* 6:307-311, Coruzzi et al. (1984) *EMBO J.* 3:1671-1680 and Brogli et al., (1984) *Science* 224:838-843, Gurley et al. (1986) *Mol. Cell. Biol.* 6:559-565 and Weissbach & Weissbach, 1988, *Methods for Plant Molecular Biology*, Academic Press, NY, Section VIII, pp 421-463.

A peptide within the invention may include one or more modifications. For example, it may be provided phosphorylated (typically at a serine, threonine, or tyrosine residue), pegylated, coupled to a biotin moiety, or include a disulfide bond to another peptide, polypeptide or amino acid. The peptide may be provided in a cyclic form, e.g., as a cyclic peptide or as a lactam. Alternatively, or in addition, the peptide may be provided as a branched peptide.

The peptide may be additionally modified (when linear) at its amino terminus or carboxy terminus. Examples of amino terminal modifications include, e.g., N-glycated, N-alkylated, N-acetylated or N-acylated amino acid. A terminal modification can include a pegylation. An example of a carboxy terminal modification is a c-terminal amidated amino acid.

A peptide of the invention may contain amino acids other than the 20 gene-encoded amino acids. When amino acids are not designated as either D- or L-amino acids, the amino acid is either an L-amino acid or could be either a D- or L-amino acid, unless the context requires a particular isomer.

The notations used herein for the polypeptide amino acid residues are those abbreviations commonly used in the art. The less common abbreviations Abu, Cpa, Nle, Pal, Tle, Dip, 4-Fpa, and Nal stand for 2-amino-butyric acid, p-chloroPhenylalanine, norleucine, 3-pyridyl-2-alanine, tert-leucine, 2,2-diphenylalanine, 4-fluoro-phenylalanine, and 3-(2-naphthyl)-alanine or 3-(1-naphthyl)-alanine, respectively.

One example of a non-naturally occurring amino acid is an omega-amino acid, e.g., beta-alanine (beta-Ala), or 3 aminopropionic (3-aP). Other examples are non-naturally occurring amino acids, e.g., sarcosine (Sar), β-alanine (β-Ala), 2,3 diaminopropionic (2,3-diaP) or alpha-aminisobutyric acid (Aib); omega-acid is beta-alanine (beta-Ala), or 3 aminopropionic (3-aP); a hydrophobic non-naturally occurring amino acid, such as t-butylalanine (t BuA), t butylglycine (t BuG), N methylisoleucine (N MeIle), norleucine (Nle), methylvaline (Mvl), cyclohexylalanine (Cha), phenylglycine (Phg), NaI, β2-thienylalanine (Thi), 2 naphthylalanine (2 Nal), or 1,2,3, 4-tetrahydroisoquinoline-3 carboxylic acid (Tic); a basic amino acid, such as ornithine (Orn) or homoarginine (Har); and a neutral/polar non-naturally occurring amino acid is citrulline (Cit), Acetyl Lys, or methionine sulfoxide (MSO).

Other non-conventional amino acids are listed in Table 6.

TABLE 6

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |

TABLE 6-continued

| Non-conventional amino acid | Code | Non-conventional amino acid | Code |
|---|---|---|---|
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval nbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Modifications
Fusion Proteins

A fusion protein may be prepared from a peptide according to the present invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG I subtype is preferred. The Fc chain may optionally be a known or "wild type" Fc chain, or alternatively may be mutated. Non-limiting, illustrative, exemplary types of mutations are described in US Patent Application No. 20060034852, published on Feb. 16, 2006, hereby incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat E A et al: Sequences of Proteins of Immunological Interest. US Department of Health and Human Services, NIH, 1991): 220C→S; 233-238 ELLGGP→EAEGAP; 265D→A, preferably in combination with 434N→A; 297N→A (for example to block N-glycosylation); 318-322 EYKCK→AYACA; 330-331AP→SS; or a combination thereof (see for example M. Clark, "Chemical Immunol and Antibody Engineering", pp 1-31 for a description of these mutations and their effect). The construct for the Fc chain which features the above changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331proline for serine may block the ability to activate complement, which may optionally be considered an undesired function (see M. Clark, "Chemical Immunol and Antibody Engineering", pp 1-31). Changing 330alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to a serine, to avoid any type of covalent linkage (see M. Clark, "Chemical Immunol and Antibody Engineering", pp 1-31).

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al. vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

Addition of Groups

If a peptide according to the present invention is a linear molecule, it is possible to place various functional groups at various points on the linear molecule which are susceptible to or suitable for chemical modification. Functional groups can be added to the termini of linear forms of the peptide. In some embodiments, the functional groups improve the activity of the peptide with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —$NH_2$, —$NHR_2$ and —$NR_2R_3$) or ester (i.e. the hydroxyl group at the C-terminus is replaced with —$OR_2$). $R_2$ and $R_3$ are optionally independently an aliphatic, substituted aliphatic, benzyl, substituted benzyl, aryl or a substituted aryl group. In addition, taken together with the nitrogen atom, $R_2$ and $R_3$ can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —$NH_2$, —$NHCH_3$, —$N(CH_3)_2$, —NH(ethyl), —N(ethyl)$_2$, —N(methyl)(ethyl), —NH(benzyl), —N(C1-C4 alkyl)(benzyl), —NH(phenyl), —N(C1-C4 alkyl)(phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native peptide protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett. (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

Chemical Modifications

In the present invention any part of a peptide may optionally be chemically modified, i.e. changed by addition of functional groups. For example the side amino acid residues appearing in the native sequence may optionally be modified, although as described below alternatively other part(s) of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Covalent modifications of the peptides of the present invention are included within the scope of this invention. Other types of covalent modifications of the peptides are introduced into the molecule by reacting targeted amino acid residues with an organic derivatizing agent that is capable of reacting with selected side chains or the N- or C-terminal residues.

Cysteinyl residues most commonly are reacted with $\alpha$-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, $\alpha$-bromo-$\beta$-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing $\alpha$-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125 I or 131 I to prepare labeled proteins for use in radioimmunoassay, the chloramine T method described above being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking CHF to a water-insoluble support matrix or surface for use in the method for purifying anti-CHF antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the $\alpha$-amino groups of lysine, arginine, and histidine side chains (T. E. Creighton, Proteins: Structure and Molecular Properties, W. H. Freeman & Co., San Francisco, pp. 79-86 [1983]), acetylation of the N-terminal amine, and amidation of any C-terminal carboxyl group.

Altered Glycosylation

Peptides of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to peptides of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on peptides of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Antibodies to Bioactive Peptides

The invention also includes an antibody to a bioactive peptide disclosed herein, or a fragment of the bioactive peptide. In some embodiments, the bioactive peptide is a GPCR ligand.

"Antibody" refers to a polypeptide ligand substantially encoded by an immunoglobulin gene or immunoglobulin genes, or fragments thereof, which specifically binds and recognizes an epitope (e.g., an antigen). The antibody can be provided as, e.g., an intact immunoglobulin or as fragment, e.g., a fragment produced by digestion with various peptidases. This includes, e.g., Fab' and F(ab)'₂ Fv (defined as a genetically engineered fragment containing the variable region of the light chain and the variable region of the heavy chain expressed as two chains); and (5) Single chain antibody ("SCA"), a genetically engineered molecule containing the variable region of the light chain and the variable region of the heavy chain, linked by a suitable polypeptide linker as a genetically fused single chain molecule. The term "antibody," as used herein, also includes antibody fragments either produced by the modification of whole antibodies or those synthesized de novo using recombinant DNA methodologies. It includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

Antibodies are raised against, e.g., an epitope in a peptide of Formula I. In some embodiments, anti-GPCR peptide ligand antibodies are raised against Peptide P59-S-Amide (Amide):
(SEQ ID NO: 1)
AYAAFSV-Amide;

Peptide P59-SG (free acid Gly)
(SEQ ID NO: 2)
AYAAFSV;

Peptide P59-Amide (amide)
(SEQ ID NO: 3)
GQKGQVGPPGAACRRAYAAFSV-Amide;

Peptide P59 (free acid)
(SEQ ID NO: 4)
GQKGQVGPPGAACRRAYAAFSV;

Peptide P59C13V-Amide (amide)
(SEQ ID NO: 5)
GQKGQVGPPGAAVRRAYAAFSV-Amide

Peptide P59C13V (free acid)
(SEQ ID NO: 6)
GQKGQVGPPGAAVRRAYAAFSV;

Peptide P74-Amide (Amide):
(SEQ ID NO: 7)
GQKGQVGPPGAACRRAYAAFSVGRRAYAAFSV-Amide Peptide P74 (free acid)
(SEQ ID NO: 8)
GQKGQVGPPGAACRRAYAAFSVGRRAYAAFSV Peptide P74C13V (amide)
(SEQ ID NO: 9)
GQKGQVGPPGAAVRRAYAAFSVGRRAYAAFSV-Amide Peptide P74C13V (free acid)
(SEQ ID NO: 10)
GQKGQVGPPGAAVRRAYAAFSVGRRAYAAFSV Peptide P59SG (free acid Gly)
(SEQ ID NO: 11)
AYAAFSVG;

Peptide P59-G (free acid Gly)
(SEQ ID NO: 12)
GQKGQVGPPGAACRRAYAAFSVG;

Peptide P59C13V-G (free acid Gly)
(SEQ ID NO: 13)
GQKGQVGPPGAAVRRAYAAFSVG;

Peptide P74-G (free acid Gly)
(SEQ ID NO: 14)
GQKGQVGPPGAACRRAYAAFSVGRRAYAAFSVG

Peptide P74C13V-G (free acid Gly)
(SEQ ID NO: 15)
GQKGQVGPPGAAVRRAYAAFSVGRRAYAAFSVG Peptide P59-Chimpanzee
(SEQ ID NO: 20)
GQKGQVGPPGAACQRAYAAFSVG;

Peptide P59-Orangutan
(SEQ ID NO: 21)
GQKGQVGPPGAPCQRAYAAFSVG;

Peptide P59-Rhesus
(SEQ ID NO: 22)
GQKGQVGPPGAPCQRAYAAFSVG;

Peptide P59-Cow
(SEQ ID NO: 23)
GQKGQAGLPGAQCPRAYAAFSVG;

Peptide P59-Chicken
(SEQ ID NO: 24)
GQKGQPGPQGHSCKQLYAAFSVG;

Peptide P59-C1QTNF1 (Human)
(SEQ ID NO: 25)
GQKGSMGAPGERCKSHYAAFSVG;

Peptide P59-Rat
(SEQ ID NO: 26)
GQKGSMGAPGDHCKSQYAAFSVG.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods.

The bioactive peptide antibody can additionally be provided as a peptide coding corresponding a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [*Methods*, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321: 522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., *Nature*, 321:522-525 (1986); Riechmann et al., *Nature* 332:323-327 (1988); Verhoeyen et al., *Science*, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10,: 779-783 (1992); Lonberg et al., *Nature* 368: 856-859 (1994); Morrison, *Nature* 368 812-13 (1994); Fishwild et al., *Nature Biotechnology* 14, 845-51 (1996); Neuberger, *Nature Biotechnology* 14: 826 (1996); and Lonberg and Huszar, *Intern. Rev. Immunol.* 13, 65-93 (1995).

The antibody preferably binds specifically (or selectively) to a GPCR peptide ligand. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

If desired, the antibody can be provided conjugated or coupled to a detectable label, a radioactive label, an enzyme, a fluorescent label, a luminescent label, a bioluminescent label, or a therapeutic agent.

Methods of Treatment

According to an additional aspect of the present invention there is provided a method of treating disease, disorder or condition, as described hereinabove, in a subject.

The subject according to the present invention is a mammal, preferably a human which is diagnosed with one of the disease, disorder or conditions described hereinabove, or alternatively is predisposed to at least one type of disease, disorder or conditions described hereinabove.

As used herein the term "treating" refers to preventing, curing, reversing, attenuating, alleviating, minimizing, suppressing or halting the deleterious effects of the above-described diseases, disorders or conditions.

Treating, according to the present invention, can be effected by specifically upregulating the expression of at least one of the polypeptides of the present invention in the subject.

Optionally, upregulation may be effected by administering to the subject at least one of the polypeptides of the present invention (e.g., recombinant or synthetic) or an active portion thereof, as described herein. The polypeptide or peptide may optionally be administered in as part of a pharmaceutical composition, described in more detail below.

It will be appreciated that treatment of the above-described diseases according to the present invention may be combined with other treatment methods known in the art (i.e., combination therapy). Thus, treatment of malignancies using the agents of the present invention may be combined with, for example, radiation therapy, antibody therapy and/or chemotherapy, surgery or in combination therapy with other biological agents, conventional drugs and/or with any other anticancer agent, such as immunosuppressants or cytotoxic drugs for cancer, and or in combination with therapeutic agents targeting complement regulatory proteins (CRPs). Each one of the above mentioned compounds or pharmaceutical composition of the invention may also be administered in conjunction with other compounds. For example, the combination therapy can include the compound of the present invention combined with at least one other therapeutic or immune modulatory agent, including, but not limited to, chemotherapeutic agents such as cytotoxic and cytostatic agents, immunological modifiers such as interferons and interleukins, growth hormones or other cytokines, folic acid, vitamins, minerals, aromatase inhibitors, RNAi, Histone Deacetylase Inhibitors, proteasome inhibitors, and so forth.

Alternatively or additionally, an upregulating method may optionally be effected by specifically upregulating the amount (optionally expression) in the subject of at least one of the polypeptides of the present invention or active portions thereof.

Upregulating expression of the therapeutic peptides of the present invention may be effected via the administration of at least one of the exogenous polynucleotide sequences of the present invention, ligated into a nucleic acid expression construct designed for expression of coding sequences in eukaryotic cells (e.g., mammalian cells). Accordingly, the exogenous polynucleotide sequence may be a DNA or RNA sequence encoding the peptides of the present invention or active portions thereof.

It will be appreciated that the nucleic acid construct can be administered to the individual employing any suitable mode of administration including in vivo gene therapy (e.g., using viral transformation as described hereinabove). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

Such cells (i.e., which are transfected with the nucleic acid construct of the present invention) can be any suitable cells, such as kidney, bone marrow, keratinocyte, lymphocyte, adult stem cells, cord blood cells, embryonic stem cells which are derived from the individual and are transfected ex vivo with an expression vector containing the polynucleotide designed to express the polypeptide of the present invention as described hereinabove.

Administration of the ex vivo transfected cells of the present invention can be effected using any suitable route such as intravenous, intra peritoneal, intra kidney, intra gastrointestinal track, subcutaneous, transcutaneous, intramuscular, intracutaneous, intrathecal, epidural and rectal. According to presently preferred embodiments, the ex vivo transfected cells of the present invention are introduced to the individual using intravenous, intra kidney, intra gastrointestinal track and/or intra peritoneal administrations.

The ex vivo transfected cells of the present invention can be derived from either autologous sources such as self bone marrow cells or from allogeneic sources such as bone marrow or other cells derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly (allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

Pharmaceutical Compositions and Delivery Thereof

The bioactive peptide ligand is typically provided in a pharmaceutically acceptable carrier suitable for administering the pharmaceutical composition to a human patient. As would be appreciated by one of skill in this art, the carriers may be chosen based on the route of administration as described below, the location of the target issue, the drug being delivered, the time course of delivery of the drug, etc.

The term "pharmaceutically acceptable carrier" means a non-toxic, inert solid, semi-solid or liquid filler, diluent, encapsulating material or formulation auxiliary of any type. One exemplary pharmaceutically acceptable carrier is physiological saline. Other physiologically acceptable carriers and their formulations are known to one skilled in the art and described, for example, in Remington's Pharmaceutical Sciences, (18$^{th}$ edition), A. Gennaro, 1990, Mack Publishing Company, Easton, Pa. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate;

agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

By "pharmaceutically acceptable salt" is meant non-toxic acid addition salts or metal complexes which are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like.

The pharmaceutical compositions can be administered to a patient by any means known in the art including oral and parenteral routes. The term "patient", as used herein, refers to humans as well as non-humans, including, for example, mammals, birds, reptiles, amphibians and fish. Preferably, the non-humans are mammals (e.g., a rodent (including a mouse or rat), a rabbit, a monkey, a dog, a cat, sheep, cow, pig, horse). The non-human animal could alternatively be a bird, e.g., a chicken or turkey.

In certain embodiments parenteral routes are preferred since they avoid contact with the digestive enzymes that are found in the alimentary canal. According to such embodiments, inventive compositions including a therapeutic agent may be administered by injection (e.g., intravenous, subcutaneous or intramuscular, intraperitoneal injection), rectally, vaginally, topically (as by powders, creams, ointments, or drops), or by inhalation (as by sprays), intranasal, pulmonary, or intrabuccal.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In a particularly preferred embodiment, a therapeutic agent is suspended in a carrier fluid comprising 1% (w/v) sodium carboxymethyl cellulose and 0.1% (v/v) TWEEN80™. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the therapeutic agent with suitable non-irritating excipients or carriers such as cocoa butter, polyethylene glycol, or a suppository wax which are solid at ambient temperature but liquid at body temperature and therefore melt in the rectum or vaginal cavity and release the therapeutic agent.

Dosage forms for topical or transdermal administration of a pharmaceutical composition including a therapeutic agent include ointments, pastes, creams, lotions, gels, powders, solutions, sprays, inhalants, or patches. The therapeutic agent is admixed under sterile conditions with a pharmaceutically acceptable carrier and any needed preservatives or buffers as may be required. Ophthalmic formulations, ear drops and eye drops are also contemplated as being within the scope of this invention. The ointments, pastes, creams and gels may contain, in addition to the therapeutic agents of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Transdermal patches have the added advantage of providing controlled delivery of a compound to the body. Such dosage forms can be made by dissolving or dispensing the therapeutic agents in a proper medium. Absorption enhancers can also be used to increase the flux of the compound across the skin. The rate can be controlled by either providing a rate controlling membrane or by dispersing the therapeutic agents in a polymer matrix or gel.

Powders and sprays can also contain excipients such as lactose, talc, silicic acid, aluminum hydroxide, calcium silicates and polyamide powder, or mixtures of these drugs. Sprays can additionally contain customary propellants such as chlorofluorohydrocarbons.

When administered orally, the therapeutic agent is optionally encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al., Reactive Polymers 6:275, 1987; Mathiowitz et al., J. Appl. Polymer Sci. 35:755, 1988; Langer Acc. Chem. Res. 33:94, 2000; Langer J. Control. Release 62:7, 1999; Uhrich et al., Chem. Rev. 99:3181, 1999; Zhou et al., J. Control. Release 75:27, 2001; and Hanes et al., Pharm. Biotechnol. 6:389, 1995). For example, the therapeutic agent can be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters) and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides and gangliosides.

Pharmaceutical compositions for oral administration can be liquid or solid. Liquid dosage forms suitable for oral administration of inventive compositions include pharmaceutically acceptable emulsions, microemulsions, solutions, suspensions, syrups and elixirs. In addition to an encapsulated or unencapsulated therapeutic agent, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions can also include adjuvants, wetting agents, emulsifying and suspending agents, sweetening, flavoring and perfuming agents. As used herein, the term "adjuvant" refers to any compound which is a nonspecific modulator of the immune response. In certain preferred embodiments, the adjuvant stimulates the immune response. Any adjuvant may be used in accordance with the present invention. A large number of adjuvant compounds are known in the art (Allison, *Dev. Biol. Stand.* 92:3, 1998; Unkeless et al., *Annu. Rev. Immunol.* 6:251, 1998; and Phillips et al., *Vaccine* 10: 151, 1992).

Solid dosage forms for oral administration include capsules, tablets, pills, powders and granules. In such solid dosage forms, the encapsulated or unencapsulated therapeutic agent is mixed with at least one inert, pharmaceutically acceptable excipient or carrier such as sodium citrate or dicalcium phosphate and/or (a) fillers or extenders such as starches, lactose, sucrose, glucose, mannitol and silicic acid, (b) binders such as, for example, carboxymethylcellulose, alginates, gelatin, polyvinylpyrrolidinone, sucrose and acacia, (c) humectants such as glycerol, (d) disintegrating agents such as agar-agar, calcium carbonate, potato or tapioca starch, alginic acid, certain silicates and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well known in the pharmaceutical formulating art.

The exact dosage of the therapeutic agent is chosen by the individual physician in view of the patient to be treated. In general, dosage and administration are adjusted to provide an effective amount of the therapeutic agent to the patient being treated. As used herein, the "effective amount" of an therapeutic agent refers to the amount necessary to elicit the desired biological response. As will be appreciated by those of ordinary skill in this art, the effective amount of therapeutic agent may vary depending on such factors as the desired biological endpoint, the drug to be delivered, the target tissue, the route of administration, etc. For example, the effective amount of therapeutic agent containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy. Long acting pharmaceutical compositions might be administered every 3 to 4 days, every week, or once every two weeks depending on half-life and clearance rate of the particular composition.

The therapeutic agents of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compositions of the present invention will be decided by the attending physician within the scope of sound medical judgment.

For any therapeutic agent, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of therapeutic agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies is used in formulating a range of dosage for human use.

If several different therapeutic modalities (e.g., with different therapeutic agents) are to be administered simultaneously then they may be combined into a single pharmaceutical composition. Alternatively, they may be prepared as separate compositions that are then mixed or simply administered one after the other. If several different therapeutic agents (e.g., with different therapeutic agents) are to be administered at different times then they are preferably prepared as separate compositions. If additional drugs are going to be included in a combination therapy they can be added to one or more of these therapeutic agents or prepared as separate compositions.

A peptide could be chemically modified in order to alter its properties such as biodistribution, pharmacokinetics and solubility. Various methods have been used to increase the solubility and stability of drugs, among them the use of organic solvents, their incorporation within emulsions or liposomes, the adjustment of pH, their chemical modifications and their complexation with the cyclodextrins. The cyclodextrins are oligosaccharides cyclic family, which include six, seven or eight units of glucopyranose. Due to sterics interactions, the cyclodextrins form a cycle structure in the shape of a cone with an internal cavity. Those are compounds chemically stable that can be modified. The cyclodextrins hosts form complexes with various hydrophobic guests in their cavity. The cyclodextrins are used for the solubilization and encapsulation of drugs.

Liposomes and Controlled Release:

In order to design a drug delivery system, various kinds of high performance carrier materials are being developed to deliver the necessary amount of drug to the targeted site for a necessary period of time, both efficiently and precisely. Cyclodextrins, biodegradable or non biodegradable polymers, liposomes, emulsions. Multiple emulsions are potential candidates for such a role, because of their ability to alter physical, chemical and biological properties of guest molecules.

There are number of drug delivery systems including but not limited to polymer microcapsules, microparticles, nanoparticles, liposomes and emulsion. Many of these are prepared from synthetic biodegradable polymers such as polyanhydrides and poly hydroxy acids. In these systems the drugs incorporate in polymeric microspheres, which release the drug inside the organism in small and controlled daily doses during days months or until years.

Several polymers already were tested in controlled release systems. Such as: polyuretans for its elasticity, polysiloxans or silicons for being a good one insulating, polymethylmetacrilate for its physical form; polyvinilalcohol for its hydrofobicity and resistance, polyethilene for its hardness and impermeability (Gilding, D. K. Biodegradable polymers. Biocompat. Clin. Impl. Mater. 2:209-232, 1981). Biodegradable polymers and biocompatible polymers, have been extensively investigated as vehicle for controlled release systems due to their ability to undergo surface degradation. These kind of polymers can be chose from: poly(2-hidroxi-ethylmetacrilate), polyacrilamide, polymer from lactic acid (PLA), from glicolic acid (PGA), and the respective ones co-polymers, (PLGA) and the poly(anidrides), as described by Tamada and Langer, J. Biomater. Sci. Polym. Edn, 3(4):315-353.

Suitable controlled release vehicles include, but are not limited to, biocompatible polymers, other polymeric matrices, capsules, microcapsules, nanocapsules, microparticles, nanoparticles, bolus preparations, osmotic pumps, diffusion devices, liposomes, liposheres and transdermal delivery systems, implantable or not.

Satisfactory systems of controlled release include, but are not limited to, the ciclodextrines, biocompatible polymers, biodegradable polymers, other polymeric matrixes, capsules, micro-capsules, microparticles, bolus preparations, osmotic pumps, diffusion devices, lipossomes, lipoesferes, and systems of transdermic administration. Other compositions of controlled release include liquids that, when submitted the temperature changes, form a solid or a gel in situ.

Liposomes are lipid vesicles that include aqueous internal compartments in which molecules, for example drugs, are encapsulated with the objective of reaching a controlled release of the drug after administration in individuals. Many different techniques have been proposed for the preparation of liposomes [U.S. Pat. No. 4,552,803, Lenk; U.S. Pat. No. 4,310,506, Baldeschwieler; U.S. Pat. No. 4,235,871, Papahadjopoulos; U.S. Pat. No. 4,224,179, Schneider; U.S. Pat. No. 4,078,052, Papahadjopoulos; U.S. Pat. No. 4,394,372, Tailor; U.S. Pat. No. 4,308,166, Marchetti; U.S. Pat. No. 4,485,054, Mezei; and U.S. Pat. No. 4,508,703, Redziniak; Woodle and Papahadjopoulos, Methods Enzymol. 171:193-215 (1989]. Unilamellar vesicles display a single membrane [Huang, Biochemistry 8:334-352 (1969] while multilamellar vesicles (MLVs) have numerous concentric membranes [Bangham et al., J. Mol. Biol. 13:238-252 (1965]. The procedure of Bangham [J. Mol. Biol. 13:238-252 (1965] produces "ordinary MLVs", that present unequal solute distributions among the aqueous compartments and, consequently, differences of osmotic pressure. Lenk et al. (U.S. Pat. No. 4,522,803; U.S. Pat. No. 5,030,453 and U.S. Pat. No. 5,169,637), Fountain et al. (U.S. Pat. No. 4,588,578), Cullis et al. (U.S. Pat. No. 4,975,282) and Gregoriadis et al. (Pat. W.O. 99/65465) introduced methods for the preparation of MLVs that present substantially equal solute distributions among the compartments. Similar solute distributions among the different compartments mean a larger drug encapsulation efficiency as well as smaller differences of osmotic pressure that turns these MLVs more stable than ordinary MLVs. Unilamellar vesicles can be produced by sonication of MLVs [Papahadjopoulos et al. (1968)] or by extrusion through polycarbonate membranes [Cullis et al. (U.S. Pat. No. 5,008,050) and Loughrey et al. (U.S. Pat. No. 5,059,421)].

Satisfactory lipids include for example, phosphatidylcholine, phosphatidylserine, phosphatidylglycerol, cardiolipin, cholesterol, phosphatidic acid, sphingolipids, glycolipids, fatty acids, sterols, phosphatidylethanolamine, polymerizable lipids in their polymerized or non-polymerized form, mixture of these lipids.

The composition of the liposomes can be manipulated such as to turn them specific for an organ or a cell type. The targeting of liposomes has been classified either on the basis of anatomical factors or on the basis of the mechanism of their interaction with the environment. The anatomical classification is based on their level of selectivity, for example, organ-specific or cell-specific. From the point of view of the mechanisms, the-targeting can be considered as passive or active.

The passive targeting exploits the natural tendency of conventional liposomes to be captured by the cells of the reticulo-endothelial system, i.e. mainly the fixed macrophages in the liver, spleen and bone marrow.

Sterically stabilized liposomes (also well-known as "PEG-liposomes") are characterized by a reduced rate of elimination from the blood circulation [Lasic and Martin, Stealth Liposomes, CRC Press, Inc., Boca Raton, Fla. (1995)].

PEG-liposomes present a polyethylene glycol polymer conjugated to the head group of some phospholipid that reduces their interaction with plasma proteins, such as opsonins, and reduces the rate of their uptake by cells. The resulting steric barrier allows these liposomes to remain for a longer period of time within the circulation than conventional liposomes [Lasic and Martin, Stealth Liposomes, CRC Press, Inc., Boca Raton, Fla. (1995); Woodle et al., Biochim. Biophys. Acta 1105:193-200 (1992); Litzinger et al., Biochim. Biophys. Acta 1190:99-107 (1994); Bedu Addo, et al., Pharm. Res. 13:718-724 (1996]. The drug encapsulation within PEG-liposomes has resulted in the improvement of the effectiveness of many chemotherapeutic agents [Lasic and Martin, Stealth liposomes, CRC Press, Inc., Boca Raton, Fla. (1995)] and bioactive peptides [Allen T. M. In: Liposomes, New Systems, New Trends in their Applications (F. Puisieux, P. Couvreur, J. Delattre, J.-P. Devissaguet Ed.), Editions de la Sante, France, 1995, pp. 125].

Studies in this area demonstrated that different factors affect the effectiveness of PEG-liposomes. Ideally, the diameter of the vesicles should be below 200 nm, the number of units in PEG of approximately 2.000 and the proportion of Pegylated lipid from 3 to 5 mol % [Lasic and Martin, Stealth Liposomes, CRC Press, Inc., Boca Raton, Fla. (1995); Woodle et al., Biochim. Biophys. Acta 1105:193-200 (1992); Litzinger et al., Biochim. Biophys. Acta 1190:99-107 (1994); Bedu Addo et al., Pharm. Res. 13:718-724 (1996)].

The active targeting involves alteration of liposomes through their association with a ligand, such as a monoclonal antibody, a sugar, a glycolipid, protein, a polymer or by changing the lipid composition or the liposome size to target them to organs and cells different from those which accumulate conventional liposomes.

Mucosal Delivery Enhancing Agents

"Mucosal delivery enhancing agents" are defined as chemicals and other excipients that, when added to a formulation comprising water, salts and/or common buffers and peptide within the present invention (the control formulation) produce a formulation that produces a significant increase in transport of peptide across a mucosa as measured by the maximum blood, serum, or cerebral spinal fluid concentration (Cmax) or by the area under the curve, AUC, in a plot of concentration versus time. A mucosa includes the nasal, oral, intestional, buccal, bronchopulmonary, vaginal, and rectal mucosal surfaces and in fact includes all mucus-secreting membranes lining all body cavities or passages that communicate with the exterior. Mucosal delivery enhancing agents are sometimes called carriers.

Compositions and Methods of Sustained Release

The present invention provides improved mucosal (e.g., nasal) delivery of a formulation comprising the peptide within the present invention in combination with one or more mucosal delivery-enhancing agents and an optional sustained release-enhancing agent or agents. Mucosal delivery-enhancing agents of the present invention yield an effective increase in delivery, e.g., an increase in the maximal plasma concentration (Cmax) to enhance the therapeutic activity of mucosally-administered peptide. A second factor affecting therapeutic activity of the peptide in the blood plasma and CNS is residence time (RT). Sustained release-enhancing agents, in combination with intranasal delivery-enhancing agents, increase Cmax and increase residence time (RT) of the peptide. Polymeric delivery vehicles and other agents and methods of the present invention that yield sustained release-enhancing formulations, for example, polyethylene glycol (PEG), are disclosed herein. Within the mucosal delivery formulations and methods of the invention, the peptide is frequently combined or coordinately administered with a suitable carrier or vehicle for mucosal delivery. As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, can be found in the U.S. Pharmacopeia National Formulary, 1857-1859, (1990). As used herein, "mucosal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of the peptide or other biologically active compound(s). Within certain aspects of the invention, absorption-promoting agents for coordinate administration or combinatorial formulation with the peptide of the invention are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium laurylsulfate, oleic acid, and the bile salts, may be employed to enhance mucosal penetration of the peptide. In additional aspects, surfactants (e.g., polysorbates) are employed as adjunct compounds, processing agents, or formulation additives to enhance intranasal delivery of the peptide. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the peptide from the vehicle into the mucosa. The mucosal therapeutic and prophylactic compositions of the present invention may be supplemented with any suitable penetration-promoting agent that facilitates absorption, diffusion, or penetration of the peptide across mucosal barriers. The penetration promoter may be any promoter that is pharmaceutically acceptable.

Charge Modifying and pH Control Agents and Methods

To improve the transport characteristics of biologically active agents (including the peptide within the present invention), for enhanced delivery across hydrophobic mucosal membrane barriers, the invention also provides techniques and reagents for charge modification of selected biologically active agents or delivery-enhancing agents described herein. In this regard, the relative permeabilities of macromolecules is generally be related to their partition coefficients. The degree of ionization of molecules, which is dependent on the pKa of the molecule and the pH at the mucosal membrane surface, also affects permeability of the molecules. Permeation and partitioning of biologically active agents, including the peptide within the present invention, for mucosal delivery may be facilitated by charge alteration or charge spreading of the active agent or permeabilizing agent, which is achieved, for example, by alteration of charged functional groups, by modifying the pH of the delivery vehicle or solution in which the active agent is delivered, or by coordinate administration of a charge- or pH-altering reagent with the active agent. Consistent with these general teachings, mucosal delivery of charged macromolecular species, including the peptide within the present invention is substantially improved when the active agent is delivered to the mucosal surface in a substantially un-ionized, or neutral, electrical charge state.

Certain peptide and protein components of mucosal formulations for use within the invention will be charge modified to yield an increase in the positive charge density of the peptide or protein. These modifications extend also to cationization of peptide and protein conjugates, carriers and other delivery forms disclosed herein.

Degradative Enzyme Inhibitory Agents and Methods

Another excipient that may be included in a trans-mucosal preparation is a degradative enzyme inhibitor. Any inhibitor that inhibits the activity of an enzyme to protect the biologically active agent(s) may be usefully employed in the compositions and methods of the invention. Useful enzyme inhibitors for the protection of biologically active proteins and peptides include, for example, soybean trypsin inhibitor, pancreatic trypsin inhibitor, chymotrypsin inhibitor and trypsin and chrymotrypsin inhibitor isolated from potato (*solanum tuberosum* L.) tubers. A combination or mixtures of inhibitors may be employed. The inhibitor(s) may be incorporated in or bound to a carrier, e.g., a hydrophilic polymer, coated on the surface of the dosage form which is to contact the nasal mucosa, or incorporated in the superficial phase of the surface, in combination with the biologically active agent or in a separately administered (e.g., pre-administered) formulation. Additional enzyme inhibitors for use within the invention are selected from a wide range of non-protein inhibitors that vary in their degree of potency and toxicity. As described in further detail below, immobilization of these adjunct agents to matrices or other delivery vehicles, or development of chemically modified analogues, may be readily implemented to reduce or even eliminate toxic effects, when they are encountered. Among this broad group of candidate enzyme inhibitors for use within the invention are organophosphorous inhibitors, such as diisopropylfluorophosphate (DFP) and phenylmethylsulfonyl fluoride (PMSF), which are potent, irreversible inhibitors of serine proteases (e.g., trypsin and chymotrypsin). Yet another type of enzyme inhibitory agent for use within the methods and compositions of the invention are amino acids and modified amino acids that interfere with enzymatic degradation of specific therapeutic compounds.

The therapeutic agents of the invention can be used to treat disorders for which modulation of GPCR-related signal transduction pathways is efficacious. For example, the peptides of the invention falling within Formula I are used to treat disorders for which modulation or activation of relaxin-related GPCR receptors and/or LGR family of GPCRs responses in a cell or in a subject is efficacious. Examples of such peptides are depicted in SEQ ID NOs: 1-15, 20-26. In another example, the peptide of the invention falling within Formula I are further used to treat any disease or condition that involves agonist associated activation and/or modulation of relaxin or relaxin related peptides activity on relaxin-related family of GPCRs and/or LGR family of GPCRs, either by itself or in combination with relaxin or any relaxin related peptide or another compound, wherein the activation and/or modulation of the receptor can be either by direct activation of downstream pathways directly related to the receptors or to G-proteins activated by the receptors or any other related pathway, or by indirect activation by either relaxin or any relaxin related peptide or another compound. The disorder is selected from but not limited to hyperplastic disorders, neoplastic disorders, cancer; fibrotic conditions, disorders of collagen deposition, fibrotic breakdown, connective tissue remodeling, uncontrolled or abnormal collagen or fibronectin formation or breakdown; skin injuries including wound healing and scarring, scleroderma; urogenital disorders including female reproductive disorders, male and female infertility, cryptorchidism, disregulation of spermatogenesis and reproductive development including descent of the gonads; conditions associated with pregnancy such as preeclampsia or complication of labor; angiogenesis related disorders; cardiovascular disorders, vasodilatation, vasoconstriction or hypertension, endothelial disfunction and vascular disease, congestive heart failure, coronary artery disease, ischemia and ischemia-reperfusion, peripheral vascular disease; kidney disease, renal disease associated with arteriosclerosis or other narrowing of kidney capillaries; capillaries narrowing in the body, such as in the eyes or in the peripheral digits, the mesocaecum, lung and peripheral vasculature; CNS related disorders, neurological disorders, cognition and memory related indications, depression, neurological modification; inflammatory disorders, such as gastritis, gout, gouty arthritis, arthritis, rheumatoid arthritis, inflammatory bowel disease, Crohn's disease, ulcerative colitis, ulcers; autoimmune disorders; inflammatory conditions associated with viral infection and infection related diseases including fibrosis and cirrhosis; Raynaud's disease, Raynaud's phenomenon; bone related conditions including osteoporosis; metabolic disorders including food and water intake, diabetes, obesity; respiratory or a pulmonary disorder, including asthma, COPD, bronchial disease, lung diseases, cystic fibrosis, ARDS, SARS.

In another aspect, the invention provides a method of treating, preventing or ameliorating the symptoms of a relaxin-related GPCR family or LGR family of GPCRs-mediated or related disorders or conditions in a patient, the disorder or condition selected from the group consisting of but not limited to hyperplastic disorders, neoplastic disorders, cancer; fibrotic conditions, disorders of collagen deposition, fibrotic breakdown, connective tissue remodeling, uncontrolled or abnormal collagen or fibronectin formation or breakdown; skin injuries including wound healing and scarring, scleroderma; urogenital disorders including female reproductive disorders, male and female infertility, cryptorchidism, disregulation of spermatogenesis and reproductive development including descent of the gonads; conditions associated with pregnancy such as preeclampsia or complication of labor; angiogenesis related disorders; cardiovascular disorders, vasodilatation, vasoconstriction or hypertension, endothelial disfunction and vascular disease, congestive heart failure, coronary artery disease, ischemia and ischemia-reperfusion, peripheral vascular disease; kidney disease, renal disease associated with arteriosclerosis or other narrowing of kidney capillaries; capillaries narrowing in the body, such as in the eyes or in the peripheral digits, the mesocaecum, lung and peripheral vasculature; CNS related disorders, neurological disorders, cognition and memory related indications, depression, neurological modification; inflammatory disorders, such as gastritis, gout, gouty arthritis, arthritis, rheumatoid arthritis, inflammatory bowel disease, Crohn's disease, ulcerative colitis, ulcers; autoimmune disorders; inflammatory conditions associated with viral infection and infection related diseases including fibrosis and cirrhosis; Raynaud's disease, Raynaud's phenomenon; bone related conditions including osteoporosis; metabolic disorders including food and water intake, diabetes, obesity; respiratory or a pulmonary disorder, including asthma, COPD, bronchial disease, lung diseases, cystic fibrosis, ARDS, SARS, the method comprising administering to the patient an effective amount of a peptide of the invention.

In a further aspect, the invention contemplates the use of the analogues and/or pharmaceutical compositions of the present invention in the manufacture of a medicament for the treatment of any disease or condition that involves relaxin-related family of GPCRs or LGR GPCRs family related disorder or condition in a patient, the disorder selected from the group consisting of but not limited to: hyperplastic disorders, neoplastic disorders, cancer; fibrotic conditions, disorders of collagen deposition, fibrotic breakdown, connective tissue remodeling, uncontrolled or abnormal collagen or fibronectin formation or breakdown; skin injuries including wound healing and scarring, scleroderma; urogenital disorders including female reproductive disorders, male and female infertility, cryptorchidism, disregulation of spermatogenesis and reproductive development including descent of the gonads; conditions associated with pregnancy such as preeclampsia or complication of labor; angiogenesis related disorders; cardiovascular disorders, vasodilatation, vasoconstriction or hypertension, endothelial disfunction and vascular disease, congestive heart failure, coronary artery disease, ischemia and ischemia-reperfusion, peripheral vascular disease; kidney disease, renal disease associated with arteriosclerosis or other narrowing of kidney capillaries; capillaries narrowing in the body, such as in the eyes or in the peripheral digits, the mesocaecum, lung and peripheral vasculature; CNS related disorders, neurological disorders, cognition and memory related indications, depression, neurological modification; inflammatory disorders, such as gastritis, gout, gouty arthritis, arthritis, rheumatoid arthritis, inflammatory bowel disease, Crohn's disease, ulcerative colitis, ulcers; autoimmune disorders; inflammatory conditions associated with viral infection and infection related diseases including fibrosis and cirrhosis; Raynaud's disease, Raynaud's phenomenon; bone related conditions including osteoporosis; metabolic disorders including food and water intake, diabetes, obesity; respiratory or a pulmonary disorder, including asthma, COPD, bronchial disease, lung diseases, cystic fibrosis, ARDS, SARS.

The term "relaxin-related family of GPCRs or LGR GPCRs family related disorder or condition" as used herein refers to conditions where relaxin-related family of GPCRs or LGR GPCRs family are involved or implicated in the development, maintenance or progression of the disease or condition.

The peptides of the invention falling within Formula I such as for example, peptides as depicted in SEQ ID NOs:1-15, 20-26 are also useful for the treatment of fibrotic conditions involving tissue remodeling following inflammation or ischemia-reperfusion injury, including but not limited to endomyocardial and cardiac fibrosis; mediastinal fibrosis; idiopathy pulmonary fibrosis; pulmonary fibrosis; retroperitoneal fibrosis; fibrosis of the spleen; fibrosis of the pancreas; hepatic fibrosis (cirrhosis) alcohol and non-alcohol related (including viral infection such as HAV, HBV and HCV); fibromatosis; granulomatous lung disease; glomerulonephritis, myocardial scarring following infarction; endometrial fibrosis and endometriosis; wound healing whether by injury or surgical procedures, diabetes related wound fibrosis.

The peptides of the invention falling within Formula I, such as for example, peptides as depicted in SEQ ID NOs: 1-15, 20-26 are also useful in treating cardiovascular diseases and their-complications, peripheral vascular diseases and coronary artery diseases, including but not limited to myocardial infarction; congestive heart failure (CHF); myocardial failure; myocardial hypertrophy; ischemic cardiomyopathy; systolic heart failure; diastolic heart failure; stroke; thrombotic stroke; concentric LV hypertrophy, myocarditis; cardiomyopathy; hypertrophic cardiomyopathy; myocarditis; decompensated heart failure; ischemic myocardial disease; congenital heart disease; angina pectoris; prevention of heart remodeling or ventricular remodeling after myocardial infarction; ischemia-reperfusion injury in ischemic and post-ischemic events (e.g. myocardial infarct); cerebrovascular accident; mitral valve regurgitation; hypertension; hypotension; restenosis; fibrosis; thrombosis; or platelet aggregation.

The peptides of the invention falling within Formulas I, such as for example, peptides as depicted in SEQ ID NOs: 1-15, 20-26 are useful in treating ischemia-reperfusion injury associated with ischemic and post-ischemic events in organs and tissues, including but not limited to thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure; restenosis; atherosclerosis; thrombosis; platelet aggregation.

The peptides of the invention falling within Formulas I, such as for example, peptides as depicted in SEQ ID NOs: 1-15, 20-26, are useful in treating ischemia-reperfusion injury following conditions including but not limited to procedures such as cardiac surgery; organ surgery; organ transplantation; angiography; cardiopulmonary and cerebral resuscitation.

In another aspect, the peptides of the invention falling within Formulas I, such as for example, peptides as depicted in SEQ ID NOs:1-15, 20-26, are used for prevention and treatment of hypertension and its complications including but not limited to hypertensive heart disease; antihypertension (blood pressure reduction); systemic and pulmonary high blood pressure; cerebrovascular disease and stroke; heart failure and stroke; left ventricular hypertrophy (LVH); congestive heart failure (CHF); hypertension, high blood pressure; vasodilation; renal hypertension; diuresis; nephritis; natriuresis; scleroderma renal crisis; angina pectoris (stable and unstable); myocardial infarction; heart attack; coronary artery disease; coronary heart disease; cardiac arrhythmias; atrial fibrillation; portal hypertension; raised intraocular pressure; vascular restenosis; chronic hypertension; valvular disease; myocardial ischemia; acute pulmonary edema; acute coronary syndrome; hypertensive retinopathy; hypertensive pregnancy sickness; preeclampsia; Raynaud's phenomenon; erectile dysfunction and glaucoma. These peptides are also used as a vasodilator and in antithrombotic therapy.

The peptides of the invention falling within Formulas I, such as for example, peptides as depicted in SEQ ID NOs: 1-15, 20-26, are also useful in treating inflammatory conditions associated with an infection, e.g., a bacterial infection or a viral infection, including but not limited to a viral infection caused by human immunodeficiency virus I (HIV-1) or HIV-2, acquired immune deficiency (AIDS), West Nile encephalitis virus, coronavirus, rhinovirus, influenza virus, dengue virus, HCV, HBV, HAV, hemorrhagic fever; an otological infection; severe acute respiratory syndrome (SARS), sepsis and sinusitis.

The peptides of the invention falling within Formulas I, such as for example, peptides as depicted in SEQ ID NOs: 1-15, 20-26, are also useful in the prevention or treatment of cancer, or inflammation associated with cancer such as solid cancer, including but not limited to colon cancer, lung cancer, breast cancer, prostate cancer, brain cancer, pancreatic cancer, ovarian cancer, kidney cancer, testicular cancer, bone cancer, osteosarcoma, or liver cancer (HBV/HCV related or non-related). The cancer can alternatively be a melanoma, glioma, a sarcoma, a leukemia, or lymphoma. These peptides are also useful in the prevention or treatment of invasive and metastatic cancer.

The peptides of the invention falling within Formulas I, such as for example, peptides as depicted in SEQ ID NOs: 1-15, 20-26, are used for the prevention and treatment in skin injuries, including but not limited to dermal repair, wound healing; burns, erythemas, lesions, wound healing following surgical procedures; skin or tissue lesions including lesions induced by conditions including, but not limited to Psoriasis, Lupus and Kaposhi Sarcoma; Scleroderma and collagenous diseases of the skin and skin tumors.

The peptides of the invention falling within Formulas I, such as for example, peptides as depicted in SEQ ID NOs: 1-15, 20-26, are used in the prevention or treatment of a urogenital disorder or a genitor-urological disorders including but not limited to renal disease; a bladder disorder; disorders of the reproductive system; gynecologic disorders; urinary tract disorder; incontinence; disorders of the male (spermatogenesis, spermatic motility), and female reproductive system; sexual dysfunction; erectile dysfunction; embryogenesis; and conditions associated with pregnancy. These are also used in pregnancy monitoring. As used herein, the term "conditions associated with pregnancy" includes, but is not limited to, conditions of fertilisation, pregnancy, parturition and lactation. The invention in another embodiment includes using the peptides of the invention falling within Formulas I, such as for example, peptides as depicted in SEQ ID NOs: 1-15, 20-26, wherein said pregnancy related disorders are selected from a group consisting of Abnormal endometrial angiogenesis; Placental development defects; Cervical ripening (softening); Abnormal implantation; Nipple development and disfunction; Pregnancy related remodeling of the Uterine tissue; Endometriosis; Preeclampsia; Lactation disorders; Estrogenic and non-estrogenic related hormonal disorders; Pre-term labor; post term labor; and Labor complications.

The invention also provides peptides falling within Formulas I, such as for example, peptides as depicted in SEQ ID NOs: 1-15, 20-26, that are used in the prevention or treatment of respiratory diseases, including but not limited to asthma, bronchial disease, lung diseases, chronic obstructive pulmonary disease (COPD), Acute Respiratory Distress Syndrome (ARDS), severe acute respiratory syndrome (SARS), Fibrosis related Asthma, cystic fibrosis.

The invention also provides peptides falling within Formulas I, such as for example, peptides as depicted in SEQ ID NOs: 1-15, 20-26, that are used in the prevention or treatment of metabolic disorders including but not limited to diabetes, diabetes mellitus, lipodystrophy, hyperthyroidism, glaucoma, hyperlipidaemia, non-insulin dependent diabetes, Food intake; Water intake; Feeding and drinking behaviors, Anorexia, Cachexia (cancer and non cancer related); Fat and lipid metabolism; and Energy control, appetite control and obesity.

The peptides of the invention falling within Formulas I, such as for example, peptides as depicted in SEQ ID NOs: 1-15, 20-26, are also used in the prevention and treatment of kidney diseases including but not limited to diabetic nephropathy; glomerulosclerosis; nephropathies; renal impairment; scleroderma renal crisis and chronic renal failure. These peptides can also be used as antidiuretics.

The peptides of the invention falling within Formulas I, such as for example, peptides as depicted in SEQ ID NOs: 1-15, 20-26, are also used in the prevention and treatment of angiogenesis related conditions including but not limited to retinal angiogenesis in a number of human ocular diseases such as diabetes mellitus, retinopathy of prematury, and age-related macular degeneration, or cancer associated angiogenesis in primary or metastatic cancer, including but not limited to cancer of the prostate, brain, breast, colorectal, lung, ovarian, pancreatic, renal, cervical, melanoma, soft tissue sarcomas, lymphomas, head-and-neck, and glioblastomas.

The peptides of the invention falling within Formulas I, such as for example, peptides as depicted in SEQ ID NOs: 1-15, 20-26, are also used to treat a central nervous system (CNS) disorder, including but not limited to central and peripheral degenerative neuropathies; neuroprotection; impaired cognition; anxiety disorders, pain control, food intake, a behavioral disorder, a learning disorder, a sleep disorder, a memory disorder, a pathologic response to anesthesia, addiction, depression, migraine, a menstruation disorder, muscle spasm, opiate dependence, dementia, Alzheimer's disease, Parkinson's disease, cortical function, locomotor activity, Alcohol and Drug addiction and abuse; Impaired memory; Feeding and drinking related behaviours; Stress control, Bipolar disorder; Schizophrenia; Schizoaffective; Multiple Sclerosis (MS); Stroke and stroke damage repair (Ischemia protection); Vasculature and re-vasculature in the brain; and Brain tissue regeneration and a peripheral nervous system disorder.

The peptides of the invention falling within Formulas I, such as for example, peptides as depicted in SEQ ID NOs: 1-15, 20-26, are also used to treat a bone and bone related disorders in a patient, including but not limited to Osteoporosis; Osteoarthritis; Osteopetrosis; Bone inconsistency; Osteosarcoma; and Cancer matastesis to the bone.

The peptides of the invention falling within Formulas I, such as for example, peptides as depicted in SEQ ID NOs: 1-15, 20-26, are also used to treat endothelial dysfunction disease, selected from a group consisting of cardiovascular diseases, high blood pressure, atherosclerosis, thrombosis, myocardial infarct, heart failure, renal diseases, plurimetabolic syndrome, erectile dysfunction; vasculitis; and diseases of the central nervous system (CNS).

The peptides of the invention falling within Formulas I, such as for example, peptides as depicted in SEQ ID NOs: 1-15, 20-26, are also used to treat inflammatory disorder in a subject. The inflammatory disorder can be gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyper-responsiveness, vasculitis, septic shock and inflammatory skin disorders, including but not limited to psoriasis, atopic dermatitis, eczema.

The peptides of the invention falling within Formulas I, such as for example, peptides as depicted in SEQ ID NOs: 1-15, 20-26, are also used to treat autoimmune disease or disorder in a subject. The autoimmune disease can be multiple sclerosis, psoriasis, rheumatoid arthritis, systemic lupus erythematosus, ulcerative colitis, Crohn's disease, transplant rejection, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitis, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

Compounds of Formula I can be used to treat disorders, diseases and/or conditions as described herein, by administering to a subject in need thereof a therapeutically effective amount of a peptide falling within Formula I.

Also provided by the invention is a method of treating disorders for which modulation of GPCR-related signal transduction pathways is efficacious. For example, provided by the invention is a method of treating disorders for which modulation of relaxin-related family of GPCR and/or LGR family of GPCRs is efficacious in a subject by administering to a subject in need thereof a therapeutically effective amount of a compound falling within Formula I, such as for example, peptides as depicted in SEQ ID NOs: 1-15, 20-26. Such diseases disorders and/or condition are selected from but not limited to hyperplastic disorders, neoplastic disorders, cancer; fibrotic conditions, disorders of collagen deposition, fibrotic breakdown, connective tissue remodeling, uncontrolled or abnormal collagen or fibronectin formation or breakdown; skin injuries including wound healing and scarring, scleroderma; urogenital disorders including female reproductive disorders, male and female infertility, cryptorchidism, disregulation of spermatogenesis and reproductive development including descent of the gonads; conditions associated with pregnancy such as preeclampsia or complication of labor; angiogenesis related disorders; cardiovascular disorders, vasodilatation, vasoconstriction or hypertension, endothelial disfunction and vascular disease, congestive heart failure, coronary artery disease, ischemia and ischemia-reperfusion, peripheral vascular disease; kidney disease, renal disease associated with arteriosclerosis or other narrowing of kidney capillaries; capillaries narrowing in the body, such as in the eyes or in the peripheral digits, the mesocaecum, lung and peripheral vasculature; CNS related disorders, neurological disorders, cognition and memory related indications, depression, neurological modification; inflammatory disorders, such as gastritis, gout, gouty arthritis, arthritis, rheumatoid arthritis, inflammatory bowel disease, Crohn's disease, ulcerative colitis, ulcers; autoimmune disorders; inflammatory conditions associated with viral infection and infection related diseases including fibrosis and cirrhosis; Raynaud's disease, Raynaud's phenomenon; bone related conditions including osteoporosis; metabolic disorders including food and water intake, diabetes, obesity; respiratory or a pulmonary disorder, including asthma, COPD, bronchial disease, lung diseases, cystic fibrosis, ARDS, SARS.

Also provided by the invention is a method of treating an inflammatory disorder in a subject by administering to a subject in need thereof a therapeutically effective amount of a compound falling within Formula I, such as for example, peptides as depicted in SEQ ID NOs: 1-15, 20-26. The inflammatory disorder can be gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyper-responsiveness, vasculitis, septic shock and inflammatory skin disorders, including but not limited to psoriasis, atopic dermatitis, eczema.

Also provided by the invention is a method of treating fibrotic conditions involving tissue remodeling in a subject by administering to a subject in need thereof a therapeutically effective amount of a compound falling within Formula I such as for example, peptides as depicted in SEQ ID NOs: 1-15, 20-26. These fibrotic conditions can be endomyocardial and cardiac fibrosis fibrosis; mediastinal fibrosis; idiopathy pulmonary fibrosis; pulmonary fibrosis; retroperitoneal fibrosis; fibrosis of the spleen; fibrosis of the pancreas; hepatic fibrosis (cirrhosis) alcohol and non-alcohol related (including viral infection such as HAV, HBV and HCV); fibromatosis; granulomatous lung disease; glomerulonephritis, myocardial scarring following infarction; endometrial fibrosis and endometriosis; wound healing whether by injury or surgical procedures, diabetes related wound fibrosis.

Also provided by the invention is a method of treating an autoimmune disease or disorder in a subject by administering to a subject in need thereof a therapeutically effective amount of a compound falling within Formula I, such as for example, peptides as depicted in SEQ ID NOs: 1-15, 20-26. The autoimmune disease can be multiple sclerosis, psoriasis, rheumatoid arthritis, systemic lupus erythematosus, ulcerative colitis, Crohn's disease, transplant rejection, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitus, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis and chondrocalcinosis.

Also provided by the invention is a method of treating cardiovascular diseases and their complications in a subject by administering to a subject in need thereof a therapeutically effective amount of a compound falling within Formula I, such as for example, peptides as depicted in SEQ ID NOs: 1-15, 20-26. The cardiovascular diseases can be peripheral vascular diseases and coronary artery diseases, including but not limited to myocardial infarction; coronary heart disease; congestive heart failure (CHF); myocardial failure; myocardial hypertrophy; ischemic cardiomyopathy; systolic heart failure; diastolic heart failure; stroke; thrombotic stroke; concentric LV hypertrophy, myocarditis; cardiomyopathy; hypertrophic cardiomyopathy; myocarditis; decompensated heart failure; ischemic myocardial disease; congenital heart disease; angina pectoris; prevention of heart remodeling or ventricular remodeling after myocardial infarction; ischemia-reperfusion injury in ischemic and post-ischemic events (e.g. myocardial infarct); cerebrovascular accident; mitral valve regurgitation; hypertension; hypotension; restenosis; fibrosis; thrombosis; or platelet aggregation.

Also provided by the invention is a method of treating an ischemia-reperfusion injury in a subject by administering to a subject in need thereof a therapeutically effective amount of a compound falling within Formula I, such as for example, peptides as depicted in SEQ ID NOs: 1-15, 20-26. The ischemia-reperfusion injury can be associated with ischemic and post-ischemic events in organs and tissues, including but not limited to thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure; restenosis; atherosclerosis; thrombosis; platelet aggregation. The ischemia-reperfusion injury can be alternatively following conditions including but not limited to procedures such as cardiac surgery; organ surgery; organ transplantation; angiography; cardiopulmonary and cerebral resuscitation.

Also provided by the invention is a method of preventing and treating an hypertension and its complications in a subject by administering to a subject in need thereof a therapeutically effective amount of a compound falling within Formula I, such as for example, peptides as depicted in SEQ ID NOs: 1-15, 20-26. The hypertension and its complications can be hypertensive heart disease; antihypertension (blood pressure reduction); systemic and pulmonary high blood pressure; cerebrovascular disease and stroke; heart failure and stroke; left ventricular hypertrophy (LVH); congestive heart failure (CHF); hypertension, high blood pressure; vasodilation; renal hypertension; diuresis; nephritis; natriuresis; scleroderma renal crisis; angina pectoris (stable and unstable); myocardial infarction; heart attack; coronary artery disease; coronary heart disease; cardiac arrhythmias; atrial fibrillation; portal hypertension; raised intraocular pressure; vascular restenosis; chronic hypertension; valvular disease; myocardial ischemia; acute pulmonary edema; acute coronary syndrome; hypertensive retinopathy; hypertensive pregnancy sickness; preeclampsia; Raynaud's phenomenon; erectile dysfunction and glaucoma. These peptides are also used as a vasodilator and in antithrombotic therapy.

Also provided by the invention is a method of treating an inflammatory disorder and/or conditions associated with an infection in a subject by administering to a subject in need thereof a therapeutically effective amount of a compound falling within Formulas I, such as for example, peptides as depicted in SEQ ID NOs: 1-15, 20-26. The inflammatory conditions associated with an infection, can be a bacterial infection or a viral infection, including but not limited to a viral infection caused by human immunodeficiency virus I (HIV-1) or HIV-2, acquired immune deficiency (AIDS), HAV, HCV, HBV, West Nile encephalitis virus, coronavirus, rhinovirus, influenza virus, dengue virus, hemorrhagic fever; an otological infection; severe acute respiratory syndrome (SARS), sepsis and sinusitis.

Also provided by the invention is a method of treating cancer, or inflammation associated with cancer in a subject by administering to a subject in need thereof a therapeutically effective amount of a compound falling within Formulas I, such as for example, peptides as depicted in SEQ ID NOs: 1-15, 20-26. The cancer, or inflammation associated with cancer can be solid cancer, including but not limited to colon cancer, lung cancer, breast cancer, prostate cancer, brain cancer, pancreatic cancer, ovarian cancer, testicular cancer, bone cancer, osteosarcoma, liver cancer (HBV/HCV related or non-related), or kidney cancer. The cancer can alternatively be a melanoma, glioma, a sarcoma, a leukemia, or lymphoma. These peptides are also useful in the prevention or treatment of invasive and metastatic cancer.

Also provided by the invention is a method of treating skin injury diseases, disorders and/or conditions in a subject by administering to a subject in need thereof a therapeutically effective amount of a compound falling within Formulas I, such as for example, peptides as depicted in SEQ ID NOs: 1-15, 20-26. The skin injury diseases, disorders and/or conditions can be dermal repair, wound healing; burns, erythemas, lesions, wound healing following surgical procedures; skin or tissue lesions including lesions induced by conditions including, but not limited to Psoriasis, Lupus and Kaposhi Sarcoma; Scleroderma and collagenous diseases of the skin and skin tumors.

Also provided by the invention is a method of prevention or treatment of a urogenital disorder or a genitor-urological disorders in a subject by administering to a subject in need thereof a therapeutically effective amount of a compound falling within Formulas I such as for example, peptides as depicted in SEQ ID NOs: 1-15, 20-26. The a urogenital disorder or a genitor-urological disorders can be renal disease; a bladder disorder; disorders of the reproductive system; gynecologic disorders; urinary tract disorder; incontinence; disorders of the male (spermatogenesis, spermatic motility), and female reproductive system; sexual dysfunction; erectile dysfunction; embryogenesis; and conditions associated with pregnancy. These are also used in pregnancy monitoring. As used herein, the term "conditions associated with pregnancy" includes, but is not limited to, conditions of fertilisation, pregnancy, parturition and lactation. The invention in another embodiment includes the foregoing method, wherein said pregnancy related disorders are selected from a group consisting of Abnormal endometrial angiogenesis; Placental development defects; Cervical ripening (softening); Abnormal implantation; Nipple development and disfunction; Pregnancy related remodeling of the Uterine tissue; Endometriosis; Preeclampsia; Lactation disorders; Estrogenic and non-estrogenic related hormonal disorders; Pre-term labor; post term labor; and Labor complications.

Also provided by the invention is a method of prevention or treatment of respiratory diseases in a subject by administering to a subject in need thereof a therapeutically effective amount of a compound falling within Formulas I, II, IV and VI, such as for example, peptides as depicted in SEQ ID NOs: 1-15, 20-26. The respiratory diseases can be asthma, bronchial disease, lung diseases, chronic obstructive pulmonary disease (COPD), Acute Respiratory Distress Syndrome (ARDS), severe acute respiratory syndrome (SARS), Fibrosis related Asthma, cystic fibrosis.

Also provided by the invention is a method of prevention or treatment of metabolic disorders in a subject by administering to a subject in need thereof a therapeutically effective amount of a compound falling within Formulas I, such as for example, peptides as depicted in SEQ ID NOs: 1-15, 20-26. The metabolic disorders can be diabetes, diabetes mellitus, lipodystrophy, hyperthyroidism, glaucoma, hyperlipidaemia, non-insulin dependent diabetes, Food intake; Water intake; Feeding and drinking behaviors, Anorexia, Cachexia (cancer and non cancer related); Fat and lipid metabolism; and Energy control, appetite control and obesity.

Also provided by the invention is a method of prevention and treatment of kidney diseases in a subject by administering to a subject in need thereof a therapeutically effective amount of a compound falling within I, such as for example, peptides as depicted in SEQ ID NOs: 1-15, 20-26. The kidney diseases can be diabetic nephropathy; glomerulosclerosis; nephropathies; renal impairment; scleroderma renal crisis and chronic renal failure.

Also provided by the invention is a method of prevention and treatment of angiogenesis related conditions in a subject by administering to a subject in need thereof a therapeutically effective amount of a compound falling within Formulas I such as for example, peptides as depicted in SEQ ID NOs: 1-15, 20-26. The angiogenesis related conditions including but not limited to retinal angiogenesis in a number of human ocular diseases such as diabetes mellitus, retinopathy of prematury, and age-related macular degeneration, or cancer associated angiogenesis in primary or metastatic cancer, including but not limited to cancer of the prostate, brain, breast, colorectal, lung, ovarian, pancreatic, renal, cervical, melanoma, soft tissue sarcomas, lymphomas, head-and-neck, and glioblastomas.

Also provided by the invention is a method of treating central nervous system (CNS) disorder, in a subject by administering to a subject in need thereof a therapeutically effective amount of a compound falling within Formulas I, such as for example, peptides as depicted in SEQ ID NOs: 1-15, 20-26. The central nervous system (CNS) disorder, including but not limited to central and peripheral degenerative neuropathies; neuroprotection; impaired cognition; anxiety disorders, pain control, food intake, a behavioral disorder, a learning disorder, a sleep disorder, a memory disorder, a pathologic response to anesthesia, addiction, depression, migraine, a menstruation disorder, muscle spasm, opiate dependence, dementia, Alzheimer's disease, Parkinson's disease, cortical function, locomotor activity, Alcohol and Drug addiction and abuse; Impaired memory; Feeding and drinking related behaviours; Stress control, Bipolar disorder; Schizophrenia; Schizoaffective; Multiple Sclerosis (MS); Stroke and stroke damage repair (Ischemia protection); Vasculature and re-vasculature in the brain; and Brain tissue regeneration and a peripheral nervous system disorder.

Also provided by the invention is a method of treating bone and bone related disorders in a subject by administering to a subject in need thereof a therapeutically effective amount of a compound falling within Formulas I, such as for example, peptides as depicted in SEQ ID NOs: 1-15, 20-26. The bone and bone related disorders including but not limited to Osteoporosis; Osteoarthritis; Osteopetrosis; Bone inconsistency; Osteosarcoma; and Cancer matastesis to the bone.

Also provided by the invention is a method of treating endothelial dysfunction disease, in a subject by administering to a subject in need thereof a therapeutically effective amount of a compound falling within Formulas I, such as for example, peptides as depicted in SEQ ID NOs: 1-15, 20-26. The endothelial dysfunction disease is selected from a group consisting of cardiovascular diseases, high blood pressure, atherosclerosis, thrombosis, myocardial infarct, heart failure, renal diseases, plurimetabolic syndrome, erectile dysfunction; vasculitis; and diseases of the central nervous system (CNS).

Optionally, the cDNA that encodes the peptide sequences of the invention are used in gene therapy to treat the respective diseases, disorders and/or conditions, as detailed hereinabove.

The invention will be further illustrated in the following examples.

EXAMPLE 1

Peptides Synthesis

All P74, P59-S and P59 related peptides derive from C1QT8, a Collagen repeat containing Hypothetical protein (SEQ ID NO:19) or its orthologous or homologous sequences:

```
>P60827 C1QT8_HUMAN Complement C1q tumor necrosis
factor-related protein 8-Homo sapiens (Human).
MAAPALLLLALLLPVGAWPGLPRRPCVHCCRPAWPPGPYARVSDRDLWR

GDLWRGLPRVRPTIDIEILKGEKGEAGVRGRAGRSGKEGPPGARGLQGR

RGQKGQVGPPGAACRRAYAAFSVGRRAYAAFSVGRREGLHSSDHFQAVP

FDTELVNLDGAFDLAAGRFLCTVPGVYFLSLNVHTWNYKETYLHIMLNR

RPAAVLYAQPSERSVMQAQSLMLLLAAGDAVWVRMFQRDRDNAIYGEHG

DLYITFSGHLVKPAAEL

Peptide P59-S-Amide (Amide):
                                            (SEQ ID NO: 1)
AYAAFSV-Amide;

Peptide P59-SG (free acid Gly)
                                            (SEQ ID NO: 2)
AYAAFSV;

Peptide P59-Amide (amide)
                                            (SEQ ID NO: 3)
GQKGQVGPPGAACRRAYAAFSV-Amide;

Peptide P59 (free acid)
                                            (SEQ ID NO: 4)
GQKGQVGPPGAACRRAYAAFSV;

Peptide P59C13V-Amide (amide)
                                            (SEQ ID NO: 5)
GQKGQVGPPGAAV*RRAYAAFSV-Amide Peptide P59C13V (free acid)
                                            (SEQ ID NO: 6)
GQKGQVGPPGAAV*RRAYAAFSV;

Peptide P74-Amide (Amide):
                                            (SEQ ID NO: 7)
GQKGQVGPPGAACRRAYAAFSVGRRAYAAFSV-Amide Peptide P74 (free acid)
                                            (SEQ ID NO: 8)
GQKGQVGPPGAACRRAYAAFSVGRRAYAAFSV Peptide P74C13V (amide)
                                            (SEQ ID NO: 9)
GQKGQVGPPGAAV*RRAYAAFSVGRRAYAAFSV-Amide Peptide P74C13V (free acid)
                                            (SEQ ID NO: 10)
GQKGQVGPPGAAV*RRAYAAFSVGRRAYAAFSV Peptide P59SG (free acid Gly)
                                            (SEQ ID NO: 11)
AYAAFSVG;

Peptide P59-G (free acid Gly)
                                            (SEQ ID NO: 12)
GQKGQVGPPGAACRRAYAAFSVG;

Peptide P59C13V-G (free acid Gly)
                                            (SEQ ID NO: 13)
GQKGQVGPPGAAV*RRAYAAFSVG;

Peptide P74-G (free acid Gly)
                                            (SEQ ID NO: 14)
GQKGQVGPPGAACRRAYAAFSVGRRAYAAFSVG Peptide P74C13V-G (free acid Gly)
                                            (SEQ ID NO: 15)
GQKGQVGPPGAAV*RRAYAAFSVGRRAYAAFSVG Peptide P59-Chimpanzee
                                            (SEQ ID NO: 20)
GQKGQVGPPGAACQRAYAAFSVG;

Peptide P59-Orangutan
                                            (SEQ ID NO: 21)
GQKGQVGPPGAPCQRAYAAFSVG;

Peptide P59-Rhesus
                                            (SEQ ID NO: 22)
GQKGQVGPPGAPCQRAYAAFSVG;

Peptide P59-Cow
                                            (SEQ ID NO: 23)
GQKGQAGLPGAQCPRAYAAFSVG;

Peptide P59-Chicken
                                            (SEQ ID NO: 24)
GQKGQPGPQGHSCKQLYAAFSVG;

Peptide P59-C1QTNF1 (Human)
                                            (SEQ ID NO: 25)
GQKGSMGAPGERCKSHYAAFSVG;

Peptide P59-Rat
                                            (SEQ ID NO: 26)
GQKGSMGAPGDHCKSQYAAFSVG.
```

Peptides were synthesized by the solid phase peptide synthesis (SPPS) method, cleaved from the resin, and purified by RP-HPLC unless stated otherwise. The peptide's identity was verified by mass spectrometry. Final purity of peptide was >90% as measured by RP-HPLC. Peptides were diluted in PBS containing 0.1% BSA. All plates were stored at −80C until use.

EXAMPLE 2

Effect of Peptides P59C13V (P59) (SEQ ID NO:6) and P74C13V (P74) (SEQ ID NO:10) on Cyclic AMP Accumulation in Cho-K1 Cells Expressing LGR7 and LGR8

The ability of Peptides to affect cAMP concentration was examined in CHO-K1 cells transiently transfected with LGR7 (RXFP1) or LGR8 (RXFP2). The experiment measured cAMP concentration in response to the addition of the peptides. LGR7 (RXFP1) or LGR8 (RXFP2) were transiently transfected into CHO-K1 cells as follows: Cells (12 million) were plated into T75 flasks on the day preceding transfection. Cells were transfected with a GPCR DNA and $G_{\alpha 16}$ using a lipid technique according to the manufacturer's recommendation. Cells were transfected for 5 hours, then re-plated into 96-well dishes (60,000 cells per well) and grown overnight. Transfected cells were plated into 24 wells of a 96-well plate. Cells were pre-treated with 0.5 mM IBMX (stimulation buffer) for 10 min at 37° C., then stimulated with either a positive control (Relaxin 2) or a candidate peptide (for Gs functional examination), followed by stimulation or a preincubation with 10 µM forskolin (for Gi functional examination). Following a 20 minutes stimulation by incubation with 1 µM of either positive control or the tested peptides, either with or without forskolin, intracellular cAMP was assayed using the Hit Hunter cAMP kit (DiscoveRx Corporation)

according to the manufacturer's recommended protocol. Data was converted to nmol of cAMP by running a standard cAMP curve.

Relaxin was used as a positive control. cAMP level was elevated by pre-treatment with forskolin.

The transfected CHO-K1 cells were treated with 10 uM of Forskolin (Applied cell sciences (ACS)) for 10 minutes and then challenged with 1 uM of H2 Relaxin (ACS) (as a positive control), 1 uM of Peptide P59C13V (P59) (SEQ ID NO: 6), and Peptide P74C13V (P74) (SEQ ID NO: 10).

The results are shown in FIG. 1. As can be seen from FIG. 1, both peptides P59C13V (P59) (SEQ ID NO: 6) and P74C13V (SEQ ID NO: 10) showed a cAMP inhibitory effect with respect to stimulation by Forskolin, and in relation to the effect H2 Relaxin positive control had on the cells. A clear cAMP inhibition (Gi) effect was demonstrated by P59C13V (P59) (SEQ ID NO: 6) and P74C13V (P74) (SEQ ID NO: 10) on both receptors at 1 uM. Relaxin affected only the LGR7 (RXFP1) receptor. P59C13V (P59) (SEQ ID NO: 6) showed a stronger effect, than P74C13V (P74) (SEQ ID NO: 10), however, both peptides showed stronger effect when compared to the reduction in cAMP with the positive control (Relaxin 2).

Figure 2:
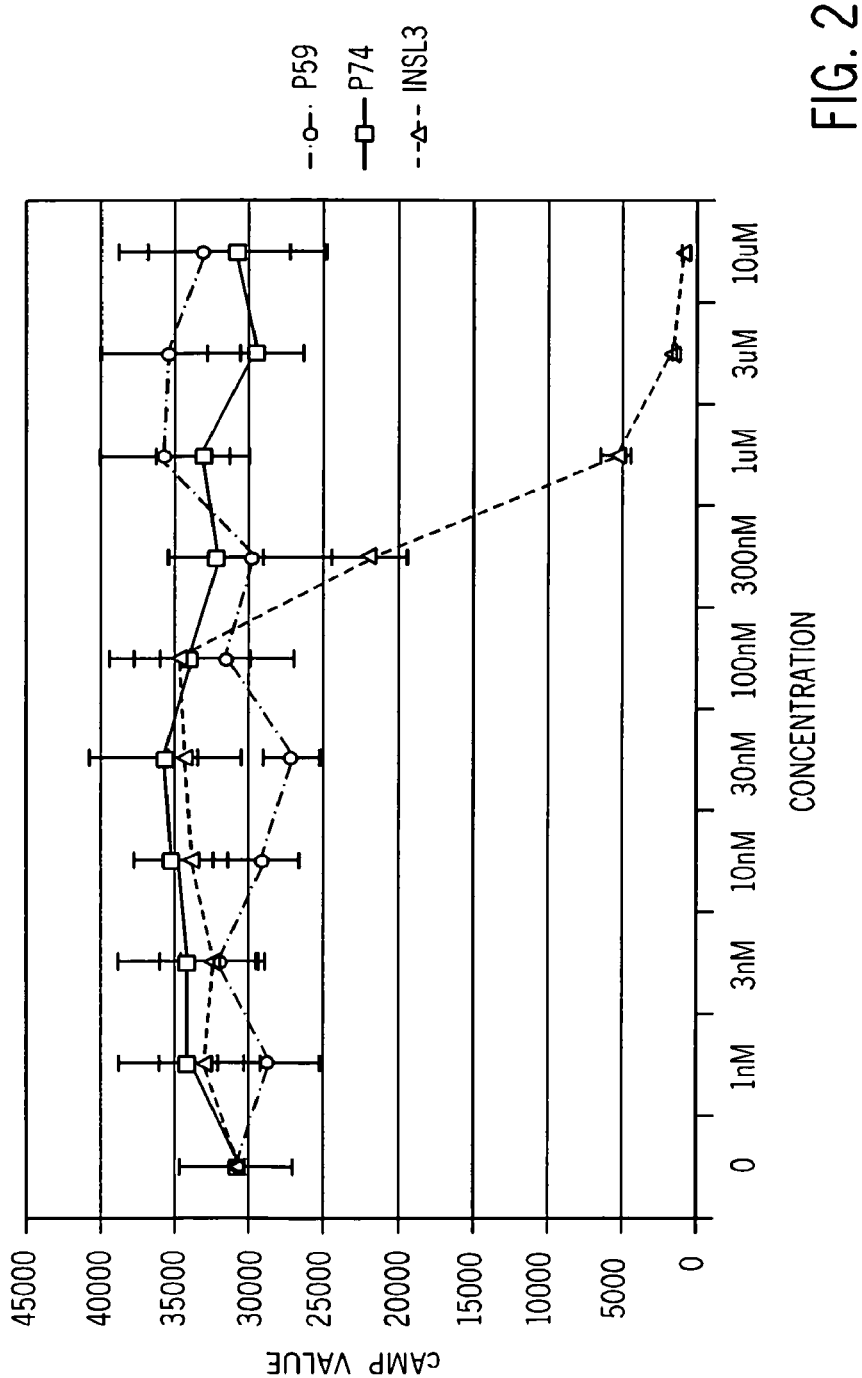
FIG. 2 presents a Gi (cAMP inhibition) dose response curve at concentrations between 1 nM to 10 uM of P59C13V (P59), P74C13V (P74) and INSL3 on CHO-K1 cells transiently transfected with LGR8 (RXFP2) and pre-treated with 20 uM of Forskolin.

A dose response effect of P59C13V (P59) and P74C13V (P74) on CHO-K1 cells transiently transfected with LGR8 (RXFP2) was further examined (Method as above). CHO-K1 cells transiently transfected with LGR8 (RXFP2) were treated with 20 uM of Forskolin for 10 minutes and then challenged with either INSL3 (as a positive control), P59C13V (SEQ ID NO: 6) or P74C13V (P74) (SEQ ID NO: 10) at increasing concentrations from 1 nM to 10 uM. The results are shown in FIG. 2. As can be seen from FIG. 2, P59C13V (P59) (SEQ ID NO: 10) showed a slight decrease in cAMP at concentrations lower than 100 nM; (Gi effect) and a slight increase (Gs effect) at concentrations higher than100 nM, as compared to INSL3. INSL3 showed a slight dose dependent increase in lower concentrations (<100 nM; Gs effect), and a sharp decrease (Gi effect) in higher concentrations (>100 nM). P74C13V (P74) (SEQ ID NO: 10) showed a pattern similar to INSL3 at lower concentrations (slight increase in cAMP) but no effect at higher concentrations.

EXAMPLE 3

Effect of Peptides P59C13V (P59) (SEQ ID NO: 6) and P74C13V (P74) (SEQ ID NO: 10) on cAMP Accumulation in CHO-K1 Cells Expressing LGR4, LGR5 or LGR6

The ability of Peptides to affect cAMP concentration was examined in CHO-K1 cells transiently transfected the GPCR's LGR4, LGR5, or LGR6 and treated with 1 uM of P59C13V (P59) (SEQ ID NO: 6), P74C13V (P74) ((SEQ ID NO: 10), or HCG (ACS) which was used as a positive control. cAMP accumulation in the cells was then measured as described above with (Gi) or without (Gs) pre-treatment with Forskolin.

Figure 3A:
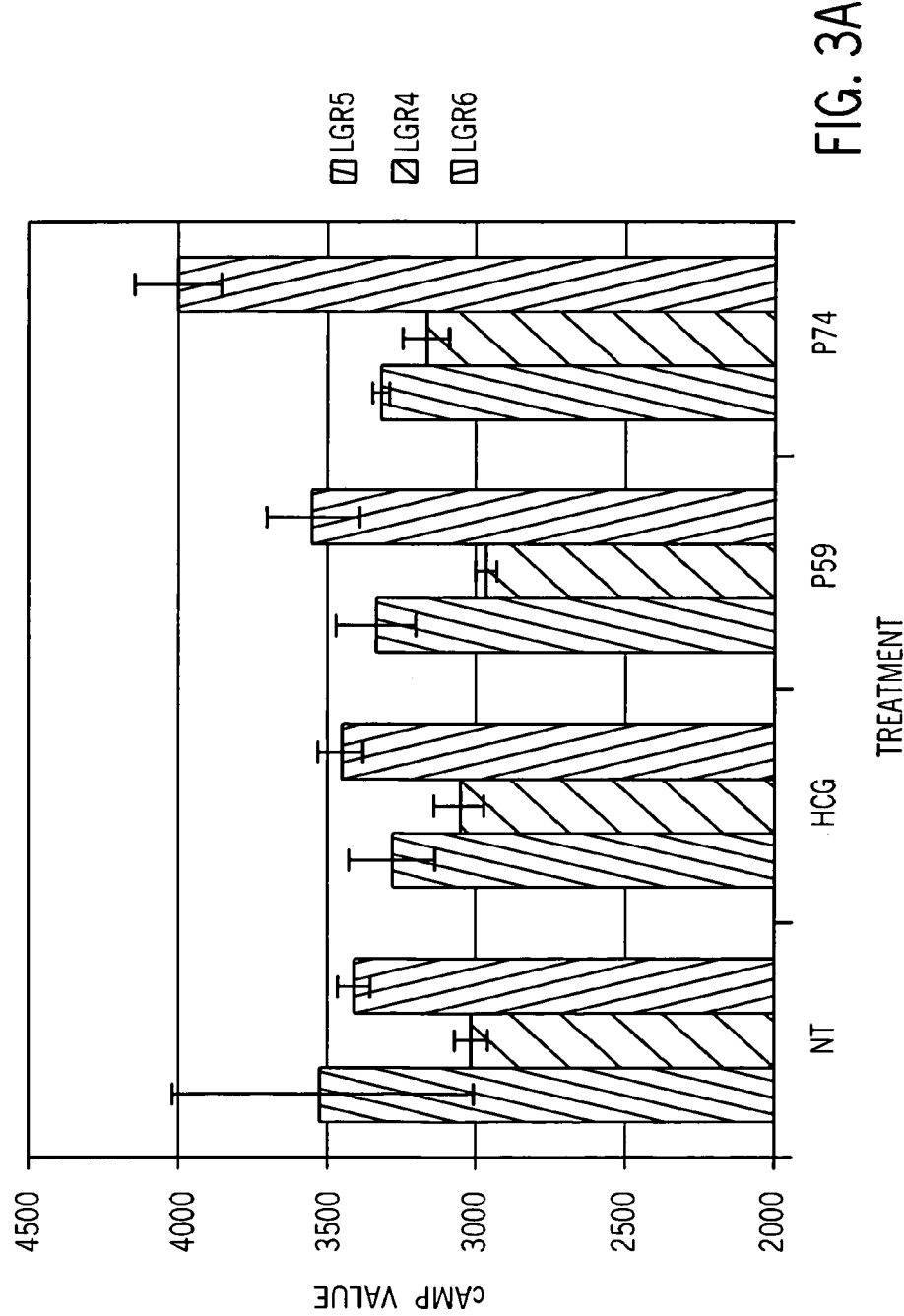
FIG. 3A is a graph showing a Gs (cAMP increase) assay following no treatment or treatment with HCG (control), P59C13V (P59) and P74C13V (P74), respectively on LGR4, LGR5, and LGR6 transfected CHO-K1 cells.

The results are shown in FIG. 3. According to FIG. 3A, a significant increase in cAMP accumulation was demonstrated for LGR6 transfected cells when challenged with P74C13V (P74) (SEQ ID NO: 10). No significant Gs activation was found for any of the peptides on any of the other LGR transfected cells.

Figure 3B:
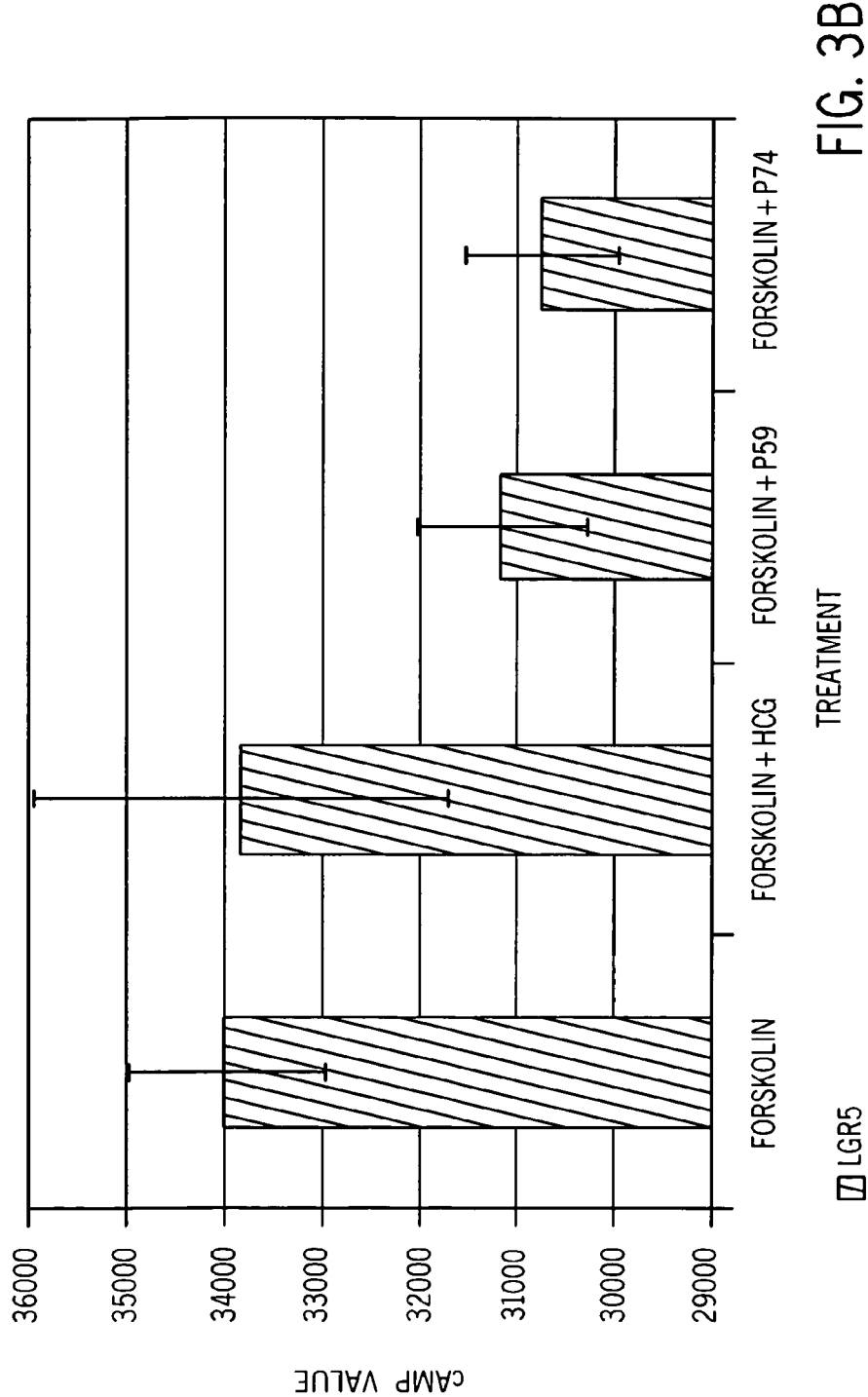
FIG. 3B is a graph showing a Gi (cAMP inhibition) assay following pre treatment by 20 uM of Forskolin followed by no treatment or treatment with HCG (control), P59C13V (P59), and P74C13V (P74), respectively on LGR5, transfected CHO-K1 cells.

According to FIG. 3B, a significant Gi effect (decrease in cAMP accumulation) was demonstrated for LGR5 transfected cells when challenged with P59C13V (P59) (SEQ ID NO: 6) or P74C13V (P74) (SEQ ID NO: 10). No significant Gi activation was found for the positive control (HCG).

Figure 3C:
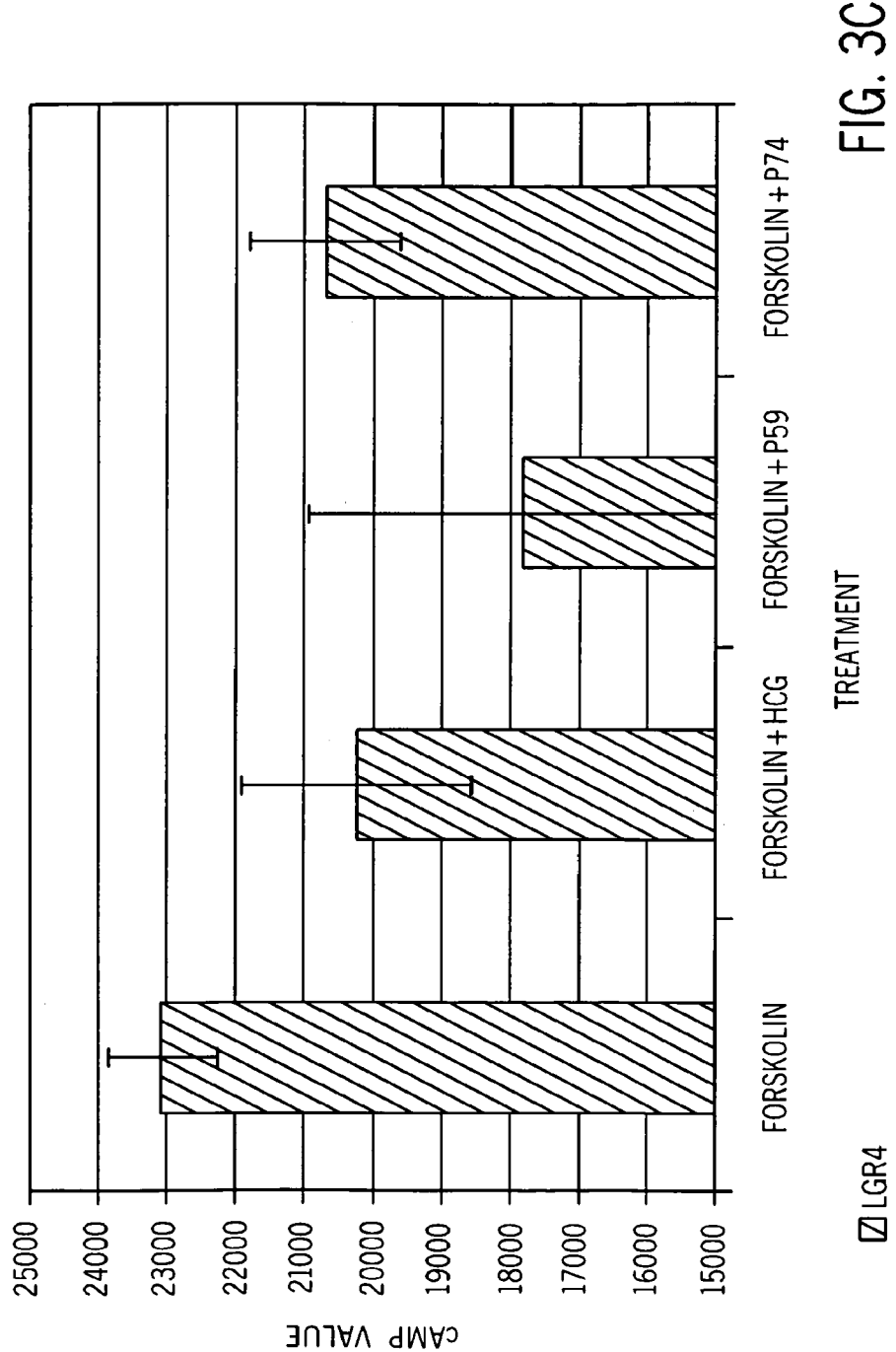
FIG. 3C is a graph showing a Gi (cAMP inhibition) assay following pre treatment by 20 uM of Forskolin followed by no treatment or treatment with HCG (control), P59C13V (P59), and P74C13V (P74), respectively on LGR4, transfected CHO-K1 cells.

According to FIG. 3C, a slight yet statistically significant Gi effect (decrease in cAMP accumulation) was demonstrated for LGR4 transfected cells when challenged with P59C13V (P59) (SEQ ID NO: 6) or P74C13V (P74) (SEQ ID NO: 10). A slight but significant Gi activation was found for the positive control (HCG).

FIG. 3 (A-C) indicate a slight Gs activation of LGR6 by P74C13V (P74), a slight Gi activation of LGR5 by both P59C13V (P59) (SEQ ID NO: 6) and P74C13V (P74) (SEQ ID NO: 10) and a slight Gi activation of LGR4 by both P59C13V (P59) (SEQ ID NO: 6) and P74C13V (P74) (SEQ ID NO: 10) as well as HCG.

EXAMPLE 4

Dose Response Stimulation of Camp Mediated by Peptides P59 (SEQ ID NO: 6) and P74 (SEQ ID NO: 10) in CHO-K1 Cells Expressing LGR7

CHO-K1 cells transiently transfected with LGR7 (RXFP1) were treated with 10 uM of Forskolin for 10 minutes and then challenged with either H2 Relaxin (as a positive control), P59C13V (P59) (SEQ ID NO: 6) or P74C13V (P74) (SEQ ID NO: 10) at increasing concentrations, from 1 nm to 10 uM (FIG. 4A) and from 3 nM to 100 nM (FIG. 4B). cAMP concentrations were determined at each point, as described above with (FIG. 4A) or without (FIG. 4B) the presence of Forskolin.

The results are presented in FIG. 4. As can be seen from FIG. 4A, P59C13V (SEQ ID NO: 6) showed a bell-shaped curve as in lower concentrations there was an increase in cAMP (Gs effect), in the 30 and 100 nM doses, as compared to H2 Relaxin, whereas Relaxin showed a dose dependent decrease (Gi) effect in higher concentrations (>100 nM). P74C13V (SEQ ID NO: 10) showed no significant effect in this assay.

FIG. 4B describes a Gs (cAMP stimulation and increase in cAMP accumulation) dose response was measured for LGR7 (RXFP1)-transfected CHO-K1 cells using low concentrations (3-100 nM) of P59C13V (P59) (SEQ ID NO: 6) or H2 Relaxin. Both P59C13V (P59) and H2 Relaxin showed a dose dependent increase in cAMP. As shown in FIG. 4B, P59C13V (P59) (SEQ ID NO: 6) was more effective than Relaxin in increasing cAMP levels in these studies.

The ability of P59C13V (SEQ ID NO: 6) and H3 Relaxin to activate CHO-K1 cells transfected by GPR135 (RXFP3), which is a non-LGR, Relaxin related receptor, was tested. The assay was performed by Euroscreen. For cAMP concentration analysis, Euroscreen cat. ES-656-A-cells (RXFP3, Euroscreen cat. ES-656-A) grown to mid-log phase in culture media without antibiotics were detached with PBS-EDTA, centrifuged and resuspended in assay buffer at a concentration of $7.5 \times 10^5$ cells/ml. The test was performed in 96 well plates. For agonist testing, 12 μl of cells ($5 \times 10^3$ cells/well) were mixed with 12 μl of agonist Either H3-Relaxin or P59C13V (P59) (SEQ ID NO: 6) at increasing concentrations. The plates were then incubated for 30 min at room temperature. After addition of the lysis buffer, cAMP concentrations were estimated, according to the manufacturer specification, with the HTRF kit from Cis-Bio International (cat no 62AM2PEB).

Figure 5:
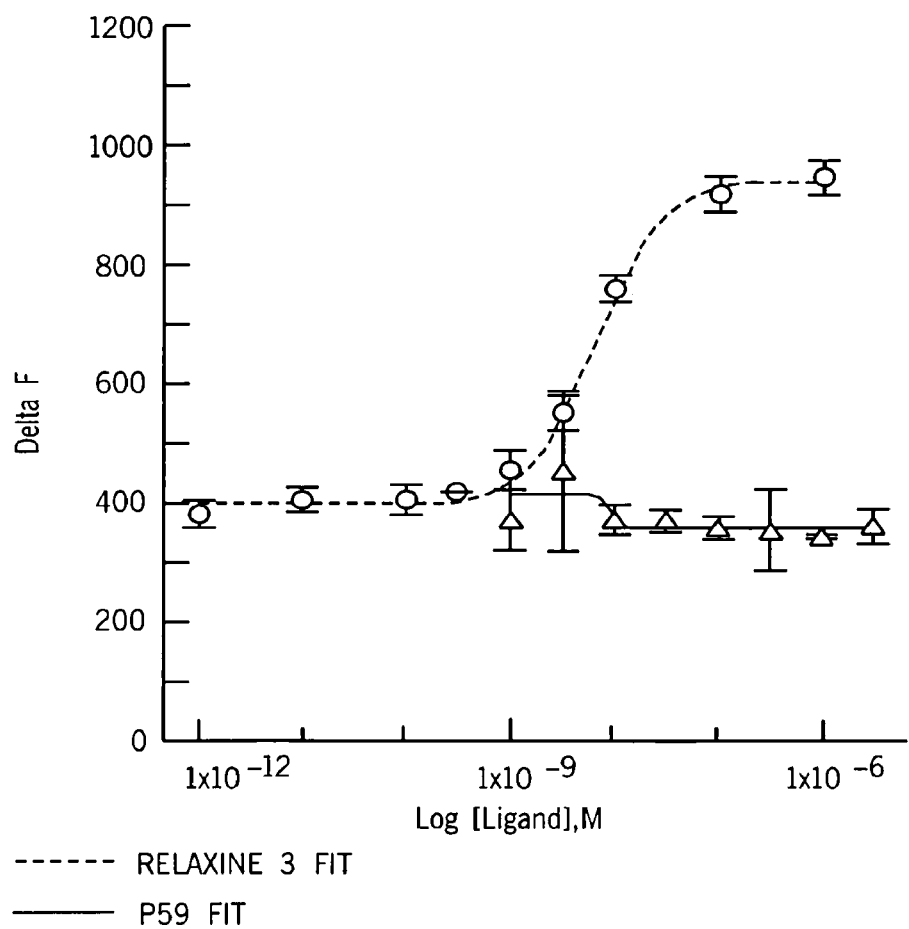
FIG. 5 is a graph showing Gs (cAMP increase) dose response activation of Euroscreen recombinant cell lines expressing the RXFP3 receptor (Cat: D88437, assay cat: ES-656-MG). The cAMP dose response was compared between Relaxin 3 (positive control) and P59C13V (P59) at concentrations of 1 pM-1 uM for Relaxin 3 and 1 nM-10 uM for P59C13V (P59).

Relaxin 3 Fit (Euroscreen) was used as a positive control. RXFP3 (GPCR135) transfected cells were challenged with increasing concentrations of Relaxin 3 (H3 Relaxin—as a positive control—1 pM-1 uM) or P59C13V (P59) (SEQ ID NO: 6) (1 nM-3 uM). The results are shown in FIG. 5. As can be seen from FIG. 5, P59C13V (P59) (SEQ ID NO: 6) didn't show any cAMP activation (Gs) of RXFP3, while a strong cAMP stimulation was demonstrated by H3 Relaxin.

In this experiment the P59C13V (P59) (SEQ ID NO: 6) did not activate a cAMP stimulation effect on RXFP3 transfected CHO-K1 cells. However, without wishing to be bound by theory, the P59C13V (P59) (SEQ ID NO: 6) peptide can either bind or activate a different pathway when applied on RXFP3 transfected cells. This experiment does not rule out the possibility that the P59C13V (P59) (SEQ ID NO: 6) might activate a Gi or a different G-protein mediated effect on RXFP3 receptor, nor determine the effect of and of the other peptides on this receptor (i.e. SEQ. ID. No. 1-5 or 7-15).

EXAMPLE 5

Activity of P74 (SEQ ID NO: 10) and P59 (SEQ ID NO: 6) in Cells Expressing LGR7OR LGR8 Together with pCRE-β-gal In order to further test the activity of P59C13V (P59) (SEQ ID NO: 6), P59S-Amide (P59S) (SEQ ID NO: 1), P59C13V-Amide (P59Amide) (SEQ ID NO: 5) and P74C13V (P74) (SEQ ID NO: 10), the following assay was performed. The assay was done to assess the ability of P59C13V (P59) (SEQ ID NO: 6), P59S-Amide (P59S) (SEQ ID NO: 1), P59C13V-Amide (P59Amide) (SEQ ID NO: 5) and P74C13V (P74) (SEQ ID NO: 10) peptides to replace H2 Relaxin or INSL3 activity in stable HEK-293T cell lines expressing the LGR7 (RXFP1) or the LGR8 (RXFP2) receptors, respectively, by assessment of the ability of these peptides to increase cAMP activity in cell lines expressing LGR7 (RXFP1) or LGR8 (RXFP2) respectively, together with pCRE-β-gal. The pCRE-β-gal assay is a standard and well established assay at the Howard Florey Institute (Melbourne, Australia) (Halls M L, Bathgate R A, Summers R J. —Comparison of signaling pathways activated by the relaxin family peptide receptors, RXFP1 and RXFP2, using reporter genes. J Pharmacol Exp Ther. 2007 January; 320(1):281-90.)

The ability of P59C13V (P59) (SEQ ID NO: 6), P59S-Amide (P59S) (SEQ ID NO: 1), P59C13V-Amide (P59Amide) (SEQ ID NO: 5) and P74C13V (P74) (SEQ ID NO: 10) to influence cAMP activity in HEK-293T LGR7/pCRE-β-gal stable or LGR8/pCRE-β-gal transfected cells was tested in parallel to H2 relaxin and INSL3 respectively, according to the protocol described in Halls M L, et al., J Pharmacol Exp Ther. 2007 January; 320(1):281-90.

The experiment was repeated at least three times. The following concentrations of each peptide were tested: 0.01 nM, 0.1 nM, 1 nM, 10 nM, 100 nM, 1 μM.

No activation was shown for any of the peptides on LGR7/pCRE-β-gal transfected HEK-293T cells (data not shown).

Figure 6A:
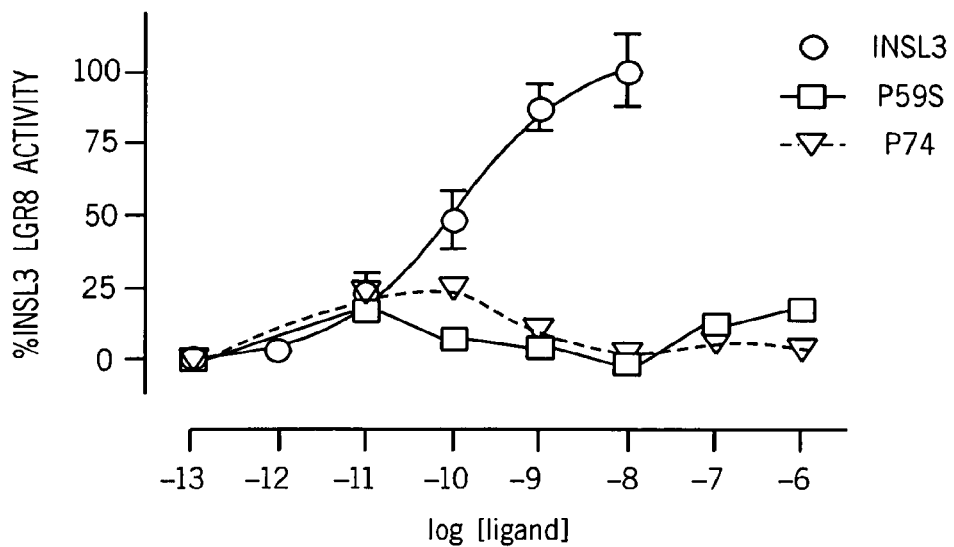
FIGS. 6A-B are graphs showing cAMP responsive element reading (CRE) in response to stimulation of LGR8 expressing HEK293 cells to INSL3 (as a positive control) and the peptides P59-S amide and P74C13V (P74) (FIG. 6A); or P59C13V (P59) and P59C13V-amide (P59-amide)) (FIG. 6B). The X axis represents the peptide concentration (log) and the Y axis represents the CRE activation relative to INSL3 max activity (in %).
Figure 6B:
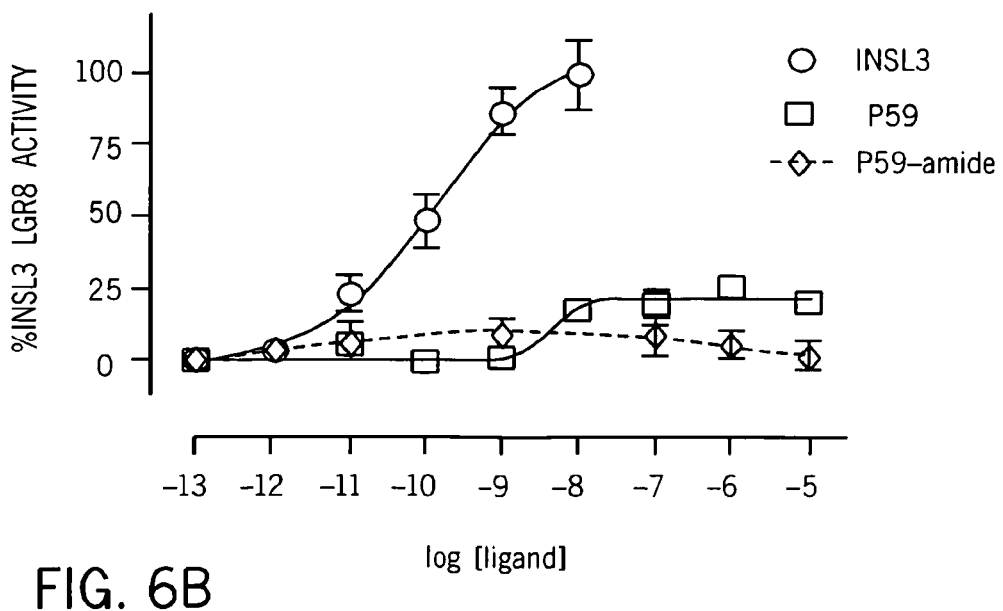

The results demonstrating activation of LGR8 by P74C13V (SEQ ID NO: 10), P59C13V with (P59-Amide) (SEQ ID NO: 5) and without (P59) amide (SEQ ID NO: 6) and P59S-Amide (SEQ ID NO: 1), are shown in FIGS. 6A and 6B. The results are presented as a percentage of INSL3 activity in LGR8/pCRE-β-gal transfected HEK-293T cells as a function of the concentration (Represented in Log [M]).

FIG. 6A demonstrates a bell shaped response of LGR8/pCRE-β-gal transfected HEK-293T cells to P74C13V (SEQ ID NO: 10) in all three of the assays. The P59S-Amide (SEQ ID NO: 1) effect was less pronounced. FIG. 6B shows that P59C13V (P59) (SEQ ID NO: 6) demonstrates a weak activation effect (~25% of INSL3) on LGR8/pCRE-β-gal transfected HEK-293T cells, while P59C13V-amide (P59-Amide) (SEQ ID NO: 5) had a very weak effect.

The ability of P74C13V (P74) (SEQ ID NO: 10) and P59C13V (P59) and P59C13V-Amide (P59-Amide) (SEQ ID NO: 6 and 5 respectively) to activate LGR7 (RXFP1) and LGR8 (RXFP2) was further tested by testing the ability of these peptides to influence cAMP activity induced by 5 μM Forskolin in CHO-K1 cells transiently transfected with LGR7/pCRE-β-gal or LGR8/pCRE-β-gal as compared to H2 relaxin and INSL3 respectively.

LGR7 transfected CHO-K1 cells were treated with 5 uM of Forskolin to stimulate cAMP. The cells were then challenged with increasing doses of H2 Relaxin (as positive control), P74C13V (P74) (SEQ ID NO: 10), P59C13V with (P59-Amide) and without (P59) amide and P59S-Amide (P59S) (SEQ ID NO: 5, 6 and 1, respectively). The results demonstrating the effect of P74C13V (P74) (SEQ ID NO: 10), P59C13V with (P59-Amide) and without (P59) amide (SEQ ID NO: 5 and 6, respectively) and P59S-Amide (SEQ ID NO: 1) on LGR7/pCRE-β-gal transiently transfected CHO-K1 cells is presented in FIGS. 7A and 7B. The results are presented as a percentage of Forskolin activity at increasing concentrations of each peptide (represented in log [M]). The baseline for the experiment was the activity of Forskolin alone (100%). Each point represents three unrelated repeats for each experiment together with their standard error bars.

Figure 7A:
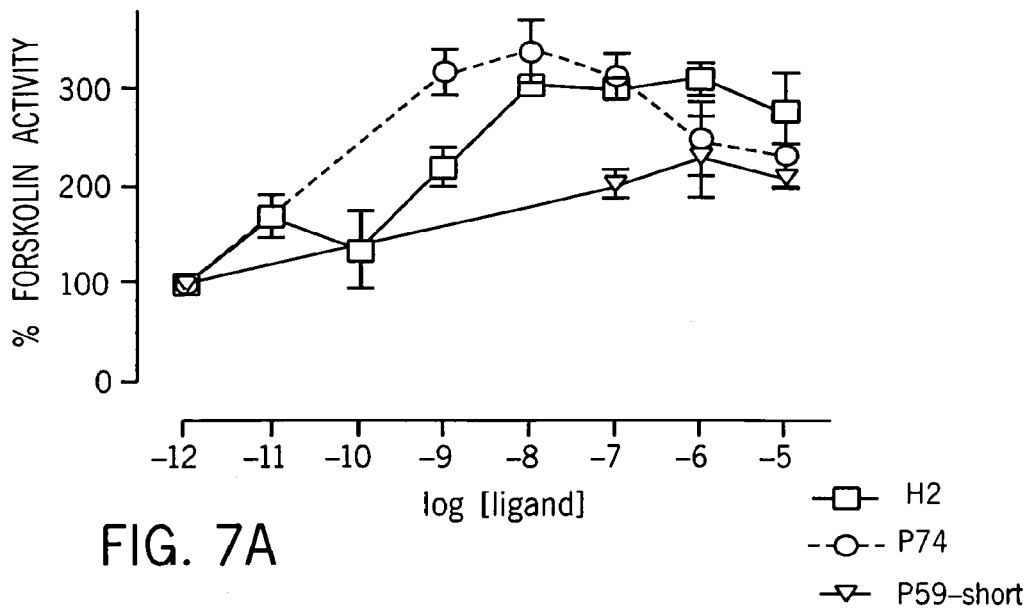
FIGS. 7A-B are graphs showing cAMP responsive element reading (CRE) in response to stimulation of LGR7 expressing CHO-K1 cells to pre treatment with 5 uM of Forskolin and H2 relaxin (H2) as a positive control compared with the peptides P59-S amide and P74C13V (P74) (FIG. 7A); or P59C13V (P59) and P59C13V-amide (P59-amide) (FIG. 7B). The X axis represents the peptide concentration (log) and the Y axis represents the CRE activation relative to the base line Forskolin activity (in % where 100% is with no peptide treatment). This graph is the average result of three independent experiments (N=3).

FIG. 7A presents a bell-shaped activation pattern shown by P74C13V (P74) (SEQ ID NO: 10) on LGR7/pCRE-β-gal transiently transfected CHO-K1 cells. The activation of P74C13V (P74) (SEQ ID NO: 10) seems to be stronger than that of H2 Relaxin at the lower concentrations (as was already demonstrated in FIGS. 4A and 4B), whereas H2 Relaxin showed an increased activation at higher concentrations. P59S-Amide (SEQ ID NO: 1) showed a mild activation (of only ~X2 or Forskolin) at higher concentrations only (100 nM and 1-10 uM)

Figure 7B:
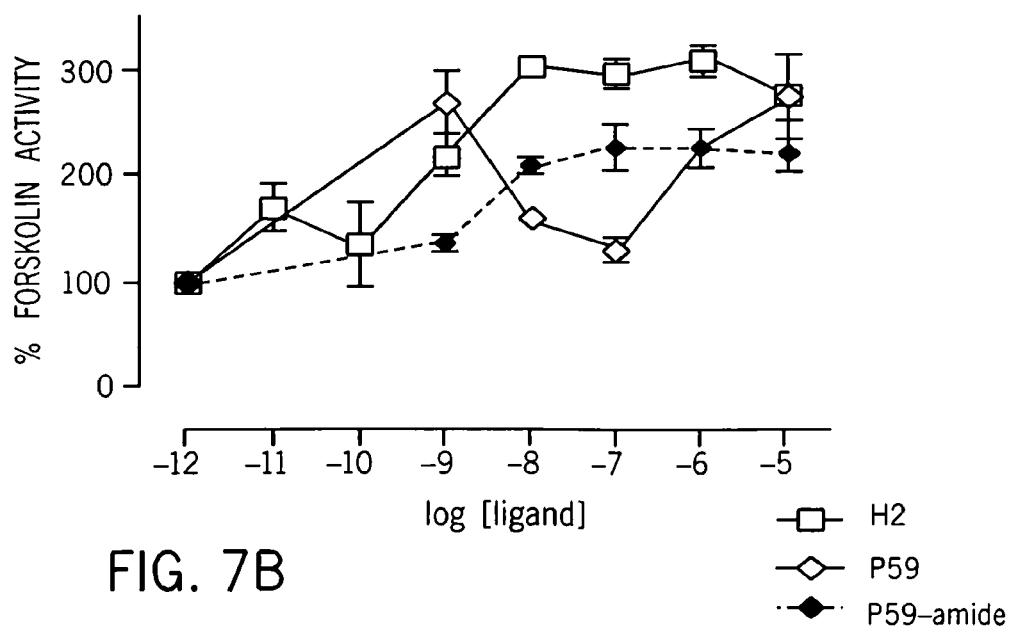

FIG. 7B presents a dual activation pattern effect, demonstrating an activation peak at lower concentrations and second peak in cAMP activation at higher concentrations, shown by P59C13V (P59) (SEQ ID NO: 6); and a slight activation pattern shown by P59C13V-amide (P59-Amide) (SEQ ID NO: 5) on LGR7/pCRE-β-gal transiently transfected CHO-K1 cells.

LGR8 transfected CHO-K1 cells were treated with 5 uM of Forskolin to stimulate cAMP. The cells were then challenged with increasing doses of INSL3 (as positive control), P74C13V (P74) (SEQ ID NO: 10), P59C13V with (P59-Amide) and without (P59) amide (SEQ ID NO: 5 and 6, respectively) and P59S-Amide (P59-S) (SEQ ID NO: 1). The results demonstrating the effect of P74C13V (P74) (SEQ ID NO: 10), P59C13V with (P59-Amide) and without (P59) amide (SEQ ID NO: 5 and 6, respectively) and P59S-Amide (P59S-Amide) (SEQ ID NO: 1) on LGR8/pCRE-β-gal transiently transfected CHO-K1 cells is presented in FIGS. 8A and 8B. The results are presented as a percentage of Forskolin activity at various concentrations of the peptide (logarithmic scale). Each point represents three unrelated repeats for each experiment.

Figure 8A:
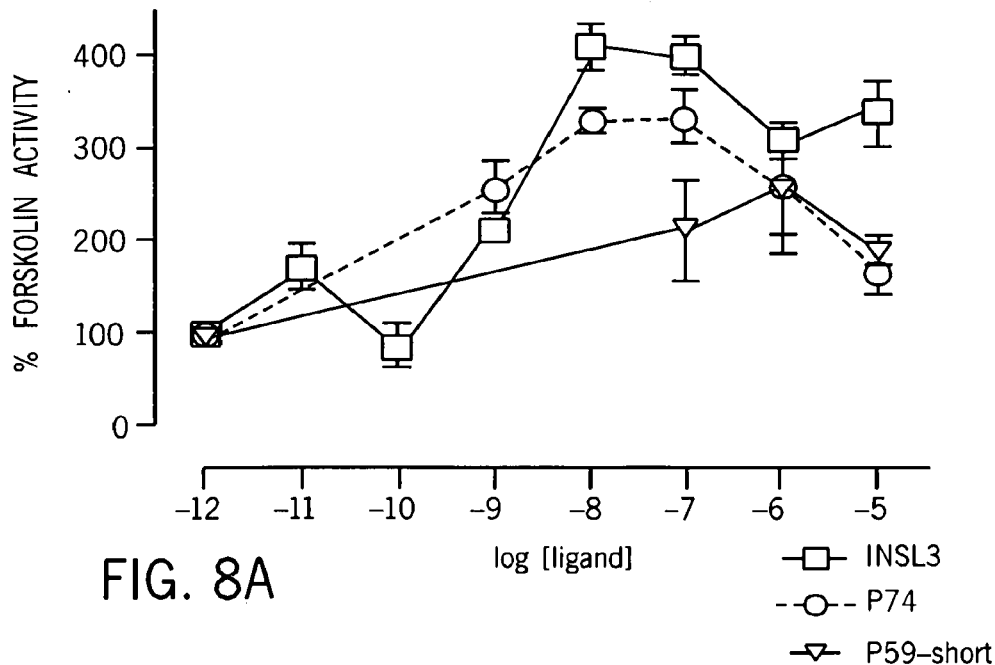
FIGS. 8A-B are graphs showing cAMP responsive element reading (CRE) in response to stimulation of LGR8 expressing CHO-K1 cells to pre treatment with 5 uM of Forskolin and INSL3 as a positive control compared with the peptides P59-S amide and P74C13V (P74) (FIG. 8A); or P59C13V (P59) and P59C13V-amide (P59-amide) (FIG. 8B). The X axis represents the peptide concentration (log) and the Y axis represents the CRE activation relative to the base line Forskolin activity (in % where 100% is with no peptide treatment). This graph is the average result of three independent experiments (N=3).

FIG. 8A presents a bell-shaped activation pattern, shown by P74C13V (P74) (SEQ ID NO: 10) similar to that of INSL3 at lower concentrations on LGR8/pCRE-β-gal transiently transfected CHO-K1 cells. The activation of P74C13V (P74) (SEQ ID NO: 10) seems to be similar yet slightly weaker than that or INSL3 at the lower concentrations (as was already demonstrated in FIGS. 7A for LGR7), whereas INSL3 showed an increased activation at higher concentrations.

P59S-Amide (SEQ ID NO: 1) showed a mild activation (of only ~X2 or Forskolin) at higher concentrations only (100 nM and 1-10 uM).

Figure 8B:
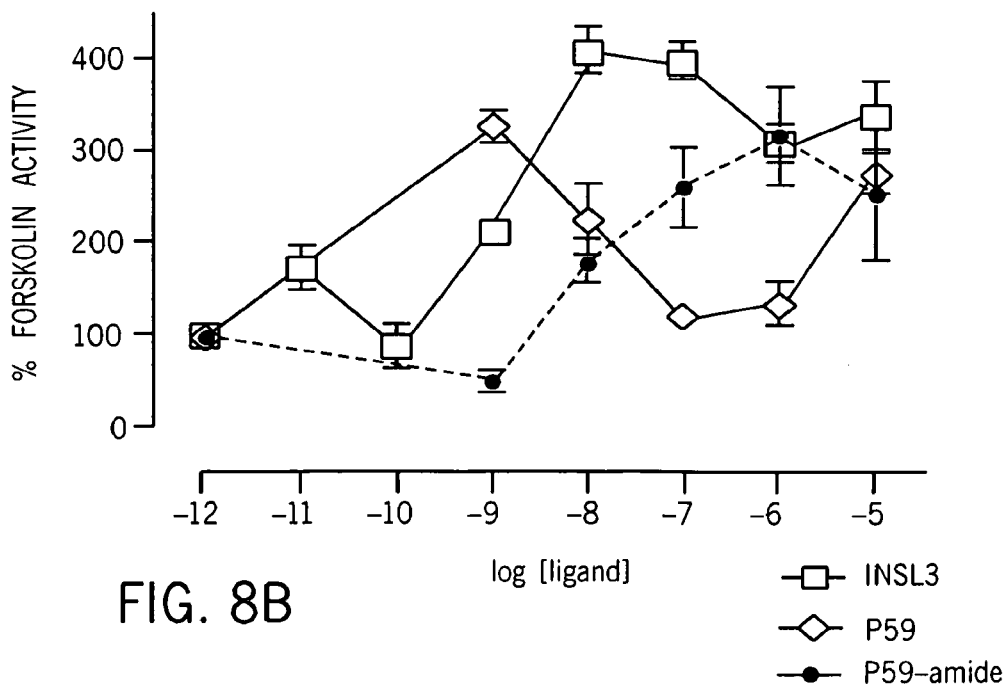

FIG. 8B presents a dual activation pattern effect, demonstrating a peak in activation at lower concentrations and second increase in cAMP activation at higher concentrations shown by P59C13V (P59) (SEQ ID NO: 6); and a slight activation pattern shown by P59C13V-amide (P59-Amide) (SEQ ID NO: 5) on LGR8/pCRE-β-gal transiently transfected CHO-K1 cells.

EXAMPLE 6

Competition Assays of P74C13V (SEQ ID NO: 10) and P59C13V (SEQ ID NO: 6) with Europium Labelled H2 Relaxin or INSL3 in Cells Expressing LGR7 or LGR8

The ability of Peptides P74C13V (SEQ ID NO: 10) and P59C13V (SEQ ID NO: 6) to compete with the binding of known ligands to LGR7 or LGR8 was tested by testing the ability of P74C13V (SEQ ID NO: 10) and P59C13V (SEQ ID NO: 6) to compete with the binding of Europium labelled H2 Relaxin or INSL3 (manufactured by the H. Florey institute) to stable HEK-293T cell lines expressing LGR7 or LGR8 respectively.

Figure 9:
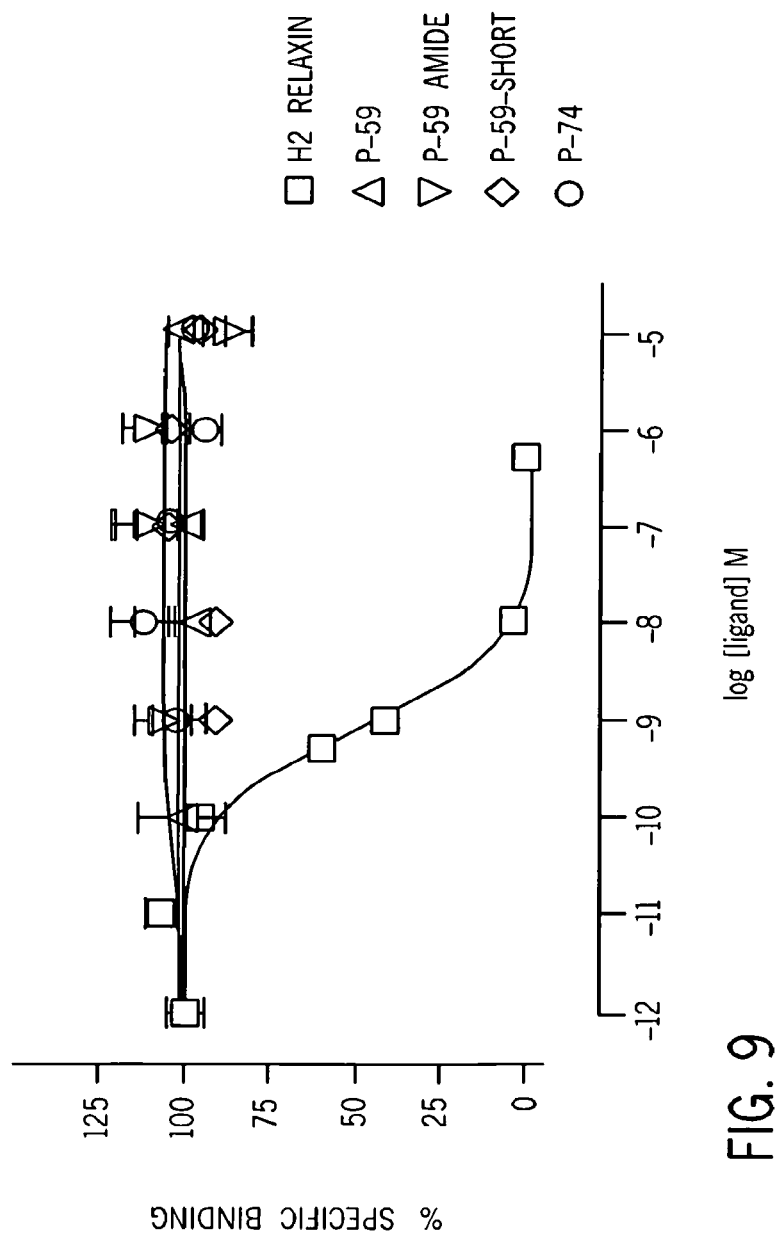
FIG. 9 is a graph showing competitive binding of LGR7 between a Europium (radioactive) conjugated Relaxin (H2) and either non-radioactive H2 relaxin and each of the peptides: P59-S-amide, P74C13V (P74), P59C13V (P59) and P59C13V-amide (P59-amide). The X axis represents the peptide concentration (log) and the Y axis represents the specific binding represented by radioactivity (%).

HEK-293T cell lines stabely expressing LGR7 (RXFP1) were treated with Europium labelled H2 Relaxin (manufactured by the H. Florey institute) The cells were then treated with decimal increasing concentrations (0.01 nM, 0.1 nM, 1 nM, 10 nM, 100 nM, 1 μM, 10 μM) of un-labeled H2 Relaxin (as a positive control) and the tested peptides P59C13V (P59) (SEQ ID NO: 6), P59C13V-Amide (P59-Amide) (SEQ ID NO: 5), P59-S-Amide (P59S) (SEQ ID NO: 1) and P74C13V (P74) (SEQ ID NO: 10). The competition results of three independent experiments are shown in FIG. 9. The binding results are shown as a percentage of specific binding of the radioactive test H2 Relaxin (where 100% is the baseline radiation level). As can be seen from FIG. 9, no competition was shown for the binding of Europium-H2 Relaxin by any of the tested peptides. Without wishing to be bound by a single theory, the activity of peptides P59C13V (SEQ ID NO: 6), P59C13V-Amide (SEQ ID NO: 5), P59S-Amide (SEQ ID NO: 1) and P74C13V (SEQ ID NO: 10) on LGR7 (RXFP1), might be mediated by binding of the peptides to a different binding site, since the binding of the above peptides does not interfere, compete or affect the binding of the Europium H2 Relaxin to LGR7.

Figure 10:
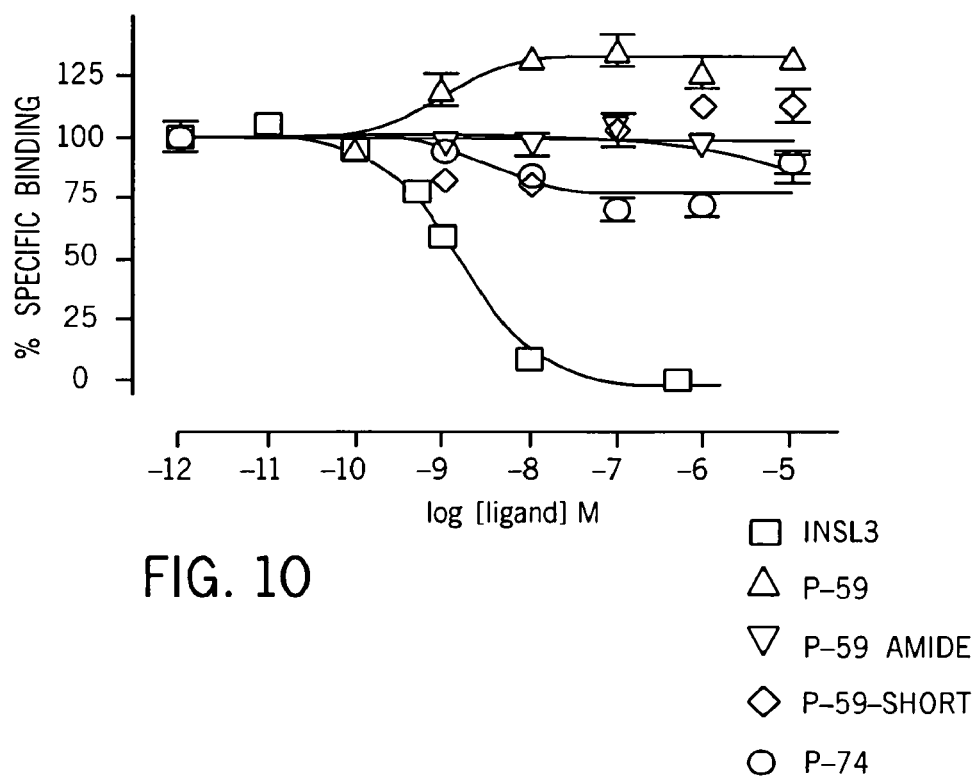
FIG. 10 is a graph showing competitive binding of LGR8 between a Europium (radioactive) conjugated INSL3 and either non-radioactive INSL3 and each of the peptides: P59-S-amide, P74C13V (P74), P59C13V (P59) and P59C13V-amide (P59-amide). The X axis represents the peptide concentration (log) and the Y axis represents the specific binding represented by radioactivity (%).

HEK-293T cell lines expressing LGR8 (RXFP2) were treated with Europium labled INSL3 (manufactured by the H. Florey institute). The cells were then treated with decimal increasing concentrations (0.01 nM, 0.1 nM, 1 nM, 10 nM, 100 nM, 1 μM, 10 μM) of un-labeled INSL3 (as a positive control) and the tested peptides P59C13V (P59) (SEQ ID NO: 6), P59C13V-Amide (P59-Amide) (SEQ ID NO: 5), P59-S-Amide (P59S) (SEQ ID NO: 1) and P74C13V (P74) (SEQ ID NO: 10). The competition results of three independent experiments are shown in FIG. 10. The binding results are shown as a percentage of specific binding of the radioactive test INSL3 (where 100% is the baseline radiation level). As can be seen from FIG. 10, P59C13V (P59) (SEQ ID NO: 6) demonstrates a positive cooperative or allosteric effect, showing ~125% of specific binding at 1 nM and higher concentrations. This means that the binding affinity of the Eur-INSL3 was increased by binding/activity of the P59C13V (P59) (SEQ ID NO: 6) peptide on the LGR8 receptor. The results with the other peptides (P59C13V-amide (P59-Amide) (SEQ ID NO: 5), P59-S-Amide (P59S) (SEQ ID NO: 1) and P74C13V (P74) (SEQ ID NO: 10)) were less apparent but all four peptides showed alteration and competition/allosteric effect on the binding of Europium-INSL3 on LGR8 (RXFP2). Without wishing to be bound by a single theory, the binding of the peptides to the LGR8 receptor, probably through a different binding site than that of INSL3, there is an allosteric effect that might alter the affinity of the receptor to the INSL3 ligand, might suggesting a synergistic effect of the above peptides and INSL3 on the activity of the LGR8 (RXFP2) receptor.

EXAMPLE 7

Real Time Activation Assay Tested by ACEA Cell Impedance System

Method for Analysis of Peptides' Ability to Activate Relaxin-Related Family of Receptors Using ACEA RT-CES Screen
ACEA RT-CES Screen Background:

ACEA RT-CES screen is a noninvasive and label-free assay for GPCRs that can be used with both engineered and nonengineered cell lines. The assay is based on using cell-electrode impedance to measure minute changes in cellular morphology as a result of ligand-dependent GPCR activation and is described in Naichen Yu, et al., Anal. Chem., 78 (1), 35-43, 2006. 10.1021/ac051695v S0003-2700(05)01695-1. The Rho family of small GTPases, which include Rho, Rac, and CDC42, are well-characterized effectors of oncogenes, growth factor and adhesion-mediated signaling pathways and are not classically thought of as being key effectors for GPCRs. Rho family GTPases participate in a number of cellular processes, the main one being regulation and maintenance of specific structures within the actin cytoskeleton framework. GPCRs have been shown to modulate the actin cytoskeleton and hence cell morphology in a very specific manner depending on the Rho family GTPase being activated. The current view of the actin cytoskeleton is that of a dynamic and plastic system that is a reflection and manifestation of the intracellular signaling and not simply a static structure designed to maintain cellular architecture. Since GPCRs couple to the actin cytoskeletal network and induce very defined morphological changes, it is possible to harness this information as a functional and biologically relevant readout for GPCRs.

ACEA biosciences, has designed electronic cell sensor arrays embedded in the bottom of the well of microtiter plates that are capable of measuring minute changes in cell morphology. The electronic sensors measure changes in cell-substrate impedance as a result of the disruption of the ionic environment due to the presence of cell and cell morphology dynamics. The main advantages offered by using cell-substrate impedance and cell morphology as a readout are that both exogenously expressed and endogenous receptors can be assayed without the need for engineering the cell with promiscuous G proteins and reporters or labeling the cells with dyes. In addition, since the readout is noninvasive, multiple stimulations with the same ligand or different ligands can be performed to assess events such as desensitization and receptor cross-talk. Finally, another major aspect of using cell-substrate impedance and cell morphology as a readout is that potentially all GPCRs, regardless of the signaling pathways, can be functionally monitored.
ACEA RT-CES Screen Experimental Procedure & Protocol Peptides were synthesized by the solid phase peptide synthesis (SPPS) method, cleaved from the resin, and purified by RP-HPLC unless stated otherwise. The peptide's identity was verified by mass spectrometry. Final purity of peptide was >90% as measured by RP-HPLC. Peptides were diluted in Water (DDW—high purity) containing 0.1% BSA. In some cases peptides were dissolved in Tris-HCl buffer (pH8.2). In other cases either the addition of 1% DMSO or s brief sonication was required. All plates were stored at −80 C until use.

Cells:

CHOk1 cell-line (ATCC CCL-61). Cells were maintained and propagated in F-12 HAM nutrient mix (Gibco. Cat#21765-029) supplemented with 10% HI-FBS (Biological Ind. Cat#04-121-1), 2.5 mL of 200 mm L-Glutamine in Saline Solution (Biological Ind. Cat#03-020-1), 5 mL of Penicillin-Streptomycin Solution 10000/mL Penicillin G & 10 mg/mL Streptomycin Sulfate (Biological Ind. Cat#03-031-1).

Subculturing Cells:

Cells were freshly thawed from liquid N2 and were subcultured 1:10 twice a week according to the following protocol:

Remove and discard culture medium.

Briefly rinse the cell layer with 0.25% (w/v) Trypsin-0.53 mM EDTA solution to remove all traces of serum which contains trypsin inhibitor.

Incubate for 5 minutes at 37° C. in CO2 humidified incubator.

Examine under the microscope until cell layer is dispersed.

Add 10 to 12 mL of complete growth medium and aspirate cells by gently pipetting.

Take a 300 µl sample from the cell suspension and count concentration, viability and aggregate rate using the CEDEX counter.

Centrifuge cells for 6 minutes at 1200 rpm.

Re-suspend cells in complete growth medium to the desirable cell concentration.

DNA Transfection:

All transfections were performed using the FUGENE6 reagent (Roche. Cat#11-814-443-001, Expiry date: May 2008).

Transfection Protocol:

One day before the transfection 2×106 CHO-k1 cells were plated in T75 flask containing 10 mL of complete growth medium. On the transfection date, FUGENE6 transfection reagent was warmed to ambient temperature by 15 minutes incubation at room temperature and mixed prior to use by vortex.

The following was diluted in a sterile microfuge tube: 50 µl of FUGENE6 into 650 µl of serum free F12-HAM medium and tubes were incubated for 10 min at RT.

The transfected DNA mix was prepared in another sterile microfuge tube; Total of 20 µg plasmid DNA mixture which is composed of 18 µg of the target GPCR plasmid and of 2 µg of pIRES plasmid carrying eGFP reporter gene.

The plasmids DNA mixture was then added to the transfection reagent tube and incubated 35 min at RT with gently tapping once every 5 minutes to mix the contents. The DNA-FuGene complex was added drop wise to flask and spread by gentle swirling.

The transfected cells were kept for 24 hours at 37° C. in CO2 humidified incubator and monitored under fluorescent microscope for the detection of green light omitted from GFP transfected cells.

ACEA RT-CES Protocol; Screening for GPCR Activating Peptides:

In this protocol the RCD96 E-plate device (ACEA Biosciences Inc.) were used for seeding, monitoring and activating the CHO-k1 transfected cells.

Pre-treatment E-Plates: The E-plate wells were coated with 100 uL of 1 mg/ml Gelatine (Fluka. Cat#48720). The gelatine was dissolved at 8 mg/mL in sterile DDW and was diluted 1:8 in DDW before added to the E-plate wells. The plates covered with gelatine were incubated for 40 minutes at 37° C. and 5% CO2 in a humidified atmosphere.

100 µl of sterile water were added and all liquids were removed. The plates were washed twice more, now with 200 µl of sterile water and plate was taken for cells seeding Cells Seeding:

Before the transfected cells were seeded, 80 ml SFM F12-HAM medium were added to each well of the E-plates and background levels were recorded.

24-26 hours past transfection, medium was aspirated and cells were trypsinized with 0.25% (w/v) Trypsin/EDTA solution and counted on the CEDEX counter.

Total cell number was calculated and cells were re-suspended in complete growth medium to cell concentration ranging from 0.3125×106/mL up to 0.4375×106/mL. From that dilution, 80 µl of cell suspension were seeded, resulting in 25,000 up to 35000 total cells in 5% FCS-complete growth medium per each E-plate well.

Peptide Challenging:

22-26 hours past seeding (46-52 hours past transfection) and with concordance to the recorded Cell Index (CI) the cells were prepared for the addition of the activating peptides. Prior to adding the peptides, the complete medium was aspirated and replaced with 120 ml 37° C. pre-warmed SFM F12-HAM nutrient mixture.

1 hour later or when the CI reads are stabilized, the E-plate was removed from the 96X E-Plate Station for peptide challenge. Challenging with the peptides was performed in duplicates by adding 5 µl of peptide solution from an already made 250 µM daughter stock plates, resulting in final peptide concentration of 10 µM. The peptide solution contains the peptide dissolved in DDW supplemented with 0.1% Albumin (Sigma-aldrich Cat# A3059, Fraction V, ~99%, Essentially γ-globulin free).

The screening was done on transiently transfected CHO-K1 cells and was done in two stages:
1. Screening phase—Challenging the relaxin-related family of receptors transfected CHO-K1 cells with 10 uM of each screened peptide, using Calcitonin (1 uM) as an assay internal positive control (the receptor for Calcitonin is endogenously expressed by CHO-K1 cells), 0.1% BSA as a negative control. 1 uM of H2 Relaxin was used as a positive control for the transfected receptor.
2. Dose response phase—Challenging the LGR7 transfected CHO-K1 with 0.03 uM, 0.1 uM, 0.3 uM, 1 uM, 3 uM and 10 uM of each screened peptide, using H2 Relaxin as a positive control for the transfected receptor.

EXAMPLE 7-1

P74 (SEQ ID NO: 10) and P59 (SEQ ID NO: 6) Mediated Activation of the LGR-Related Family of Receptors in ACEA Cell Impedance Device—Screening Phase The ability of Peptides P74C13V (P74) (SEQ ID NO: 10) and P59C13V (P59) (SEQ ID NO: 6) to activate LGR7 (RXFP1) and LGR8 (RXFP2) receptors was checked as described above in ACEA cell impedance device. The following results were obtained:

First the ability of Peptide P74C13V (SEQ ID NO: 10) (at 10 uM) and H2 Relaxin (at 1 uM) to cause changes in cell impedence was measured in untransfected CHO-K1 cells.

Figure 11:
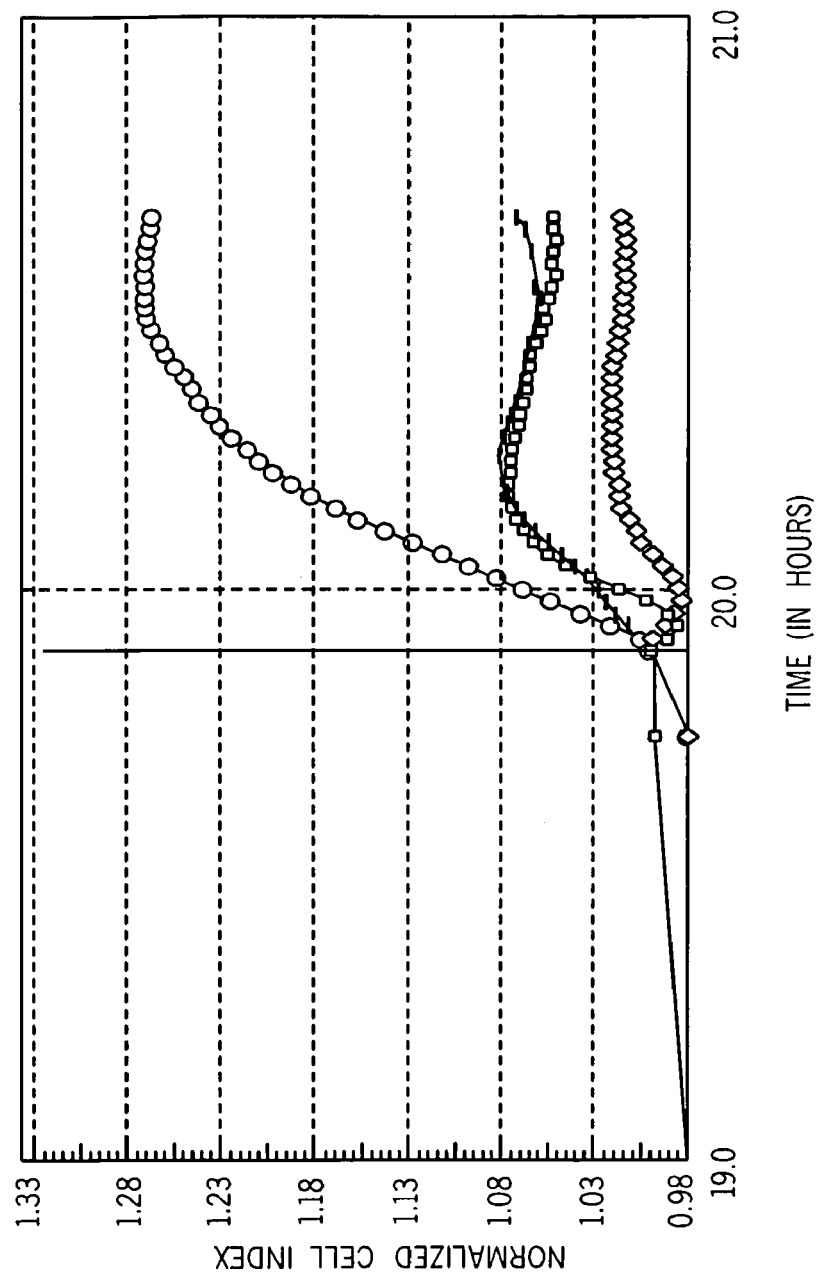
FIG. 11 is a graph showing the cell impedance and cytoskeleton remodeling effect (measured by ACEA RT-CES system) of H2 Relaxin (1 uM), P74C13V (P74-10 uM), 0.1% BSA (as a negative control) and 1 uM of Calcitonin (a ligand for CalcR a GPCR endogenously expressed on CHO-K1 cells, as a positive internal control) on Untransfected CHO-K1 cells. The X axis represents time of experiment (challenge time is indicated by a vertical line), and the Y axis represents the cell index (a measurement of the change in Cell impedance) normalized to the peptide challenge time. The code is as follows: circles represent calcitonin 1 uM; short horizontal lines represents H2 1 uM; squares represent P74 10 uM; and diamond shapes represent BSA 0.1%.

The results are presented in FIG. 11. Cell index was normalized to time point T1 (after peptide administration), marked in FIG. 11 by a vertical solid line (The dashed Vertical line indicates the 20$^{th}$ hour from the beginning of the experiment). Calcitonin was used as an internal positive control to evaluate the validity of the assay, as the calcitonin receptor is endogenously expressed on CHO-K1 cells. BSA 0.1% was used as a negative control. As can be seen from FIG. 11, both H2 Relaxin and peptide P74C13V (P74) demonstrated a moderate effect on untransfected CHO-K1 cells. Without wishing to be bound by a single theory, the conclusion from this result is that even though not detected at standard procedures, either the LGR7 or LGR8 receptors are expressed, even if in a residual amount, by the CHO-K1 cell line.

Figure 12:
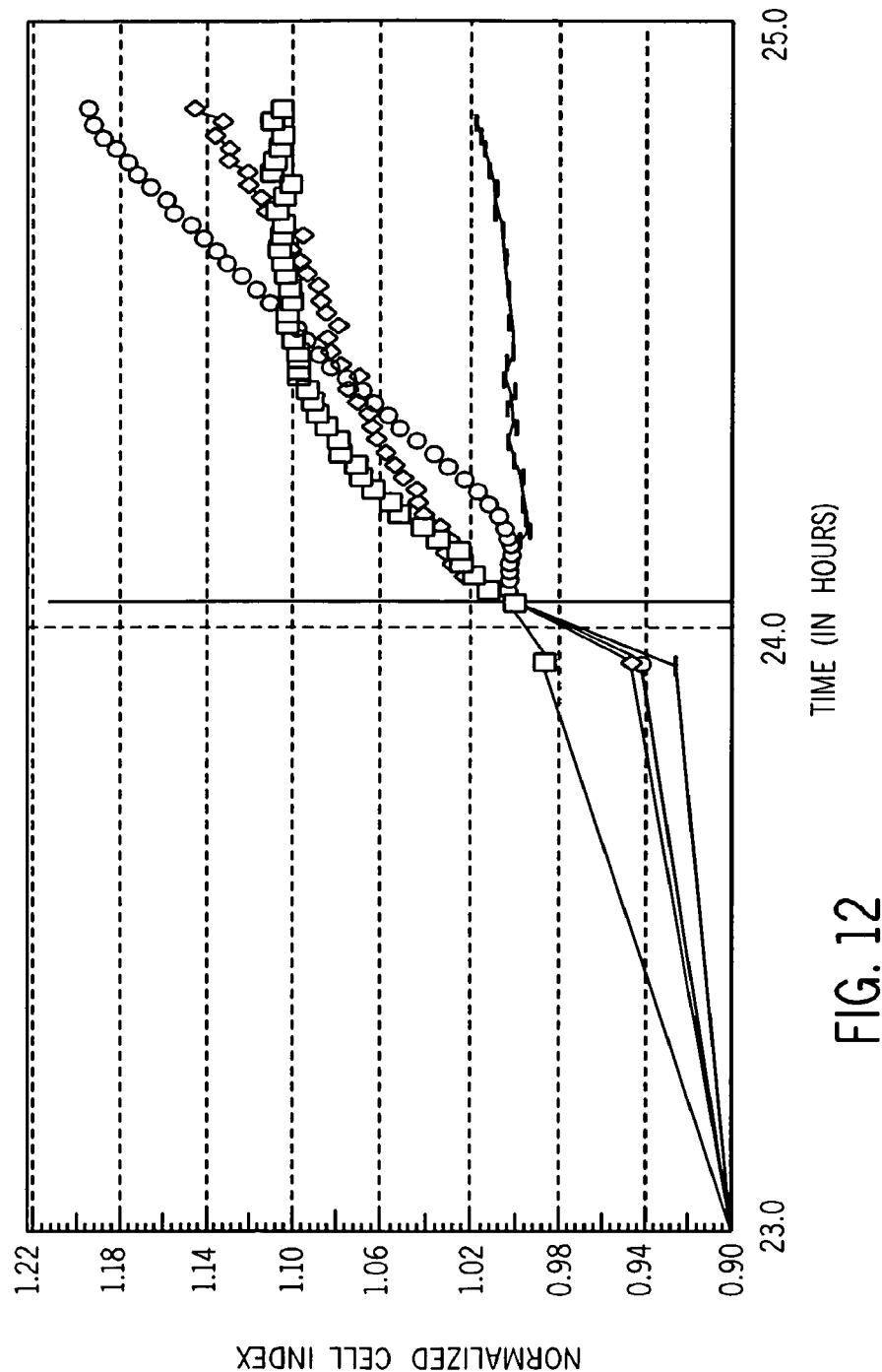
FIG. 12 is a graph showing the cell impedance and cytoskeleton remodeling effect (measured by ACEA RT-CES system) of H2 Relaxin (1 uM), P74C13V (P74-10 uM), 0.1% BSA (as a negative control) and 1 uM of Calcitonin (a ligand for CalcR a GPCR endogenously expressed on CHO-K1 cells, as a positive internal control) on GPR39 (a non relaxin related GPCR) transfected CHO-K1 cells. The X axis represents time of experiment (challenge time is indicated by a vertical line), and the Y axis represents the cell index (a measurement of the change in Cell impedance) normalized to the peptide challenge time. The code is as follows: circles represent calcitonin 1 uM; diamond shapes represent P74, 10 uM; squares represent H2, 1 uM; and short horizontal lines represent BSA 0.1%.

Next, the ability of Peptide P74C13V (P74) (SEQ ID NO: 10) (at 10 uM) and H2 Relaxin (at 1 uM) to cause changes in cell impedence was measured in CHO-K1 cells transfected with a non-relaxin related GPCR: GPR39 (GPR39_Human in SwissProt accession: O43194). The results are presented in FIG. 12. Cell index was normalized to time point T1 (after peptide administration), marked in FIG. 12 by a vertical solid line (the dashed vertical line indicates the 24$^{th}$ hour from the beginning of the experiment). Calcitonin was used as a positive control and BSA 0.1% was used as a negative control. As can be seen from FIG. 12, both H2 Relaxin and peptide P74C13V (P74) (SEQ ID NO: 10) demonstrated a moderate yet visible effect on GPR39 transfected CHO-K1 cells.

From these experiments, it can be seen that the transfection process itself was not the cause for the response presented above (in FIG. 11).

Figure 13:
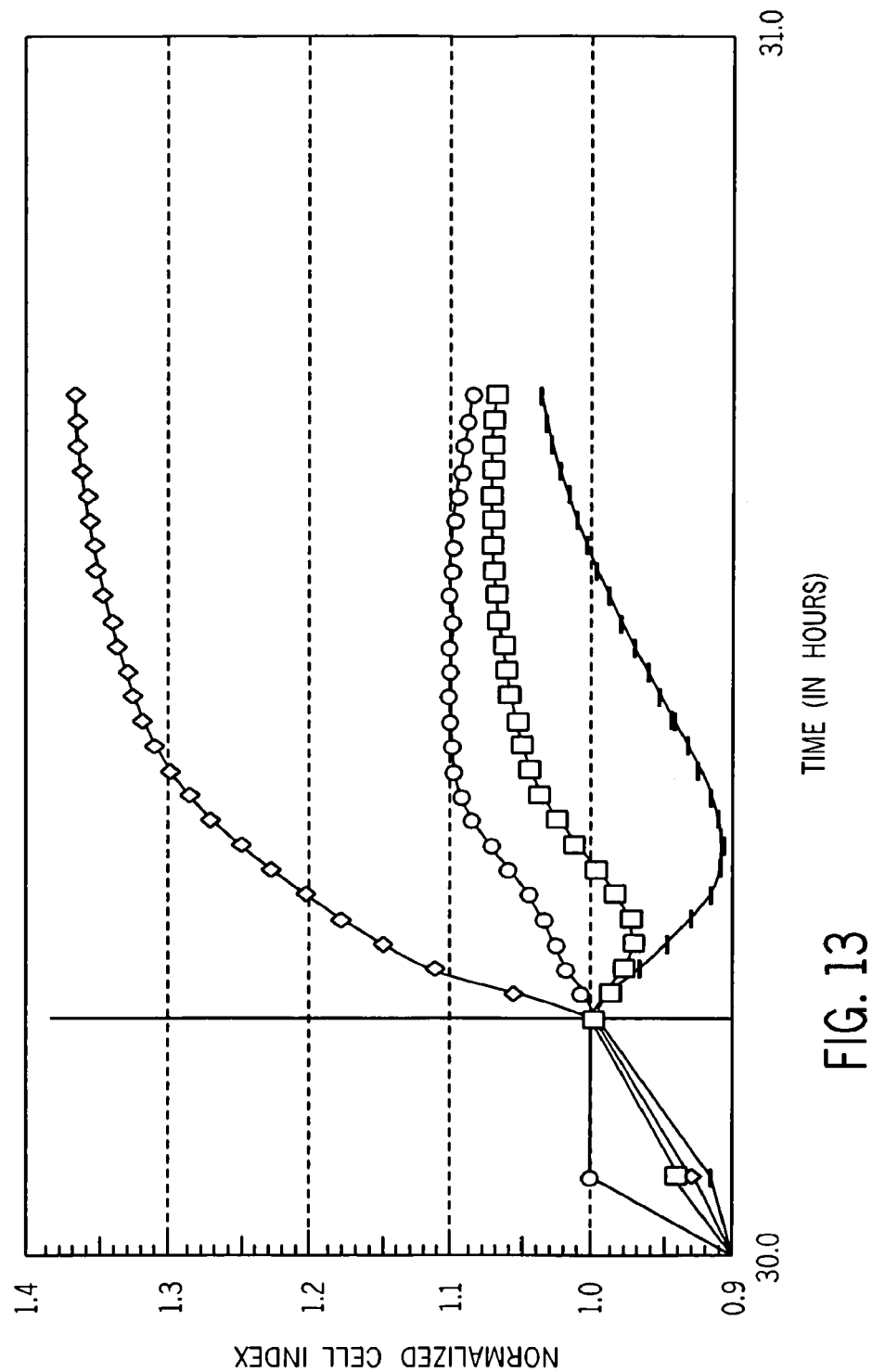
FIG. 13 is a graph showing the cell impedance and cytoskeleton remodeling effect (measured by ACEA RT-CES system) of H2 Relaxin (1 uM), P74C13V (P74-10 uM), 0.1% BSA (as a negative control) and 1 uM of Calcitonin (a ligand for CalcR a GPCR endogenously expressed on CHO-K1 cells, as a positive internal control) on LGR7 (RXFP1) transfected CHO-K1 cells. The X axis represents time of experiment (challenge time is indicated by a vertical line), and the Y axis represents the cell index (a measurement of the change in Cell impedance) normalized to the peptide challenge time. The code is as follows: diamond shapes represent P74, 10 uM; circles represent H2, 1 uM; short horizontal lines represent calcitonin 1 uM; and squares represent BSA 0.1%.

Next, the ability of Peptide P74C13V (P74) (SEQ ID NO: 10) (at 10 uM) and H2 Relaxin (at 1 uM) to cause changes in cell impedence was measured in CHO-K1 cells transfected with a LGR7 (RXFP1). The results are presented in FIG. 13. Cell index was normalized to time point T1 (after peptide administration), marked in FIG. 13 by a vertical solid line. Calcitonin was used as a positive control and BSA 0.1% was used as a negative control. As can be seen from FIG. 13, both H2 Relaxin and peptide P74C13V (SEQ ID NO10) demonstrated a cellular cell impedance (as shown by the ACEA measurement) effect on LGR7 transfected CHO-K1 cells. The effect of P74C13V (SEQ ID NO: 10) was stronger than the effect of H2 Relaxin, however, both peptides (H2 Relaxin and P74C13V (SEQ ID NO10)) were found to be capable of activating a cellular response in LGR7 transfected CHO-K1 cells.

Figure 14:
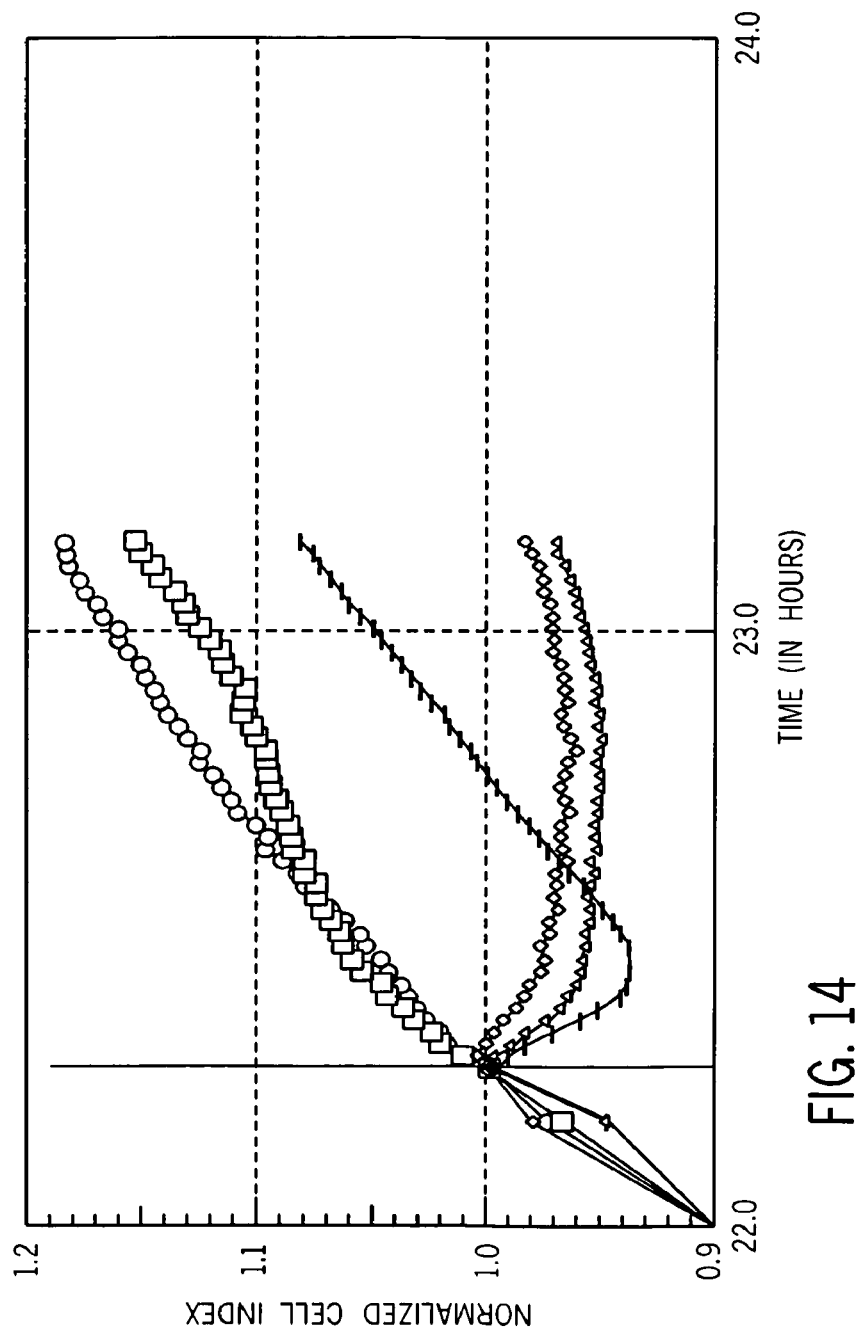
FIG. 14 is a graph showing the cell impedance and cytoskeleton remodeling effect (measured by ACEA RT-CES system) of H2 Relaxin (1 uM), P74C13V (P74-10 uM), P59C13V (P59), 0.1% BSA (as a negative control) and 1 uM of Calcitonin (a ligand for CalcR a GPCR endogenously expressed on CHO-K1 cells, as a positive internal control) on LGR8 (RXFP2) transfected CHO-K1 cells. The X axis represents time of experiment (challenge time is indicated by a vertical line), and the Y axis represents the cell index (a measurement of the change in Cell impedance) normalized to the peptide challenge time. The code is as follows: diamond shapes represent P59, 1 uM; circles represent H2, 1 uM; short horizontal lines represent calcitonin 1 uM; squares represent P74, 10 uM; and triangles represent BSA 0.1%.

The ability of Peptides P74C13V (P74) (SEQ ID NO: 10) (at 10 uM), P59C13V (P59) (SEQ ID NO: 6) (at 10 uM) and H2 Relaxin (at 1 uM) to cause changes in cell impedence was further measured in CHO-K1 cells transfected with a LGR8 (RXFP2). The results are presented in FIG. 14. As above, cell index was normalized to time point T1 (after peptide administration), marked in FIG. 14 by a vertical solid line (the dashed Vertical line indicates the 23$^{rd}$ hour from the beginning of the experiment). As above, Calcitonin was used as a positive control and BSA 0.1% was used as a negative control. As can be seen from FIG. 14, both H2 Relaxin and peptide P74C13V (SEQ ID NO: 10) demonstrated a strong cellular effect on LGR8 transfected CHO-K1 cells. P59C13V (P59) (SEQ ID NO: 6) showed no significant effect as compared to BSA. From these results it seems that both peptides (H2 Relaxin and P74C13V (SEQ ID NO: 10)) are capable of activating a cellular response in LGR8 transfected CHO-K1 cells, however, no effect of P59C13V (P59) (SEQ ID NO: 6) on LGR8 transfected CHO-K1 cells was demonstrated in this experiment. This could be explained by technical problem, such as degradation of the P59 peptide in this experiment.

Figure 15:
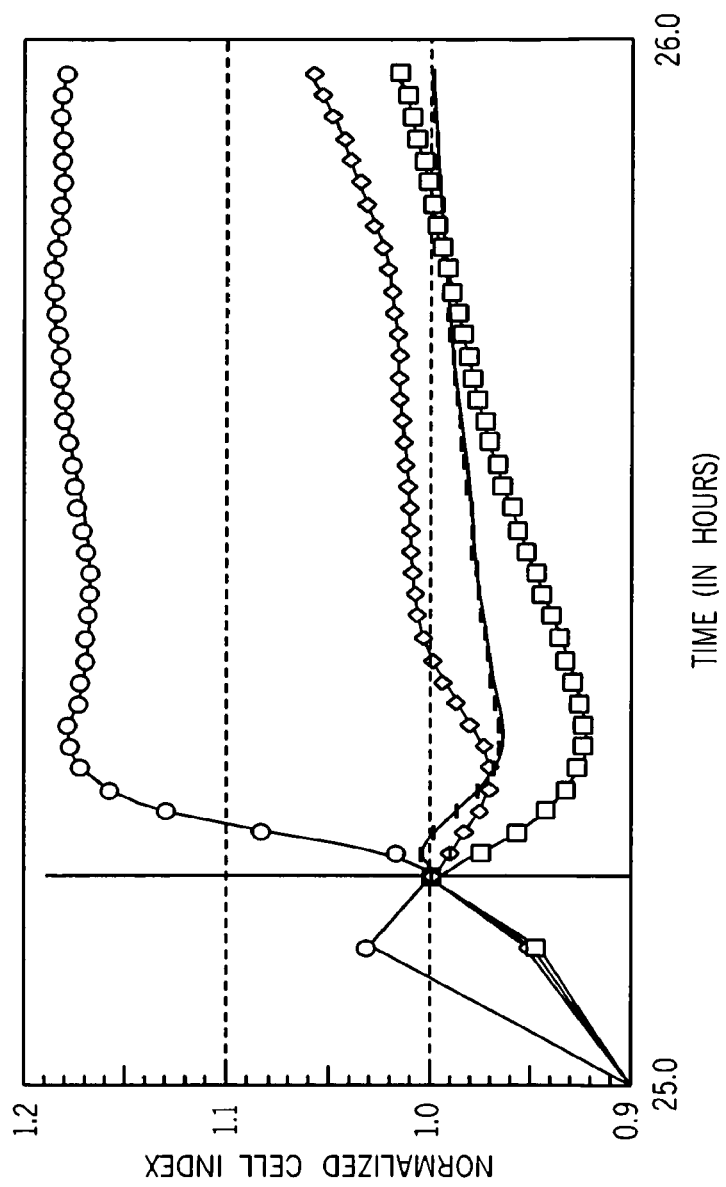
FIG. 15 is a graph showing the cell impedance and cytoskeleton remodeling effect (measured by ACEA RT-CES system) of H2 Relaxin (1 uM), P74C13V (P74-10 uM), 0.1% BSA (as a negative control) and 1 uM of Calcitonin (a ligand for CalcR a GPCR endogenously expressed on CHO-K1 cells, as a positive internal control) on LGR4 (Orphan) transfected CHO-K1 cells. The X axis represents time of experiment (challenge time is indicated by a vertical line), and the Y axis represents the cell index (a measurement of the change in Cell impedance) normalized to the peptide challenge time. The code is as follows: circles represent P74, 10 uM; diamond shapes represent H2, 1 uM; squares represent calcitonin 1 uM; and short horizontal lines represent BSA 0.1%.

The ability of Peptide P74C13V (P74) (SEQ ID NO: 10) (10 uM) and H2 Relaxin (1 uM) to cause changes in cell impedance was further measured in CHO-K1 cells transfected with a LGR4. The results are presented in FIG. 15. As above, cell index was normalized to time point T1 (after peptide administration), marked in FIG. 15 by a vertical solid line. As above, Calcitonin was used as a positive control to and BSA 0.1% was used as a negative control. As can be seen from FIG. 15, peptide P74C13V (SEQ ID NO: 10) demonstrated a moderate effect on LGR4 transfected CHO-K1 cells. H2 Relaxin demonstrated a much stronger effect in this assay. Without wishing to be bound by a single theory, this result may suggest that H2 Relaxin is capable of binding and activating a cellular response though activation of the LGR4 receptor in LGR4 transfected CHO-K1 cells, probably mediated by a non cAMP related pathway.

EXAMPLE 7-1

P74 (SEQ ID NO: 10) and P59 (SEQ ID NO: 6) Mediated Activation of Relaxin-Related Family of Receptors in ACEA Cell Impedance Device—Dose Response Dose response activation testing of both (H2) Relaxin and P74C13V (P74) (SEQ ID NO: 10) in untransfected CHO-K1 cells showed no dose dependent activation but only a moderate activation of the highest concentrations (i.e. 10 uM for P74C13V and 1 uM for H2 Relaxin) (data not shown).

The experiment was done similarly to the ACEA protocol above. Each peptide was added in triplicates at increasing concentrations (presented in Log [M] on FIGS. 16B, 17B, 18B and 19B). Cell impedance was tested as described and cell index was normalized to the time of peptide addition (T1—left vertical line in FIGS. 16A, 17A, 18A and 19A). Dose response was examined at end point of the experiment (one time point—indicated by the right vertical line on FIGS. 16A-19A).

Figure 16A:
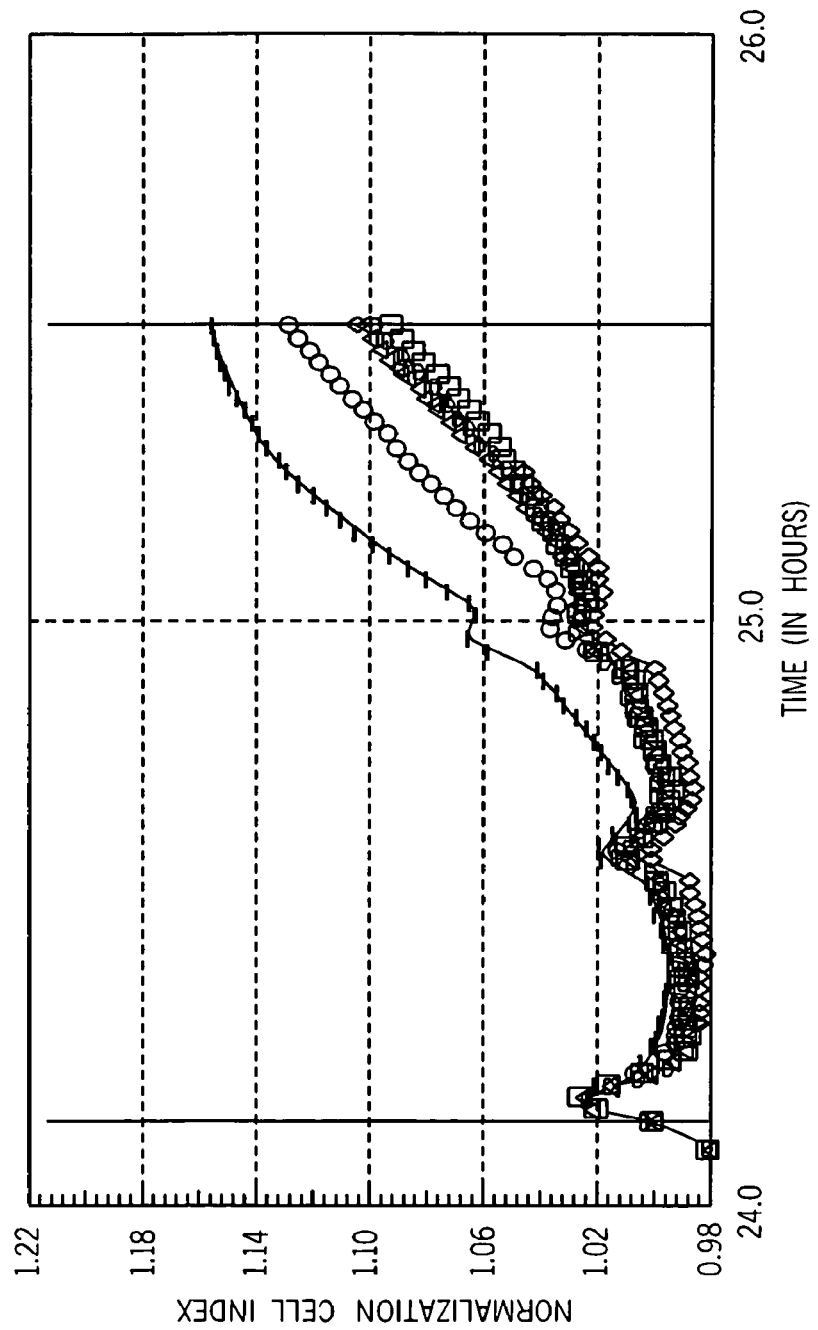
FIGS. 16A-B is a graph showing the cell impedance and cytoskeleton remodeling effect (measured by ACEA RT-CES system) as a dose dependant response of different concentrations of H2 Relaxin on LGR7 (RXFP1) transfected CHO-K1 cells.

FIG. 16A presents a normalized cell index and a dose response curve for LGR7 (RXFP1) transfected CHO-K1 cells challenged by increasing concentrations of H2 Relaxin (the dashed Vertical line indicates the 25$^{th}$ hour from the beginning of the experiment). The H2 Relaxin concentrations tested were 0.16 nM; 0.8 nM; 4 nM; 20 nM; 100 nM; 500 nM. As shown in FIG. 16A, there is a clear dose response for the higher concentrations, with an estimated EC50 of ~100 nM.

Figure 16B:
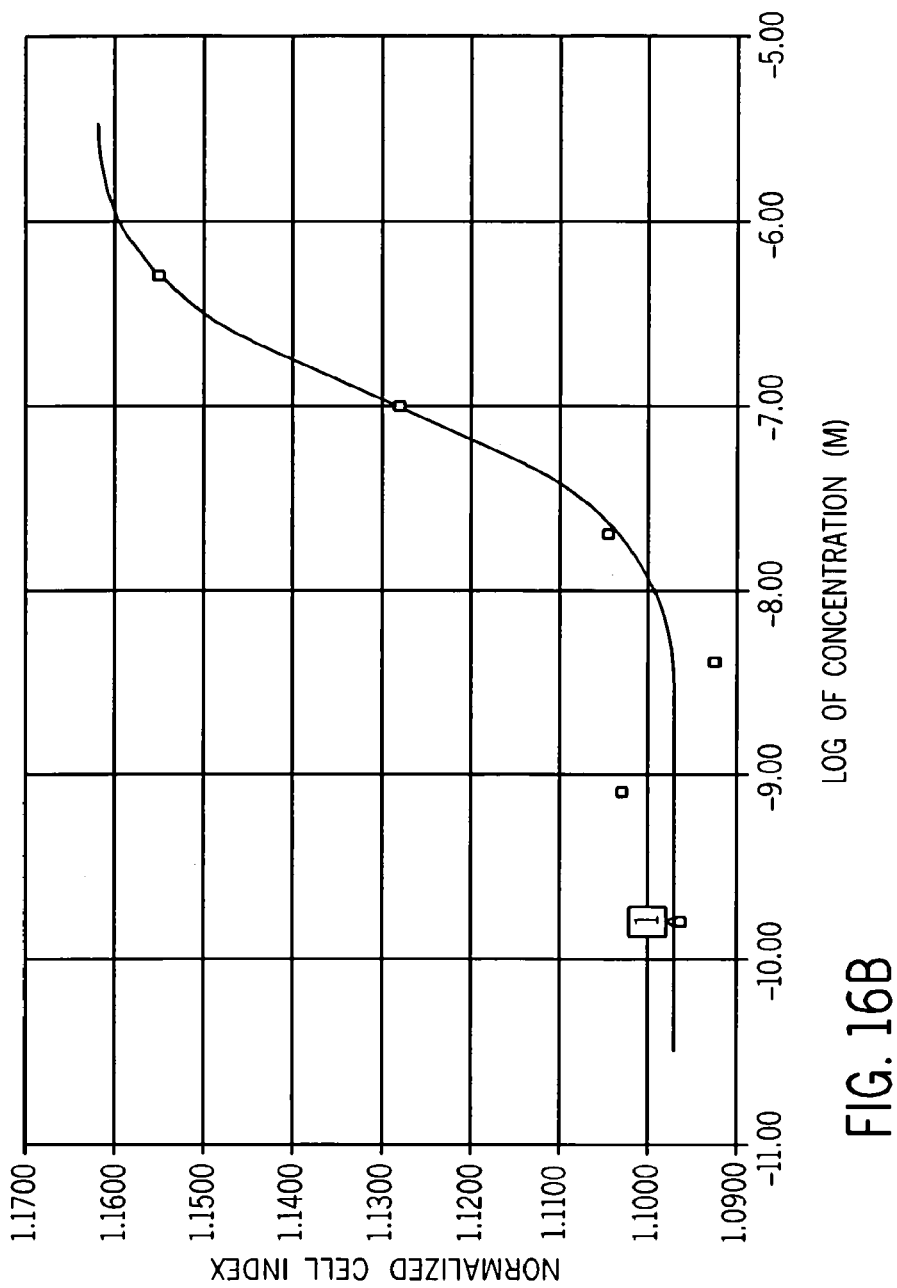

FIG. 16B presents a normalized cell index and a dose response curve for LGR7 transfected CHO-K1 cells challenged by increasing concentrations of H2 Relaxin at time point 25.5 hours (vertical right line in FIG. 16A). A dose response is presented as a normalized cell index per Log of concentration (M). As demonstrated in FIG. 16B, a clear dose dependent activation of LGR7 by H2 relaxin was found.

Figure 17A:
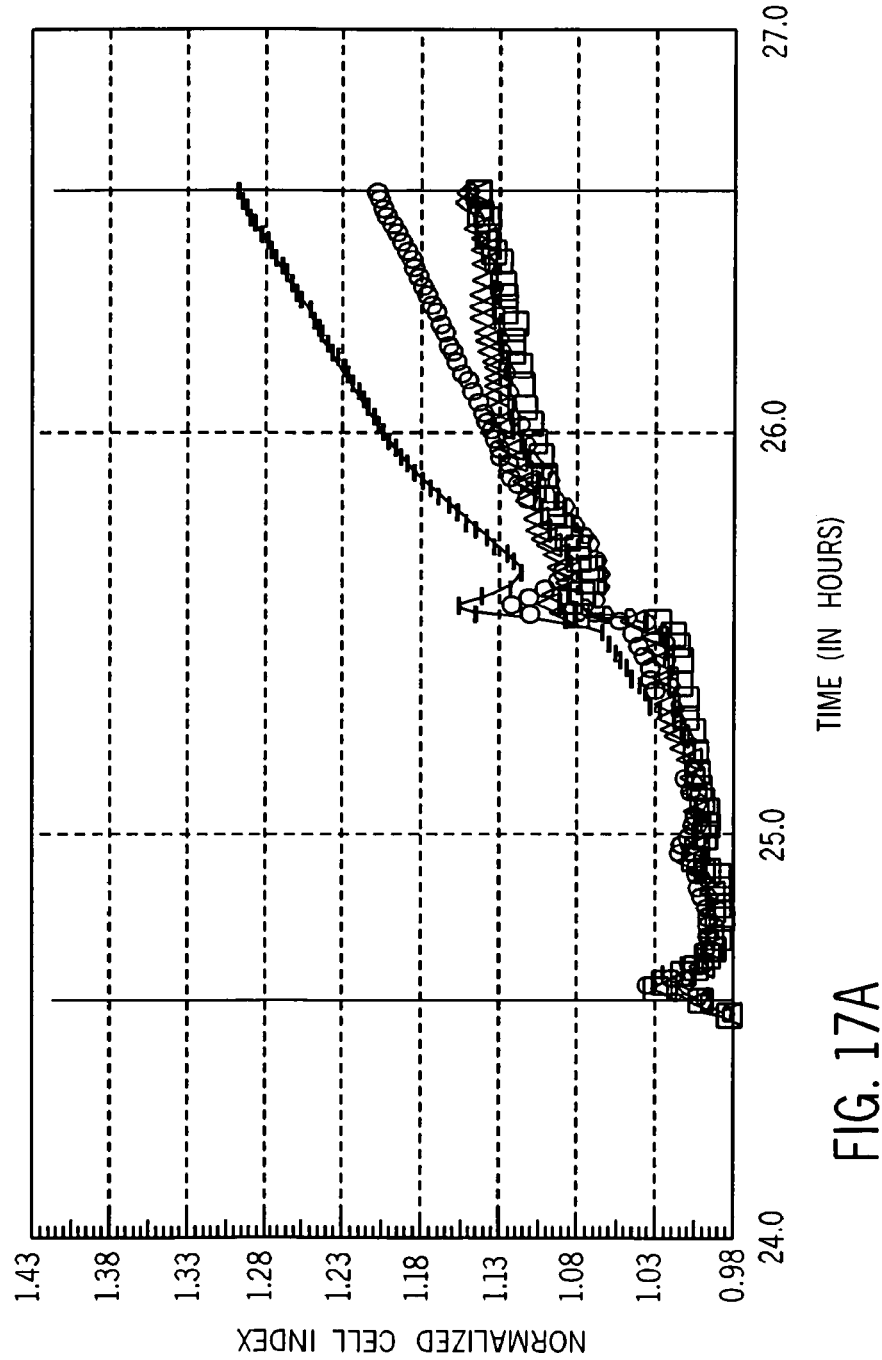
FIGS. 17A-B is a graph showing the cell impedance and cytoskeleton remodeling effect (measured by ACEA RT-CES system) as a dose dependant response of different concentrations of P74C13V (P74) on LGR7 (RXFP1) transfected CHO-K1 cells.

FIG. 17A presents a normalized cell index and a dose response curve for LGR7 (RXFP1) transfected CHO-K1 cells challenged by increasing concentrations of peptide P74C13V (P74) (SEQ ID NO:10) (the dashed Vertical lines indicate the 25$^{th}$ and 26$^{th}$ hours from the beginning of the experiment). The P74C13V (P74) (SEQ ID NO: 10) concentrations tested were 41 nM; 123 nM; 370 nM; 1.1 uM; 3.3 uM; 10 uM. As shown in FIG. 17A, there is a clear dose response for the high concentrations, with an estimated EC50 of ~300 nM.

Figure 17B:
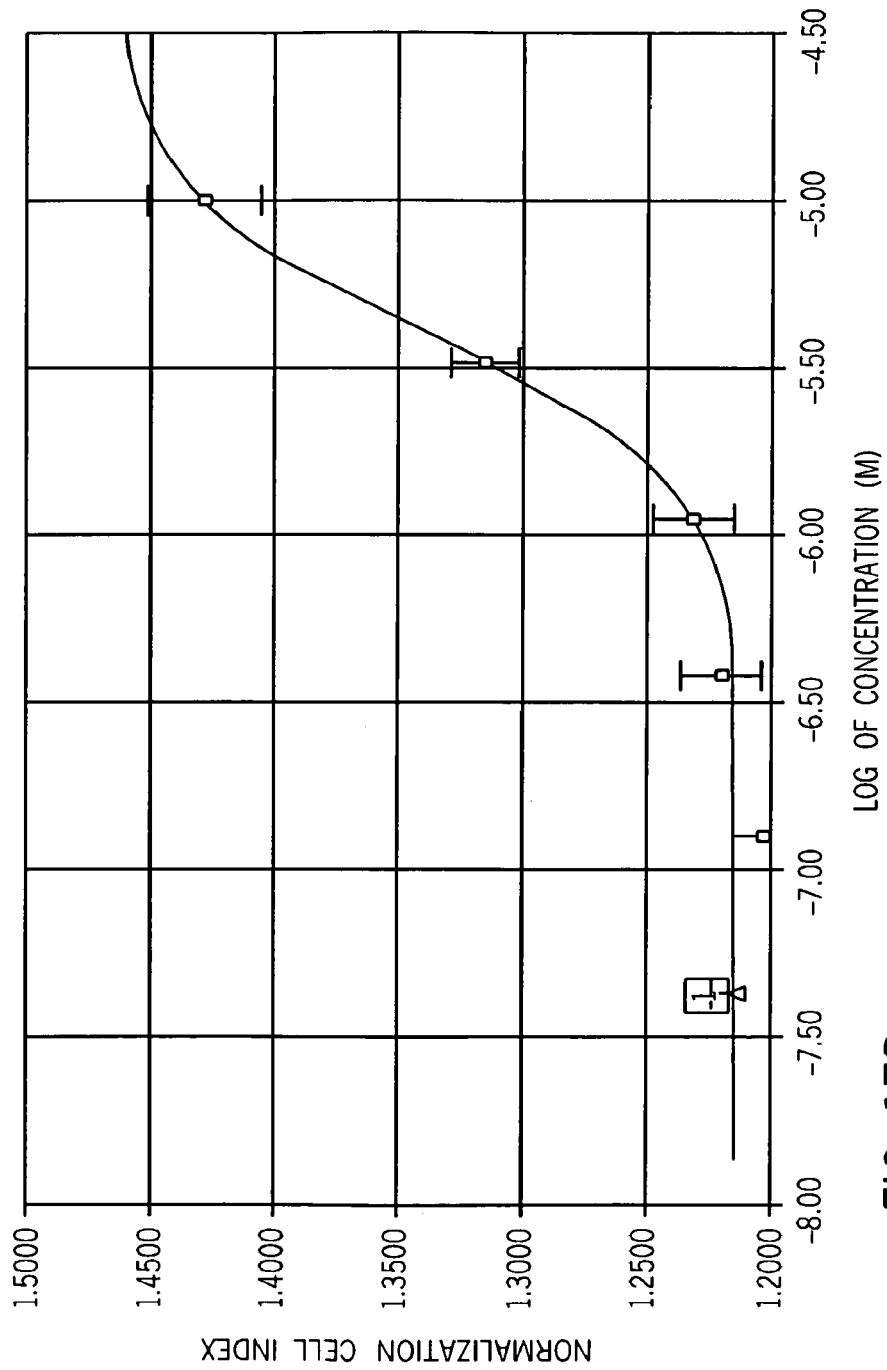

FIG. 17B presents a normalized cell index and a dose response curve for LGR7 transfected CHO-K1 cells challenged by increasing concentrations of peptide P74C13V (SEQ ID NO:10) at time point 26.5 hours (vertical right line in FIG. 17A). A dose response is presented as a normalized cell index per Log of concentration (M). As can be seen from FIG. 17B a clear dose dependent activation of LGR7 by P74C13V (SEQ ID NO:10) was found. The affinity found for P74C13V (SEQ ID NO:10) to LGR7 was lower than that of H2 Relaxin.

Figure 18A:
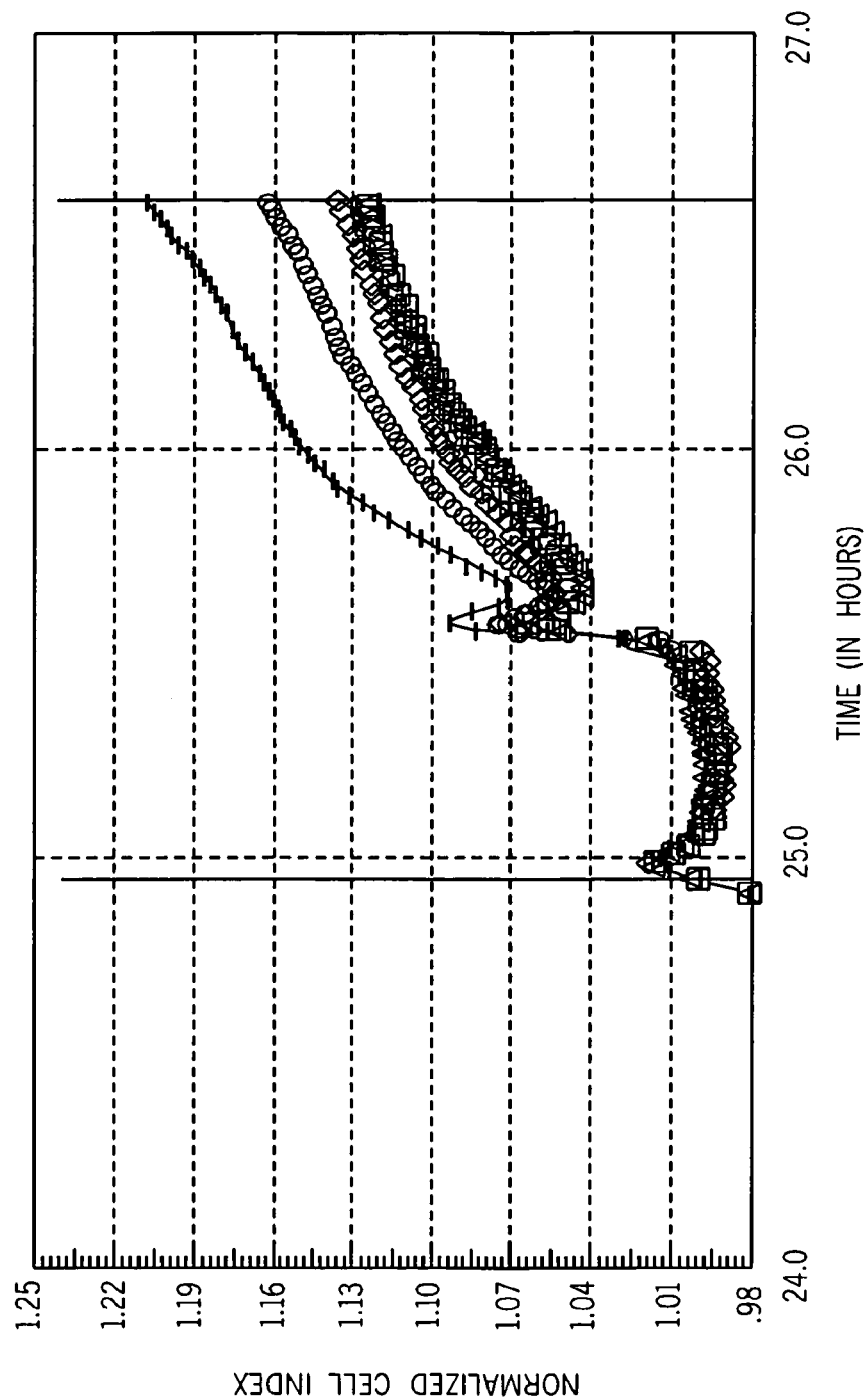
FIG. 18A-B is a graph showing the cell impedance and cytoskeleton remodeling effect (measured by ACEA RT-CES system) as a dose dependant response of different concentrations of P59C13V (P59) on LGR7 (RXFP1) transfected CHO-K1 cells.

FIG. 18A presents a normalized cell index and a dose response curve for LGR7 (RXFP1) transfected CHO-K1 cells challenged by increasing concentrations of peptide P59C13V (P59) (SEQ ID NO: 6) (the dashed Vertical lines indicate the 25$^{th}$ and 26$^{th}$ hours from the beginning of the experiment). The P59C13V (P59) (SEQ ID NO: 6) concentrations tested were 41 nM; 123 nM; 370 nM; 1.1 uM; 3.3 uM; 10 uM. As shown in FIG. 18A, there is a moderate dose response for the high concentrations.

Figure 18B:
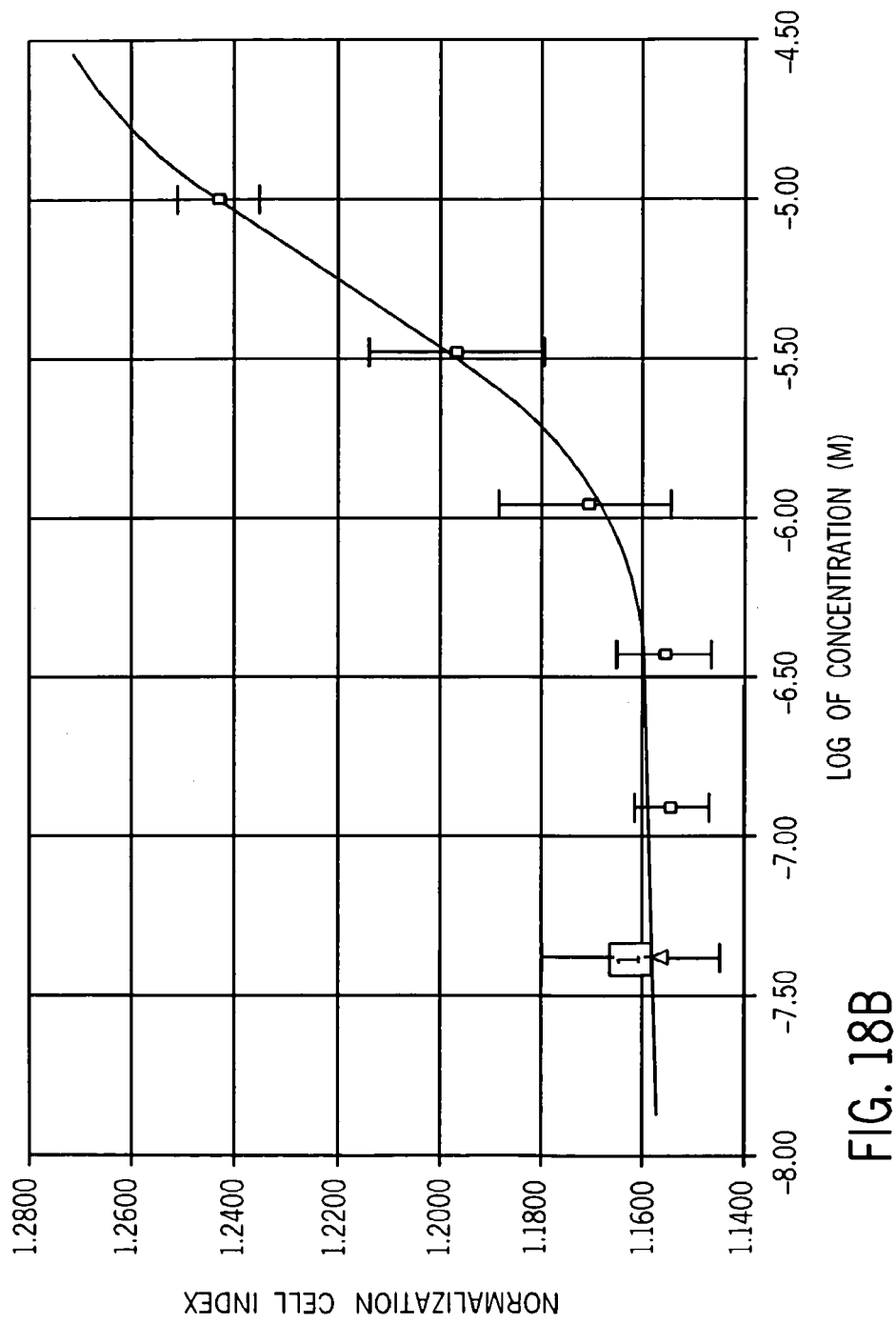

FIG. 18B presents a normalized cell index and a dose response curve for LGR7 transfected CHO-K1 cells challenged by increasing concentrations of P59 (SEQ ID NO:6) at time point 26.5 hours (vertical right line in FIG. 18A). A dose response is presented as a normalized cell index per Log of concentration (M). As can be seen from FIG. 18B a mild dose dependent activation of LGR7 by P59C13V (SEQ ID NO:6) was found. Only the highest concentration (10 uM) showed a significant higher cell index rate as compared to the other concentrations. Since the same peptide batch was used for this experiment and the experiment presented in FIG. 14 supports the assumption that this particular batch of P59C13V peptide was of bad quality. The affinity found for P59C13V (SEQ ID NO:6) to LGR7 was significantly lower than that of H2 Relaxin or P74C13V (SEQ ID NO:10). Therefore, even though P59C13V (SEQ ID NO:6) peptide is capable of activating the receptor at high concentration, no real dose response was demonstrated.

Figure 19A:
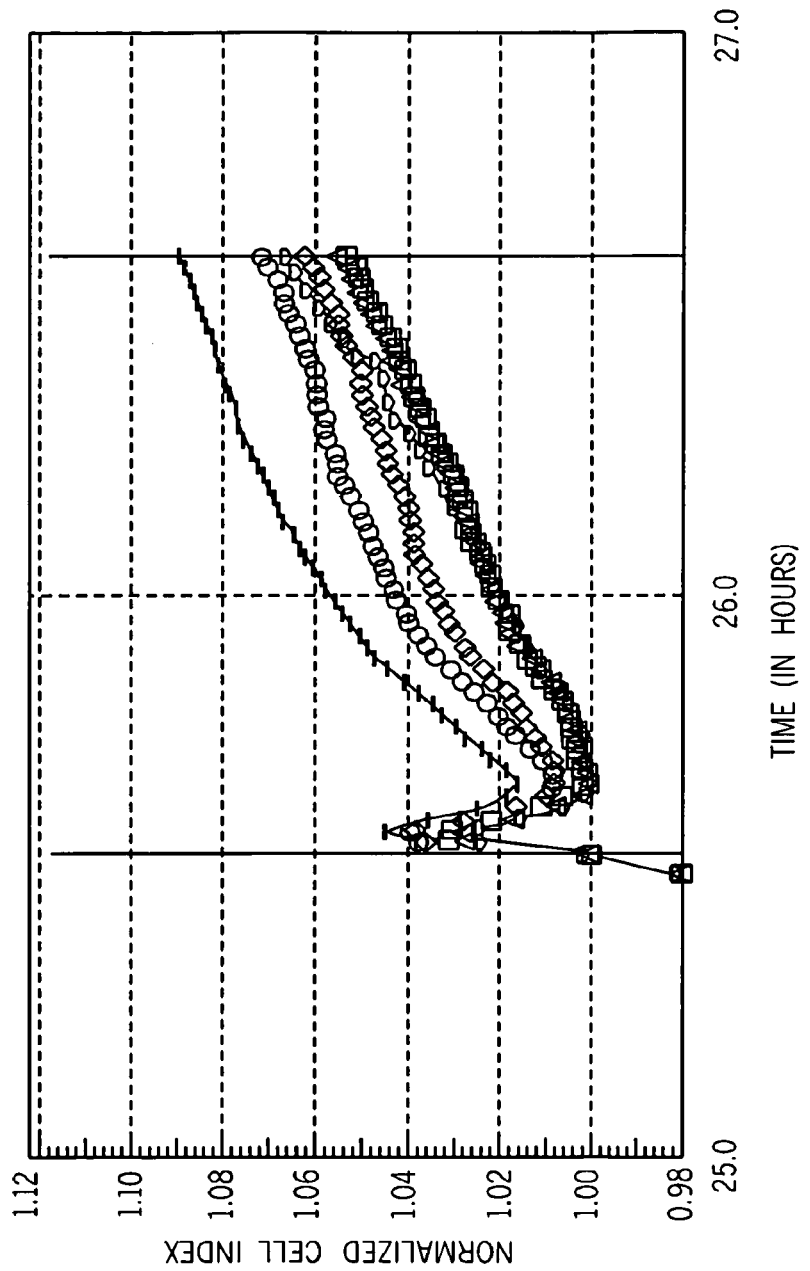
FIG. 19A-B is a graph showing the cell impedance and cytoskeleton remodeling effect (measured by ACEA RT-CES system) as a dose dependant response of different concentrations of P59S-Amide on LGR7 (RXFP1) transfected CHO-K1 cells.

FIG. 19A presents a normalized cell index and a dose response curve for LGR7 transfected CHO-K1 cells challenged by increasing concentrations of peptide P59S-Amide (P59S) (SEQ ID NO: 1) (the dashed Vertical lines indicates the 26$^{th}$ hour from the beginning of the experiment). The P59S (SEQ ID NO: 1) concentrations tested were 41 nM; 123 nM; 370 nM; 1.1 uM; 3.3 uM; 10 uM. As shown in FIG. 19A, there is a moderate dose response for the high concentrations.

Figure 19B:
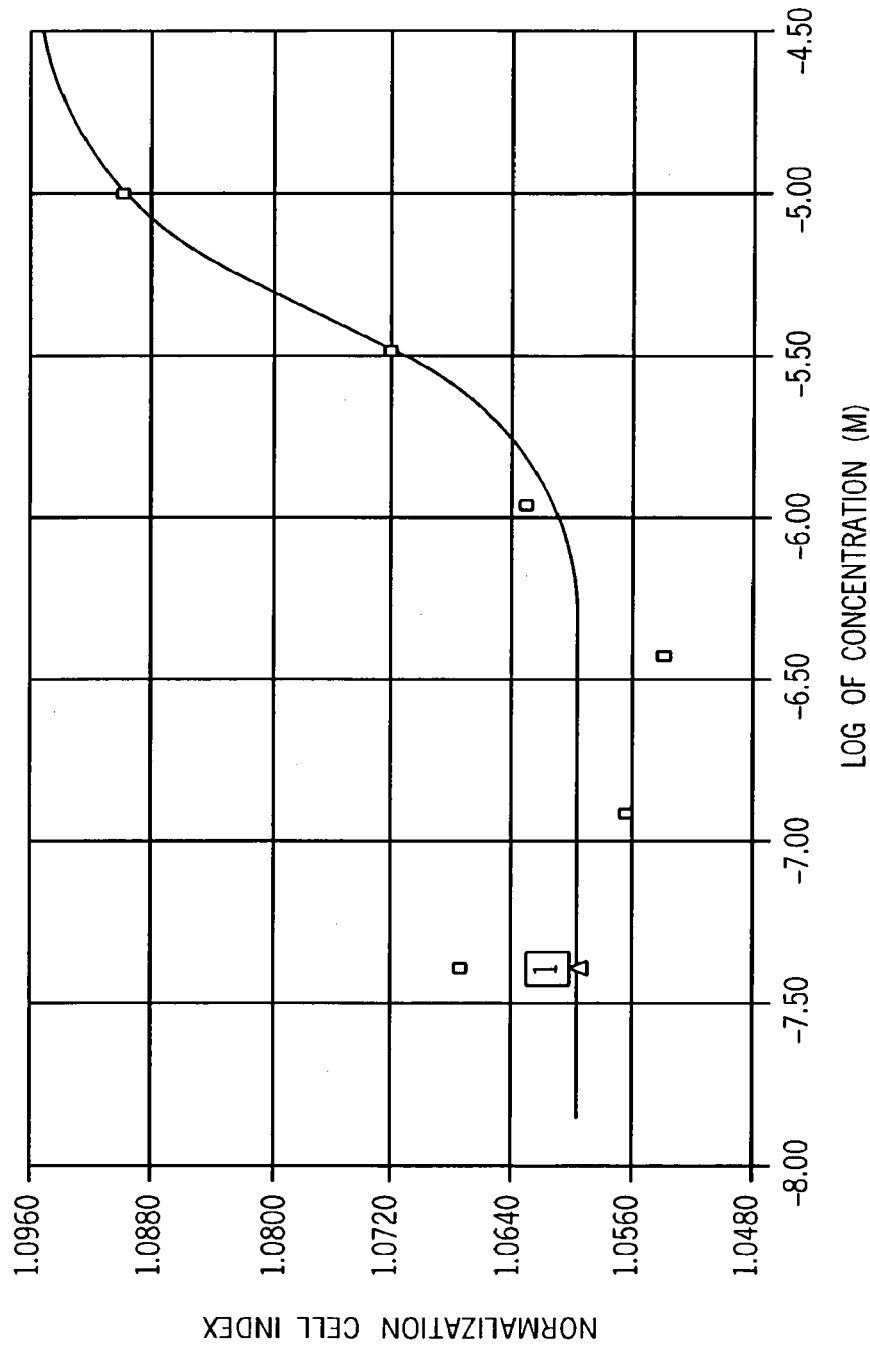

FIG. 19B presents a normalized cell index and a dose response curve for LGR7 transfected CHO-K1 cells challenged by increasing concentrations of P59S-Amide (P59S) (SEQ ID NO: 1) at time point 26.5 hours (vertical right line in FIG. 18A). A dose response is presented as a normalized cell index per Log of concentration (M). As can be seen from FIG. 19B, a mild dose dependent activation of LGR7 by P59C13V (SEQ ID NO:6) was found. Only the highest concentration (10 uM) showed a significant higher cell index rate as compared to the other concentrations. Therefore, even though this peptide is capable of activating the receptor at high concentration, no dose response was demonstrated.

EXAMPLE 8

The P59 Sequence in the C1QTNF8 Protein is Highly Conserved Throughout Other Species and Orthologs, as Well as at Least One Human Paralog (C1QTNF1)

FIG. 20 shows a multiple alignment comparison of the sequence of P59-G (SEQ ID No. 12), representing a fragment of the native human precursor (C1QTNF8-SEQ. ID. No. 19), and homologous sequences derived from various organisms, including Chimpanzee (SEQ ID No. 20), Orangutan (SEQ ID No. 21), Rhesus (SEQ ID No. 22), Cow (SEQ ID No. 23), Chicken (SEQ ID No. 24) and Rat (SEQ ID No. 26). The multiple sequence alignment comparison includes the corresponding peptide sequence derived from the human paralogue C1QTNF1 (SEQ ID No. 25). As can be seen both the N-terminal end (4 Amino acids) and C-terminal end (7 Amino acids) are identical to all species. The cleavage sites at both ends are also highly conserved (with occasional replacement of K for an R). The middle Cysteine residue (C13) that was replaced with Valine for dimerization purposes is highly conserved as well.

The descriptions given are intended to exemplify, but not limit, the scope of the invention. Additional embodiments are within the claims.

What is claimed is:

1. A method of treating a fibrotic disorder or condition comprising administering to a subject in need thereof a peptide less than 35 amino acids in length,
wherein said peptide comprises the amino acid sequence AYAAFSV (SEQ ID NO:2), and
wherein the peptide is delivered for a time, frequency and amount effective to decrease the fibrotic disorder or condition in the subject.

2. The method of claim 1, wherein said peptide comprises an amino acid sequence selected from the group consisting of:

AYAAFSV-Amide (SEQ ID NO: 1)

AYAAFSV; (SEQ ID NO: 2)

GQKGQVGPPGAACRRAYAAFSV-Amide; (SEQ ID NO: 3)

GQKGQVGPPGAACRRAYAAFSV; (SEQ ID NO: 4)

GQKGQVGPPGAAVRRAYAAFSV-Amide; (SEQ ID NO: 5)

GQKGQVGPPGAAVRRAYAAFSV; (SEQ ID NO: 6)

GQKGQVGPPGAACRRAYAAFSVGRRAYAAFSV-Amide; (SEQ ID NO: 7)

GQKGQVGPPGAACRRAYAAFSVGRRAYAAFSV; (SEQ ID NO: 8)

GQKGQVGPPGAAVRRAYAAFSVGRRAYAAFSV-Amide; (SEQ ID NO: 9)

GQKGQVGPPGAAVRRAYAAFSVGRRAYAAFSV; (SEQ ID NO: 10)

AYAAFSVG; (SEQ ID NO: 11)

GQKGQVGPPGAACRRAYAAFSVG; (SEQ ID NO: 12)

GQKGQVGPPGAAVRRAYAAFSVG; (SEQ ID NO: 13)

GQKGQVGPPGAACRRAYAAFSVGRRAYAAFSVG; (SEQ ID NO: 14)

GQKGQVGPPGAAVRRAYAAFSVGRRAYAAFSVG; (SEQ ID NO: 15)

GQKGQVGPPGAACQRAYAAFSVG; (SEQ ID NO: 20)

GQKGQVGPPGAPCQRAYAAFSVG; (SEQ ID NO: 21)

GQKGQVGPPGAPCQRAYAAFSVG; (SEQ ID NO: 22)

GQKGQAGLPGAQCPRAYAAFSVG; (SEQ ID NO: 23)

GQKGQPGPQGHSCKQLYAAFSVG; (SEQ ID NO: 24)

GQKGSMGAPGERCKSHYAAFSVG; (SEQ ID NO: 25)
and

GQKGSMGAPGDHCKSQYAAFSVG. (SEQ ID NO: 26)

3. The method of claim 1, wherein said peptide is conjugated or fused to a second non-GPCR ligand peptide or polypeptide.

4. The method of claim 1, wherein said peptide binds to and/or activates a GPCR in the LGR family of receptors or the relaxin-related family of receptors.

5. The method of claim 1, wherein said peptide is an enzymatic cleavage product of a naturally occurring protein isolated from a cell.

6. The method of claim 1, wherein said peptide is isolated from a protein recombinantly produced in a prokaryotic or eukaryotic cell, or wherein said peptide is chemically synthesized in vitro.

7. The method of claim 1 wherein said peptide includes a C-terminal amidated amino acid.

8. The method of claim 1, wherein said peptide is less than 10 amino acids in length.

9. The method of claim 1, wherein the fibrotic condition is associated with tissue remodeling following inflammation, ischemia-reperfusion injury or respiratory disease.

10. The method of claim 1, wherein the fibrotic condition is selected from the group consisting of endomyocardial fibrosis, cardiac fibrosis; mediastinal fibrosis; idiopathy pulmonary fibrosis; pulmonary fibrosis; retroperitoneal fibrosis; fibrosis of the spleen; fibrosis of the pancreas; hepatic fibrosis (cirrhosis) alcohol abuse, non-alcohol related fibrosis, fibrosis resulting from a viral infection, fibromatosis; granulomatous lung disease; glomerulonephritis, myocardial scarring following infarction; endometrial fibrosis, endometriosis; and wound healing.

11. The method of claim 1, wherein the fibrotic condition is pulmonary fibrosis or idiopathic pulmonary fibrosis.

12. The method of claim 10, wherein said fibrotic condition is wound healing.

13. The method of claim 12, wherein wound healing is selected from the group consisting of injury, surgical procedures, and diabetes related wound fibrosis.

14. The method of claim 9, wherein the respiratory disease is selected from the group consisting of asthma, bronchial disease, lung diseases, chronic obstructive pulmonary disease (COPD), Acute Respiratory Distress Syndrome (ARDS), severe acute respiratory syndrome (SARS), Fibrosis related Asthma, and cystic fibrosis.

15. The method of claim 9, wherein the viral infection is caused by a virus selected from the group consisting of HAV, HBV and HCV.

16. The method of claim 1, wherein said peptide comprises the amino acid sequence of SEQ ID NO: 1.

17. The method of claim 1, wherein said peptide consists of the amino acid sequence of SEQ ID NO: 1.

18. The method of claim 1, wherein said peptide comprises the amino acid sequence of SEQ ID NO: 2.

19. The method of claim 1, wherein said peptide consists of the amino acid sequence of SEQ ID NO: 2.

20. The method of claim 9, wherein the respiratory disease is selected from the group consisting of asthma, fibrosis related asthma and chronic obstructive pulmonary disease (COPD).

21. The method of claim 1, wherein said peptide is a non-enzymatic cleavage product of a naturally occurring protein isolated from a cell.

22. The method of claim 1, wherein the peptide is a non-naturally occurring peptide.

23. The method of claim 1, wherein the peptide is administered to reach an effective concentration of 0.16 nM to 10 µM in the subject.

24. The method of claim 22, wherein the peptide is administered to reach an effective concentration of 0.16 nM to 10 µM in the subject.

* * * * *

SEQUENCE LISTING

<160> NUMBER OF SEQ ID NOS: 35

<210> SEQ ID NO 1
<211> LENGTH: 7
<212> TYPE: PRT
<213> ORGANISM: Artificial sequence
<220> FEATURE:
<223> OTHER INFORMATION: Chemically synthesized peptide
<220> FEATURE:
<221> NAME/KEY: MOD_RES
<222> LOCATION: (7)..(7)
<223> OTHER INFORMATION: AMIDATION

<400> SEQUENCE: 1

Ala Tyr Ala Ala Phe Ser Val
1               5

<210> SEQ ID NO 2
<211> LENGTH: 7
<212> TYPE: PRT
<213> ORGANISM: Artificial sequence
<220> FEATURE:
<223> OTHER INFORMATION: Chemically synthesized peptide

<400> SEQUENCE: 2

Ala Tyr Ala Ala Phe Ser Val
1               5

<210> SEQ ID NO 3
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MOD_RES
<222> LOCATION: (22)..(22)
<223> OTHER INFORMATION: AMIDATION

<400> SEQUENCE: 3

Gly Gln Lys Gly Gln Val Gly Pro Pro Gly Ala Ala Cys Arg Arg Ala
1               5                   10                  15

Tyr Ala Ala Phe Ser Val
            20

<210> SEQ ID NO 4
<211> LENGTH: 22
<212> TYPE: PRT
<213> ORGANISM: Artificial sequence
<220> FEATURE:
<223> OTHER INFORMATION: Chemically synthesized peptide

<400> SEQUENCE: 4

Gly Gln Lys Gly Gln Val Gly Pro Pro Gly Ala Ala Cys Arg Arg Ala
1               5                   10                  15

Tyr Ala Ala Phe Ser Val
            20

<210> SEQ ID NO 5
<211> LENGTH: 22
<212> TYPE: PRT
<213> ORGANISM: Artificial sequence
<220> FEATURE:
<223> OTHER INFORMATION: Chemically synthesized peptide
<220> FEATURE:
<221> NAME/KEY: MOD_RES
<222> LOCATION: (22)..(22)
<223> OTHER INFORMATION: AMIDATION

<400> SEQUENCE: 5

Gly Gln Lys Gly Gln Val Gly Pro Pro Gly Ala Ala Val Arg Arg Ala
1               5                   10                  15

Tyr Ala Ala Phe Ser Val
            20

<210> SEQ ID NO 6
<211> LENGTH: 22
<212> TYPE: PRT
<213> ORGANISM: Artificial sequence
<220> FEATURE:
<223> OTHER INFORMATION: Chemically synthesized peptide

<400> SEQUENCE: 6

Gly Gln Lys Gly Gln Val Gly Pro Pro Gly Ala Ala Val Arg Arg Ala
1               5                   10                  15

Tyr Ala Ala Phe Ser Val
            20

<210> SEQ ID NO 7
<211> LENGTH: 32

-continued

```
<212> TYPE: PRT
<213> ORGANISM: Artificial sequence
<220> FEATURE:
<223> OTHER INFORMATION: Chemically synthesized peptide
<220> FEATURE:
<221> NAME/KEY: MOD_RES
<222> LOCATION: (32)..(32)
<223> OTHER INFORMATION: AMIDATION

<400> SEQUENCE: 7
```

Gly Gln Lys Gly Gln Val Gly Pro Pro Gly Ala Ala Cys Arg Arg Ala
1               5                   10                  15

Tyr Ala Ala Phe Ser Val Gly Arg Arg Ala Tyr Ala Ala Phe Ser Val
            20                  25                  30

```
<210> SEQ ID NO 8
<211> LENGTH: 32
<212> TYPE: PRT
<213> ORGANISM: Artificial sequence
<220> FEATURE:
<223> OTHER INFORMATION: Chemically synthesized peptide

<400> SEQUENCE: 8
```

Gly Gln Lys Gly Gln Val Gly Pro Pro Gly Ala Ala Cys Arg Arg Ala
1               5                   10                  15

Tyr Ala Ala Phe Ser Val Gly Arg Arg Ala Tyr Ala Ala Phe Ser Val
            20                  25                  30

```
<210> SEQ ID NO 9
<211> LENGTH: 32
<212> TYPE: PRT
<213> ORGANISM: Artificial sequence
<220> FEATURE:
<223> OTHER INFORMATION: Chemically synthesized peptide
<220> FEATURE:
<221> NAME/KEY: MOD_RES
<222> LOCATION: (32)..(32)
<223> OTHER INFORMATION: AMIDATION

<400> SEQUENCE: 9
```

Gly Gln Lys Gly Gln Val Gly Pro Pro Gly Ala Ala Val Arg Arg Ala
1               5                   10                  15

Tyr Ala Ala Phe Ser Val Gly Arg Arg Ala Tyr Ala Ala Phe Ser Val
            20                  25                  30

```
<210> SEQ ID NO 10
<211> LENGTH: 32
<212> TYPE: PRT
<213> ORGANISM: Artificial sequence
<220> FEATURE:
<223> OTHER INFORMATION: Chemically synthesized peptide

<400> SEQUENCE: 10
```

Gly Gln Lys Gly Gln Val Gly Pro Pro Gly Ala Ala Val Arg Arg Ala
1               5                   10                  15

Tyr Ala Ala Phe Ser Val Gly Arg Arg Ala Tyr Ala Ala Phe Ser Val
            20                  25                  30

```
<210> SEQ ID NO 11
<211> LENGTH: 8
<212> TYPE: PRT
<213> ORGANISM: Artificial sequence
<220> FEATURE:
<223> OTHER INFORMATION: Chemically synthesized peptide

<400> SEQUENCE: 11
```

```
Ala Tyr Ala Ala Phe Ser Val Gly
1               5

<210> SEQ ID NO 12
<211> LENGTH: 23
<212> TYPE: PRT
<213> ORGANISM: Artificial sequence
<220> FEATURE:
<223> OTHER INFORMATION: Chemically synthesized peptide

<400> SEQUENCE: 12

Gly Gln Lys Gly Gln Val Gly Pro Pro Gly Ala Ala Cys Arg Arg Ala
1               5                   10                  15

Tyr Ala Ala Phe Ser Val Gly
            20

<210> SEQ ID NO 13
<211> LENGTH: 23
<212> TYPE: PRT
<213> ORGANISM: Artificial sequence
<220> FEATURE:
<223> OTHER INFORMATION: Chemically synthesized peptide

<400> SEQUENCE: 13

Gly Gln Lys Gly Gln Val Gly Pro Pro Gly Ala Ala Val Arg Arg Ala
1               5                   10                  15

Tyr Ala Ala Phe Ser Val Gly
            20

<210> SEQ ID NO 14
<211> LENGTH: 33
<212> TYPE: PRT
<213> ORGANISM: Artificial sequence
<220> FEATURE:
<223> OTHER INFORMATION: Chemically synthesized peptide

<400> SEQUENCE: 14

Gly Gln Lys Gly Gln Val Gly Pro Pro Gly Ala Ala Cys Arg Arg Ala
1               5                   10                  15

Tyr Ala Ala Phe Ser Val Gly Arg Arg Ala Tyr Ala Ala Phe Ser Val
            20                  25                  30

Gly

<210> SEQ ID NO 15
<211> LENGTH: 33
<212> TYPE: PRT
<213> ORGANISM: Artificial sequence
<220> FEATURE:
<223> OTHER INFORMATION: Chemically synthesized peptide

<400> SEQUENCE: 15

Gly Gln Lys Gly Gln Val Gly Pro Pro Gly Ala Ala Val Arg Arg Ala
1               5                   10                  15

Tyr Ala Ala Phe Ser Val Gly Arg Arg Ala Tyr Ala Ala Phe Ser Val
            20                  25                  30

Gly

<210> SEQ ID NO 16
<211> LENGTH: 17
<212> TYPE: PRT
<213> ORGANISM: Artificial sequence
<220> FEATURE:
<223> OTHER INFORMATION: Chemically synthesized peptide
```

```
<400> SEQUENCE: 16

Met Ala Ala Pro Ala Leu Leu Leu Ala Leu Leu Leu Pro Val Gly
1               5                   10                  15

Ala

<210> SEQ ID NO 17
<211> LENGTH: 19
<212> TYPE: PRT
<213> ORGANISM: Artificial sequence
<220> FEATURE:
<223> OTHER INFORMATION: Chemically synthesized peptide

<400> SEQUENCE: 17

Met Ala Ala Pro Ala Leu Leu Leu Ala Leu Leu Leu Pro Val Gly
1               5                   10                  15

Ala Trp Pro

<210> SEQ ID NO 18
<211> LENGTH: 22
<212> TYPE: PRT
<213> ORGANISM: Artificial sequence
<220> FEATURE:
<223> OTHER INFORMATION: Chemically synthesized peptide

<400> SEQUENCE: 18

Met Ala Ala Pro Ala Leu Leu Leu Ala Leu Leu Leu Pro Val Gly
1               5                   10                  15

Ala Trp Pro Gly Leu Pro
            20

<210> SEQ ID NO 19
<211> LENGTH: 262
<212> TYPE: PRT
<213> ORGANISM: Homo sapiens

<400> SEQUENCE: 19

Met Ala Ala Pro Ala Leu Leu Leu Ala Leu Leu Leu Pro Val Gly
1               5                   10                  15

Ala Trp Pro Gly Leu Pro Arg Arg Pro Cys Val His Cys Cys Arg Pro
            20                  25                  30

Ala Trp Pro Pro Gly Pro Tyr Ala Arg Val Ser Asp Arg Asp Leu Trp
        35                  40                  45

Arg Gly Asp Leu Trp Arg Gly Leu Pro Arg Val Arg Pro Thr Ile Asp
    50                  55                  60

Ile Glu Ile Leu Lys Gly Glu Lys Gly Glu Ala Gly Val Arg Gly Arg
65                  70                  75                  80

Ala Gly Arg Ser Gly Lys Glu Gly Pro Gly Ala Arg Gly Leu Gln
                85                  90                  95

Gly Arg Arg Gly Gln Lys Gly Gln Val Gly Pro Pro Gly Ala Ala Cys
                100                 105                 110

Arg Arg Ala Tyr Ala Ala Phe Ser Val Gly Arg Arg Ala Tyr Ala Ala
                115                 120                 125

Phe Ser Val Gly Arg Arg Glu Gly Leu His Ser Ser Asp His Phe Gln
            130                 135                 140

Ala Val Pro Phe Asp Thr Glu Leu Val Asn Leu Asp Gly Ala Phe Asp
145                 150                 155                 160

Leu Ala Ala Gly Arg Phe Leu Cys Thr Val Pro Gly Val Tyr Phe Leu
                165                 170                 175
```

```
Ser Leu Asn Val His Thr Trp Asn Tyr Lys Glu Thr Tyr Leu His Ile
            180                 185                 190

Met Leu Asn Arg Arg Pro Ala Ala Val Leu Tyr Ala Gln Pro Ser Glu
        195                 200                 205

Arg Ser Val Met Gln Ala Gln Ser Leu Met Leu Leu Leu Ala Ala Gly
    210                 215                 220

Asp Ala Val Trp Val Arg Met Phe Gln Arg Asp Arg Asp Asn Ala Ile
225                 230                 235                 240

Tyr Gly Glu His Gly Asp Leu Tyr Ile Thr Phe Ser Gly His Leu Val
                245                 250                 255

Lys Pro Ala Ala Glu Leu
            260

<210> SEQ ID NO 20
<211> LENGTH: 23
<212> TYPE: PRT
<213> ORGANISM: Pan sp.

<400> SEQUENCE: 20

Gly Gln Lys Gly Gln Val Gly Pro Pro Gly Ala Ala Cys Gln Arg Ala
1               5                   10                  15

Tyr Ala Ala Phe Ser Val Gly
            20

<210> SEQ ID NO 21
<211> LENGTH: 23
<212> TYPE: PRT
<213> ORGANISM: Pongo sp.

<400> SEQUENCE: 21

Gly Gln Lys Gly Gln Val Gly Pro Pro Gly Ala Pro Cys Gln Arg Ala
1               5                   10                  15

Tyr Ala Ala Phe Ser Val Gly
            20

<210> SEQ ID NO 22
<211> LENGTH: 23
<212> TYPE: PRT
<213> ORGANISM: Macaca sp.

<400> SEQUENCE: 22

Gly Gln Lys Gly Gln Val Gly Pro Pro Gly Ala Pro Cys Gln Arg Ala
1               5                   10                  15

Tyr Ala Ala Phe Ser Val Gly
            20

<210> SEQ ID NO 23
<211> LENGTH: 23
<212> TYPE: PRT
<213> ORGANISM: Bos sp.

<400> SEQUENCE: 23

Gly Gln Lys Gly Gln Ala Gly Leu Pro Gly Ala Gln Cys Pro Arg Ala
1               5                   10                  15

Tyr Ala Ala Phe Ser Val Gly
            20

<210> SEQ ID NO 24
<211> LENGTH: 23
<212> TYPE: PRT
<213> ORGANISM: Gallus sp.
```

```
<400> SEQUENCE: 24

Gly Gln Lys Gly Gln Pro Gly Pro Gln Gly His Ser Cys Lys Gln Leu
1               5                   10                  15

Tyr Ala Ala Phe Ser Val Gly
            20

<210> SEQ ID NO 25
<211> LENGTH: 23
<212> TYPE: PRT
<213> ORGANISM: Homo sapiens

<400> SEQUENCE: 25

Gly Gln Lys Gly Ser Met Gly Ala Pro Gly Glu Arg Cys Lys Ser His
1               5                   10                  15

Tyr Ala Ala Phe Ser Val Gly
            20

<210> SEQ ID NO 26
<211> LENGTH: 23
<212> TYPE: PRT
<213> ORGANISM: Rattus sp.

<400> SEQUENCE: 26

Gly Gln Lys Gly Ser Met Gly Ala Pro Gly Asp His Cys Lys Ser Gln
1               5                   10                  15

Tyr Ala Ala Phe Ser Val Gly
            20

<210> SEQ ID NO 27
<211> LENGTH: 27
<212> TYPE: PRT
<213> ORGANISM: Homo sapiens

<400> SEQUENCE: 27

Arg Arg Gly Gln Lys Gly Gln Val Gly Pro Pro Gly Ala Ala Cys Arg
1               5                   10                  15

Arg Ala Tyr Ala Ala Phe Ser Val Gly Arg Arg
            20                  25

<210> SEQ ID NO 28
<211> LENGTH: 27
<212> TYPE: PRT
<213> ORGANISM: Pan sp.

<400> SEQUENCE: 28

Arg Lys Gly Gln Lys Gly Gln Val Gly Pro Pro Gly Ala Ala Cys Gln
1               5                   10                  15

Arg Ala Tyr Ala Ala Phe Ser Val Gly Arg Arg
            20                  25

<210> SEQ ID NO 29
<211> LENGTH: 27
<212> TYPE: PRT
<213> ORGANISM: Pongo sp.

<400> SEQUENCE: 29

Arg Lys Gly Gln Lys Gly Gln Val Gly Pro Pro Gly Ala Pro Cys Gln
1               5                   10                  15

Arg Ala Tyr Ala Ala Phe Ser Val Gly Arg Arg
            20                  25
```

```
<210> SEQ ID NO 30
<211> LENGTH: 27
<212> TYPE: PRT
<213> ORGANISM: Macaca sp.

<400> SEQUENCE: 30

Arg Lys Gly Gln Lys Gly Gln Val Gly Pro Pro Gly Ala Pro Cys Gln
1               5                   10                  15

Arg Ala Tyr Ala Ala Phe Ser Val Gly Arg Arg
            20                  25

<210> SEQ ID NO 31
<211> LENGTH: 27
<212> TYPE: PRT
<213> ORGANISM: Bos sp.

<400> SEQUENCE: 31

Arg Lys Gly Gln Lys Gly Gln Ala Gly Leu Pro Gly Ala Gln Cys Pro
1               5                   10                  15

Arg Ala Tyr Ala Ala Phe Ser Val Gly Arg Arg
            20                  25

<210> SEQ ID NO 32
<211> LENGTH: 27
<212> TYPE: PRT
<213> ORGANISM: Gallus sp.

<400> SEQUENCE: 32

Arg Lys Gly Gln Lys Gly Gln Pro Gly Pro Gln Gly His Ser Cys Lys
1               5                   10                  15

Gln Leu Tyr Ala Ala Phe Ser Val Gly Arg Arg
            20                  25

<210> SEQ ID NO 33
<211> LENGTH: 27
<212> TYPE: PRT
<213> ORGANISM: Homo sapiens

<400> SEQUENCE: 33

Pro Lys Gly Gln Lys Gly Ser Met Gly Ala Pro Gly Glu Arg Cys Lys
1               5                   10                  15

Ser His Tyr Ala Ala Phe Ser Val Gly Arg Lys
            20                  25

<210> SEQ ID NO 34
<211> LENGTH: 27
<212> TYPE: PRT
<213> ORGANISM: Rattus sp.

<400> SEQUENCE: 34

Pro Lys Gly Gln Lys Gly Ser Met Gly Ala Pro Gly Asp His Cys Lys
1               5                   10                  15

Ser Gln Tyr Ala Ala Phe Ser Val Gly Arg Arg
            20                  25

<210> SEQ ID NO 35
<211> LENGTH: 27
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
```

```
<222> LOCATION: (8)..(8)
<223> OTHER INFORMATION: Wherein Xaa is any amino acid.
<220> FEATURE:
<221> NAME/KEY: MISC_FEATURE
<222> LOCATION: (13)..(13)
<223> OTHER INFORMATION: Wherein Xaa is any amino acid.
<220> FEATURE:
<221> NAME/KEY: MISC_FEATURE
<222> LOCATION: (14)..(14)
<223> OTHER INFORMATION: Wherein Xaa is any amino acid.
<220> FEATURE:
<221> NAME/KEY: MISC_FEATURE
<222> LOCATION: (17)..(17)
<223> OTHER INFORMATION: Wherein Xaa is any amino acid.
<220> FEATURE:
<221> NAME/KEY: MISC_FEATURE
<222> LOCATION: (18)..(18)
<223> OTHER INFORMATION: Wherein Xaa is any amino acid.

<400> SEQUENCE: 35

Arg Lys Gly Gln Lys Gly Gln Xaa Gly Pro Pro Gly Xaa Xaa Cys Lys
1               5                  10                  15

Xaa Xaa Tyr Ala Ala Phe Ser Val Gly Arg Arg
            20                  25
```